(12) United States Patent
Barenholz et al.

(10) Patent No.: US 8,871,276 B2
(45) Date of Patent: *Oct. 28, 2014

(54) BETA-CASEIN ASSEMBLIES FOR MUCOSAL DELIVERY OF THERAPEUTIC BIOACTIVE AGENTS

(75) Inventors: Yechezkel Barenholz, Jerusalem (IL); Dganit Danino, Nesher (IL)

(73) Assignee: Technion Research and Development Foundation Ltd., Haifa (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/212,615

(22) Filed: Aug. 18, 2011

(65) Prior Publication Data

US 2012/0070469 A1 Mar. 22, 2012

Related U.S. Application Data

(63) Continuation-in-part of application No. 12/867,215, filed as application No. PCT/IL2009/000155 on Feb. 11, 2009.

(60) Provisional application No. 61/027,633, filed on Feb. 11, 2008, provisional application No. 61/030,005, filed on Feb. 20, 2008, provisional application No. 61/374,647, filed on Aug. 18, 2010.

(51) Int. Cl.
| | |
|---|---|
| A61K 9/14 | (2006.01) |
| A61K 9/16 | (2006.01) |
| A61K 9/50 | (2006.01) |
| A23L 1/305 | (2006.01) |
| A23J 1/22 | (2006.01) |
| A23B 4/03 | (2006.01) |
| A61K 31/665 | (2006.01) |
| A61K 9/00 | (2006.01) |
| A61K 9/107 | (2006.01) |
| A61K 31/415 | (2006.01) |
| A61K 31/573 | (2006.01) |

(52) U.S. Cl.
CPC ............... *A61K 9/00* (2013.01); *A61K 9/1075* (2013.01); *A61K 31/415* (2013.01); *A61K 31/573* (2013.01)
USPC ............. 424/499; 424/489; 426/72; 426/443; 426/657; 514/100; 514/141; 514/403

(58) Field of Classification Search
None
See application file for complete search history.

(56) References Cited

U.S. PATENT DOCUMENTS

| | | | |
|---|---|---|---|
| 5,173,322 A | 12/1992 | Melachouris | |
| 5,318,793 A | 6/1994 | Melachouris | |
| 5,399,363 A | 3/1995 | Liversidge | |
| 5,405,756 A | 4/1995 | Naito | |
| 5,462,751 A | 10/1995 | Kossovsky | |
| 5,603,930 A | 2/1997 | Brassart | |
| 5,833,953 A | 11/1998 | Berrocal | |
| 6,290,974 B1 | 9/2001 | Swaisgood | |
| 6,503,545 B1 | 1/2003 | Perlman | |
| 6,652,875 B1 | 11/2003 | Bannister | |
| 6,991,823 B2 | 1/2006 | Augustin | |
| 2002/0054914 A1 | 5/2002 | Morcol | |
| 2003/0180367 A1 | 9/2003 | Parikh | |
| 2004/0137071 A1 | 7/2004 | Unger | |
| 2004/0234666 A1* | 11/2004 | Law et al. ...................... 426/580 |
| 2005/0031544 A1 | 2/2005 | Njemanze | |
| 2007/0104847 A1 | 5/2007 | O'Mahony | |
| 2007/0166368 A1 | 7/2007 | Singh | |
| 2008/0145432 A1 | 6/2008 | Kakizawa | |
| 2009/0029017 A1 | 1/2009 | Singh | |
| 2010/0062073 A1* | 3/2010 | Beyerinck et al. ............ 424/491 |
| 2011/0038987 A1* | 2/2011 | Danino et al. .................. 426/73 |
| 2011/0052703 A1 | 3/2011 | Barenholz | |

FOREIGN PATENT DOCUMENTS

| | | |
|---|---|---|
| EP | 1348430 | 10/2003 |
| GB | 2041378 | 9/1980 |
| WO | 96/29340 A1 | 9/1996 |
| WO | 00/06108 A1 | 2/2000 |
| WO | 02064112 | 8/2002 |
| WO | 2004000252 | 12/2003 |
| WO | 2007017513 | 2/2007 |
| WO | 2007069272 | 6/2007 |
| WO | 2007/122613 A1 | 11/2007 |
| WO | 2008135852 | 11/2008 |
| WO | 2009101612 | 8/2009 |
| WO | 2009101613 | 8/2009 |
| WO | 2009101614 | 8/2009 |

OTHER PUBLICATIONS

Horne, David S.; Current Opinion in Colloid and Interface Science 7 (2002) 456-461.*
le Graet et al.; Lait (1993) 73, pp. 51-60.*
le Graet et al.; J. Dairy Research (1999) 66, pp. 215-224.*
Bellare, J. R. et al., (1988) Controlled environment vitrification system: an improved sample preparation technique. Electron Microsc. Technique 10:87-111.

(Continued)

*Primary Examiner* — Jeffrey T Palenik
(74) *Attorney, Agent, or Firm* — Browdy and Neimark, PLLC

(57) ABSTRACT

The present invention discloses a dried composition comprising β-casein micelles, assemblies and complexes thereof. The dried composition is stable in the dried state as well as upon re-suspension The dried composition retains the biological activity, drug load capacity, particle size and particle size distribution of the β-casein micelles, assemblies and complexes comprising the active pharmaceutical ingredient, within the dried state and upon resuspension in a buffer or an aqueous pharmaceutical carrier.

26 Claims, 38 Drawing Sheets

(56) References Cited

OTHER PUBLICATIONS

O'Connell, J. et al., (2003) Association behavior of beta-casein. Journal of Colloid and Interface Science 258(1): 33-39.

Pan, X. et al., (2007) Simultaneous nanoparticle formation and encapsulation driven by hydrophobic interaction of casein-graft-dextran and beta-carotene. Journal of Colloid and Interface Science 315:456-463.

Portnaya, I. et al., (2006) Micellization of bovine beta-casein studied by isothermal titration microcalorimetry and cryogenic transmission electron microscopy. J. Agric. Food Chem. 54:5555-5561.

Portnaya, I. et al., (2008) Self-assembly of bovine beta-casein below the isoelectric Ph. J Agric Food Chem. 56 (6):2192-2198.

Semo, E. et al., (2007) Casein micelle as a natural nano-capsular vehicle for nutraceuticals. Food Hydrocolloids 21 (5-6):936-42.

Zhang, X. et al., (2005) Chaperone-like activity of beta-casein. Int. J. Biochem. Cell Biol. 37(6):1232-40.

Database Biosis [Online], Biosciences informaiotn service, Philadelphia, PA, US; 1979, Evans, M. T. et al., The conformation and aggregation of bovine β-casein A. II. Thermodynamics of thermal association and the effects of changes in polar and apolar interactions on micellization, XP002531439 Database accession No. PREV197968060329 abstract & Biopolymers 1979;18(5):1123-1140.

Aoki et al., (1988) Incorporation of individual casein constituents into micelles in artificial casein micelles. Nippon Chikusan Gakkaiho 60:583-589.

Bootz et al., (2004) Comparison of scanning electron microscopy, dynamic light scattering and analytical ultracentrifugation for the sizing of poly(butyl cyanoacrylate) nanoparticles. Eur J Pharm Biopharm 57(2):369-375.

Brophy et al., (2003) Cloned transgenic cattle produce milk with higher levels of beta-casein and kappa-casein. Nat Biotechnol 21(2):157-162.

Christiens et al., (2002), Tryptophan fluorescence study of the interaction of penetratin peptides with model membranes. Eur J Biochem 269(12):2918-2926.

Cogan et al., (1976) Binding affinities of retinol and related compounds to retinol binding proteins. Eur J Biochem 65:71-8.

Dalgleish and Law (1988) Sodium caseinates—composition and properties of different preparations. International Journal of Dairy Technology 41(1): 1-4.

Farrell et al., (2006), Casein micelle structure: What can be learned from milk synthesis and structural biology?. Current Opinion in Colloid and Interface Science 11:135-147.

Fornier et al., (2007) Increased dose density is feasible: a pilot study of adjuvant epirubicin and cyclophosphamide followed by paclitaxel, at 10- or 11-day intervals with filgrastim support in women with breast cancer. Clin Cancer Res 13(1):223-227.

Forrest et al., (2005) Interactions of vitamin D3 with bovine beta-lactoglobulin A and beta-casein. J Agric Food Chem 53(20):8003-8009.

Guo et al., (2003) Casein precipitation equilibria in the presence of calcium ions and phosphates. Colloids and Surfaces B: Biointerfaces 29: 297-307.

Hogan et al., (2001) Microencapsulating Properties of Sodium Caseinate. Journal of Agricultural and Food Chemistry 49:1934-1938.

Horne (1998) Casein Interactions: Casting Light on the Black Boxes, the Structure in Dairy Products. Int Dairy 8(3): 171-7.

Horne (2002) Casein structure, self-assembly and gelation. Current Opinion in Colloid & Interface Science 7 (5-6):456-461.

Jubeh et al., (2004) Differential adhesion of normal and inflamed rat colonic mucosa by charged liposomes. Pharm Res 21:447-453.

Jubeh et al., (2005) Local prevention of oxidative stress in the intestinal epithelium of the rat by adhesive liposomes of superoxide dismutase and tempamine. Mol Pharm 2(1):2-11.

Jubeh et al.,(2006) Local treatment of experimental colitis in the rat by negatively charged liposomes of catalase, TMN and SOD. J Drug Target 14(3)155-163.

Karlsson et al., (2007) Observations of casein micelles in skim milk concentrate by transmission electron microscopy. LWT—Food Science and Technology 40(6):1102-7.

Kauf and Kensinger (2002) Purification of porcine beta-casein, N-terminal sequence, quantification in mastitic milk. J Anim Sci 80:1863-1870.

Knepp et al., (1993) Synthesis, properties, and intratumoral evaluation of mitoxantrone-loaded casein microspheres in Lewis lung carcinoma. J Pharm Pharmacol 45(10):887-891.

Knoop et al., (1979) Sub-structure of synthetic casein micelles. Journal of Dairy Research 46:347-350.

Livney D., Experimental report: Comparison of the binding of vitamin D to casein under the conditions of D1 and under the conditions of Livney & Dalgleish, measured by spectrofluorometry. Technion Res and Dev Foundation Ltd., EP 07736236.6, filed Oct. 15, 2008.

Mattila et al., (2001), Contents of vitamins, mineral elements, and some phenolic compounds in cultivated mushrooms. Journal of agricultural and food chemistry 49:2343-2348.

Pan et al., (2007) Simultaneous nanoparticle formation and encapsulation driven by hydrophobic interaction of casein-graft-dextran and beta-carotene. Journal of Colloid and Interface Science 315(2):456-463.

Renken and Warthesen (1993) Vitamin D stability in milk. J Food Science 58(3):552-556.

Ribadeau et al., (1972) Primary structure of bovine beta casein. Complete sequence. Eur J Biochem 25(3):505-514—abstract.

Shapira et al., (2012) β-Casein nanoparticle-based oral drug delivery system for potential treatment of gastric carcinoma: stability, target-activated release and cytotoxicity. Eur J Pharm Biopharm 80: 298-305.

Thomsen et al., (1995) Solid-state magic-angle spinning 31P-NMR studies of native casein micelles. Eur J Biochem 230: 454-459.

Tirosh et al., (2009) Transferrin as a luminal target for negatively charged liposomes in the inflamed colonic mucosa. Mol Pharm 6(4):1083-1091.

Weissenboeck et al., (2004) Binding and Uptake of Wheat Germ Agglutinin-Grafted PLGA-Nanospheres by Caco-2 Monolayers. Pharm Res 21(10)1917-1923.

Zhang et al., (2004) Uptake of folate-conjugated albumin nanoparticles to the SKOV3 cells. Int J Pharm 287 (1-2):155-162.

Zimet et al., (2011) Re-assembled casein micelles and casein nanoparticles as nano-vehicles for ω-3 polyunsaturated fatty acids. Food hydrocolloids 25(5):1270-6.

\* cited by examiner

BETA-CASEIN ASSEMBLIES FOR MUCOSAL DELIVERY OF THERAPEUTIC BIOACTIVE AGENTS

FIELD OF THE INVENTION

The present invention relates to drug carrier compositions comprising β-casein micelle assemblies for drug delivery such as mucosal drug delivery. The present invention further provides methods of manufacturing same and therapeutic methods utilizing same.

BACKGROUND OF THE INVENTION

Many drugs and agents delivered orally suffer from poor bioavailability due to many drawbacks including poor drug absorption in the gastrointestinal tract (GI), poor stability in the GI and especially in the stomach, low solubility, etc. For all these cases there is an unmet need to overcome these drawbacks in order to improve drug bioavailability so to achieve therapeutic efficacy through effective drug delivery.

Treatment of many diseases including lethal or chronic illnesses often requires daily use of drugs or therapeutic bioactive agents, for example in the form of injection. This can result in non-compliance of the patient due to the discomfort caused by multiple administrations. In addition to being uncomfortable, injection is also expensive. Enteral delivery of such bioactive agents and drugs may provide an advantageous route for administration and may encourage patient compliance. However, oral administration of such molecules is often restricted by acid digestion of the drugs or bioactive compounds in the stomach and digestion in the small intestine. Thus, many systems focus on protecting the encapsulated molecule from degradation, and facilitating the transport of the intact molecule.

Many existing encapsulation systems for enteral delivery of drugs use biocompatible, semi-permeable polymeric capsules, enclosures or membranes, which deliver the drug to the desired release point (typically along the gastrointestinal tract) and then permit release of the drug. Other such systems use liposomes or other structures to contain the drug. Frequently, such systems provide controlled release of the drug for better therapeutic efficacy, although immediate release is also possible. The material(s) used for surrounding the drug are selected for compatibility with the active ingredient and desired release properties.

Casein, which accounts for about 80% of milk protein, is organized in micelles. Casein micelles (CM) are designed by nature to efficiently concentrate, stabilize and transport essential nutrients, mainly calcium ions and protein, for the neonate. All mammals' milk contains casein micelles. Cow's milk contains 30-35 g of protein per liter, of which about 80% is within CM.

CM are usually described as clusters of unorganized mixture of the main four caseins: $\alpha_{s1}$-casein ($\alpha_{s1}$-CN), $\alpha_{s2}$-CN, β-CN, and κ-CN (molar ratio ~4:1:4:1 respectively (DeKruif and Holt, Advanced Dairy Chemistry-1 Proteins Part A; 3 Fox, P F; McSweeney, P. L. H., Eds.; Kluwer Academic/Plenum Publishers: New York, 2005; 233-276). The caseins are held together in the micelles by hydrophobic interactions as well as by calcium-phosphate bridges. CM form only at neutral pH and their typical sizes are in the range of 50-500 nm and their average is 150 nm.

Harnessing CM for nano-encapsulation and stabilization of hydrophobic nutraceutical substances was suggested in the prior art. Semo et al., referred to the incorporation of such CM nano-capsules in dairy products without modifying their sensory properties (Semo E. Food Hydrocolloids 2007, 21; 936-42) and further suggested their use as delivery agents of sensitive health-promoting substances using natural GRAS (generally regarded as safe) ingredients.

PCT Publication WO 2007/122613 described a system based on re-assembled casein micelles with calcium ions for the delivery of hydrophobic biologically active compounds in food and beverages. The teachings specifically relate to the incorporation of such re-assembled casein micelles into low-fat or non-fat dairy products or other food or beverage products without adversely modifying their properties. The CM are composed of sodium caseinate comprising at least the main four casein proteins and are re-assembled at neutral pH and a source of calcium ions. The reassembly of CM is enforced by flow and exposure to high pressure.

PCT Publication WO 2008/135852 described nanoparticle compositions based on a poorly aqueous soluble non-ionizable polymer, a low-solubility drug and β-casein. According to this publication, the non-ionizable polymer used in the nanoparticles, is essential for stabilizing the poorly-water soluble drug, and maintaining the drug in an amorphous form, which is needed to increase the drug poor bioavailability. In addition to being an essential component, the non-ionizable polymer constitutes ~50% of the formulation.

U.S. Pat. No. 6,652,875 provides a formulation for the delivery of bioactive agents to biological surfaces comprising at least one isolated and purified casein protein or salt thereof in water. The disclosure relates to particular isolated and purified casein phosphoproteins in the form of casein calcium phosphate complexes intended to remain on the surface of oral cavity tissues or the gastrointestinal tract. Specific particle formation is neither taught nor suggested. Furthermore, the taught micelles comprise a casein protein selected from α-casein, β-casein, κ-casein, and mixtures thereof. This application emphasizes the need for the presence of divalent and trivalent metal ions.

U.S. Patent Application Publication No. 2002/0054914 teaches a calcium phosphate/drug core with casein micelles reconstructed as aggregates around the cores, forming micellar structures, for the delivery of pharmaceutical agents. According to that disclosure, casein molecules are arranged, presumably as micelles, around calcium phosphate particles containing the active drug, and are linked to the therapeutic agent-containing microparticles mainly by calcium phosphate and electrostatic bond interactions.

U.S. Patent Application Publication No. 2009/0029017 provides a protective system for oxidisable lipids by encapsulating them in a complex of casein and whey proteins. The emulsion is reported to stabilize the oxidisable lipid by decreasing its rate of oxidation. The emulsion is further reported to be stable upon heating which allows it to be heat treated and sterilized. However, the emulsion clearly requires a combination of both types of proteins; furthermore, the effect of low pH values and/or low temperature is not discussed. In fact, the pH is stated to be typically between 6 and 9, with the upper end of the range being even more preferred. Also the complex is stated to be formed by heating to between 70-100° C.

Casein-dextran copolymer nanoparticles encapsulating insoluble β-carotene was disclosed by Pan X. et al. (Journal of Colloid and Interface Science, 2007, 315; 456-63). The nanoparticles contained a casein and β-carotene core surrounded by a dextran shell. The particles were shown to have spherical shape with a size of about 100 nm and are stable in aqueous solution even after long term storage. The casein-dextran nanoparticles were suggested as possible delivery agents for unstable and hydrophobic nutrients and drugs. However, the teachings clearly require a casein-dextran copolymer for forming the nanoparticles.

U.S. Pat. No. 5,405,756 discloses acid soluble casein phosphopeptides prepared by enzymatic digestion of intact casein followed by step wise acidification of the digest causing precipitation of acid insoluble molecules. This procedure teaches that caseins tend to precipitate at pH values around the pI of the protein.

The use of β-casein micelles as nano-delivery vehicles for chemotherapeutic drugs was presented in the 48th Microsymposium of PMM Polymer colloids held in Prague, the Czech Republic, during July 2008, and at a scientific gathering in Hagoshrim Israel December 2008, after the priority date of the application from which the present application claims priority. There is still an unmet medical need for effective, safe and easy to manufacture delivery systems for improved bioavailability of bioactive ingredients, particularly for small organic molecules with poor solubility or poor absorption or poor stability or potential adverse effects in the GI tract.

SUMMARY OF THE INVENTION

The present invention discloses for the first time a dried composition comprising β-casein micelles, assemblies and complexes thereof. The dried composition is stable in the dried state and upon re-suspension and thus can be re-constituted to be used as a pharmaceutical. Unexpectedly, the dried composition retains the biological activity, drug load capacity, particle size and particle size distribution of the β-casein micelles, assemblies and complexes comprising an active pharmaceutical ingredient, within the dried state and upon resuspension in a buffer or an aqueous pharmaceutical carrier.

According to a first aspect, the present invention provides a dried composition comprising micelles, assemblies or complexes thereof, the composition comprising a purified or partially purified β-casein and at least one therapeutic agent, wherein the partially purified β-casein is at least about 70% of the total casein content and wherein the micelles, assemblies or complexes are formed without adding calcium ions hence essentially are free of calcium phosphate. In some embodiments, the partially purified β-casein is at least about 80%, more typically at least about 90% and most typically at least about 95% of the total casein content. In another embodiment, a purified β-casein is 100% β-casein. In another embodiment, the phrase "isolated β-casein" encompasses both purified and partially purified β-casein. As a natural food product, this GRAS (generally recognized as safe) protein is biocompatible and biodegradable, which should not elicit immune responses against it.

According to another aspect, the present invention provides a composition comprising micelles, assemblies or complexes thereof, wherein the micelles, assemblies or complexes thereof comprise: (1) β-casein; and (2) at least one therapeutic agent, wherein the composition is a dried composition, wherein said β-casein comprises at least about 70% of the total casein content, wherein the micelles, assemblies or complexes are formed in the absence of calcium ions. According to another aspect, the present invention provides a composition comprising micelles, assemblies or complexes thereof, wherein the micelles, assemblies or complexes thereof comprise: (1) β-casein, and (2) at least one therapeutic agent, wherein the composition is dried and free of calcium, wherein said β-casein comprises at least about 70% of the total casein content.

The dried composition of the invention comprises less than 15% of water (w/w). In a particular embodiment, the dried formulation comprises from 5% to 15% water (w/w).

In one embodiment, the dried composition of the present invention comprises β-casein micelles assemblies or complexes thereof, wherein the composition is formed under acidic conditions at least 1 pH unit below the pI of the β-casein. In this manner, the β-casein is denatured. Alternatively, the dried composition of the present invention comprises β-casein micelles assemblies or complexes thereof, wherein the composition is formed under nautral conditions at least 1 pH unit above the pI of the β-casein (i.e. pH 6.5 to 7.5). In this manner, the β-casein is in its native form. The dried compositions of the present invention can be re-suspended or re-constituted for subsequent use.

In one embodiment, the dried compositions of the present invention are stable (by their size distribution, structure, and composition) over a wide temperature range (optionally at least from about 1° C. to at least about 45° C.) and over prolonged periods of time. In particular, the compositions are stable for at least 2 weeks to at least 6 months.

In another embodiment, the suspension (the dried composition in an aqueous solution) is stable for at least 1 week. In another embodiment, the suspension (the dried composition in an aqueous solution) is stable for at least 2 weeks. In another embodiment, the suspension (the dried composition in an aqueous solution) is stable for at least 1 month. In another embodiment, the composition of the invention (a lyophilized or dried composition) is stable for at least 1 month. In another embodiment, the composition of the invention (a lyophilized or dried composition) is stable for at least 2 months. In another embodiment, the composition of the invention (a lyophilized or dried composition) is stable for at least 6 months. In another embodiment, the composition of the invention (a lyophilized or dried composition) is stable for at least 1 year. The present invention, in some embodiments, further discloses the use of these micelles, assemblies or complexes thereof as carriers for the loading of bioactive compounds, particularly drugs and therapeutic compounds. Optionally and typically, the micelles, assemblies or complexes thereof are suitable for the delivery of a bioactive compound or compounds. Delivery, in some embodiments, includes delivery through or across a mucosal membrane for mucosal delivery. Mucosal delivery typically includes delivery across any suitable mucosal membrane, which may be selected by one of ordinary skill in the art according to one or more therapeutic factors. According to some embodiments, the terms "therapeutic factor", "active pharmaceutical ingredient", "bioactive agent" and the like are synonymous.

The therapeutic factors typically include, but are not limited to, the type or characteristic(s) of the bioactive compound(s), the desired therapeutic effect, one or more characteristics of the recipient subject and so forth. Mucosal delivery may optionally include one or more of oral, rectal, nasal or vaginal delivery. Each possibility represents a separate embodiment of the invention.

As noted above, it has now been found that these dried compositions are unexpectedly stable over a wide pH range and at a wide temperature range. As a natural, digestible food component, β-casein is biocompatible, and thus should not elicit immune responses against it. The β-casein micelles, assemblies or complexes thereof provide protection to fully or partially encapsulated drugs and therapeutic bioactive agents in the harsh acidic environment of the stomach. The incorporated drug or agent may be any therapeutically effective agent, such as a natural isolated extracted or synthetic chemical or biological agent including small molecules, oligomers, polymers, proteins, enzymes and peptides. Each possibility represents a separate embodiment of the invention. The "guest" agents can be of various character including highly hydrophobic, amphiphilic or even highly polar and/or charged molecules, which can be of various molecular weights. One compound can be encapsulated, as well as several compounds together. The drugs may be encapsulated in the hydrophobic pocket of the protein assemblies or at the micelle interface.

According to certain embodiments, the mole ratio between the β-casein and the therapeutic agent is at least about 1:10 to about 1:20. Unexpectedly, this mole ratio is maintained when the dried composition is reconstituted in an aqueous solution. Thus, the compositions of the present invention enable administration of adequate amount of the therapeutic agent in therapeutically acceptable dosage units.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 4: (a) SAXS curves of β-casein solutions, obtained for different protein concentrations at pH 2.6 at 4° C. For better visibility, only each fifth experimental point of the scattering curves is shown. The forward scattering intensity was determined by fitting the experimental curves with the IFT routine including desmearing. (b) Aggregation numbers as a function of the concentration, determined from the scattering curves given in a.

DETAILED DESCRIPTION OF SOME EMBODIMENTS

Figure 1:
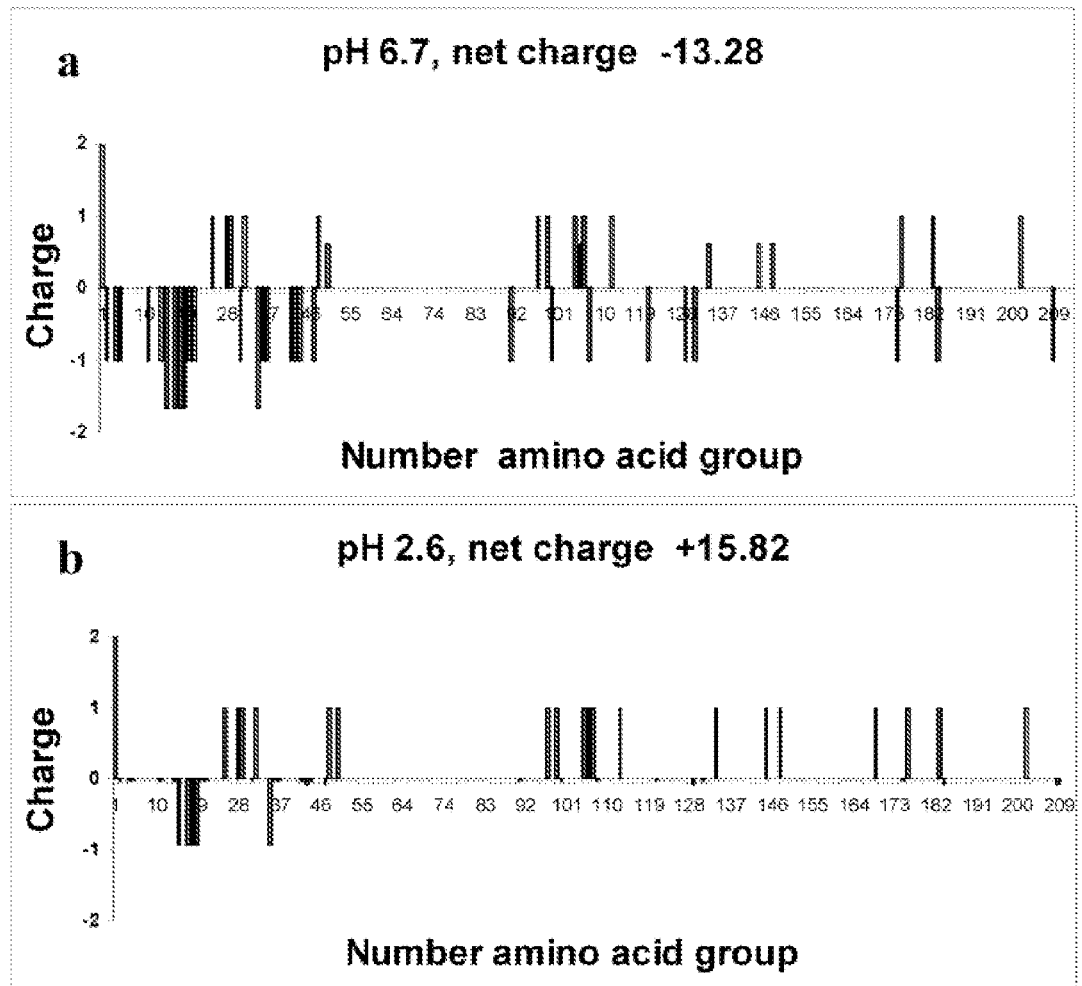
FIG. 1: Distribution of charges along the β-casein backbone at pH 6.7 (panel a) and pH 2.6 (panel b).

The present invention, in at least some embodiments, provides stable dried nanoparticulate β-casein micelles, assemblies or complexes thereof, which are stable at low pH values, as well as at neutral pH. These nano-sized β-casein assemblies are formed at pH values which are typically one or more pH units below the pI of the protein. More typically the β-casein nano-assemblies are formed at low pH, optionally and typically at least one and more typically at least two pH units below the pI of β-casein (pH=5.3). According to at least some other embodiments the β-casein assemblies of the present invention are also formed at neutral pH, typically between pH 6.5-7.5. These carriers formed at both pH values below the pI of β-casein as well as at neutral pH are stable over a wide temperature range (optionally at least from about 1° C. to at least about 45° C.) and for prolonged periods of time (at least 2 weeks to at least 6 months).

According to some embodiments, the present invention features a dried composition comprising micelles, assemblies or complexes thereof formed from isolated β-casein or recombinant β-casein under acid conditions below the pI of β-casein and typically at least one pH unit, more typically at least two pH units, below the pI of the β-casein. The assemblies of the composition typically comprise a majority of β-casein, optionally at least about 70%, typically at least about 80%, more typically at least about 90% and most typically at least about 95% β-casein.

Dried compositions of the invention are obtained according to well established methods known to one of skill in the art. Methods of drying include: air drying, vacuum drying, spray drying, drum drying, and typically freeze drying. Dried compositions of the invention such as but not limited to lyophilized compositions provide the advantage of storage stability.

According to some embodiments, the present invention features a dried composition comprising micelles, assemblies or complexes thereof formed from purified/partially purified β-casein or recombinant β-casein under neutral conditions above the pI of β-casein and typically between about pH 6 and about pH 8.5, more typically between about pH 6.5 and about pH 7.5. The assemblies of the composition typically comprise a majority of β-casein, optionally at least about 70%, typically at least about 80%, more typically at least about 90% and most typically at least about 95% β-casein.

The present invention, in some embodiments, further discloses the use of these micelles, assemblies or complexes thereof as carriers for the loading and stabilizing of bioactive compounds, particularly drugs and therapeutic compounds. Micelles can be loaded, stabilize and carry a broad spectrum of molecules varying in their polarity from highly hydrophobic to highly hydrophilic. This variability allows for very large flexibility and for adapting the details of the formulation for the needs.

The dried loaded compositions of the present invention may be used as pharmaceutical compositions per se or may formulated into tablets or capsules uncoated or coated with an enteric coating. Capsules may be constructed from any suitable enteric polymer, capsules alone or any type of controlled dissolution rate system. For example, the enteric coating optionally and typically comprises at least one enteric material selected from the group consisting of hydroxypropyl methylcellulose acetate succinate (hypromellose acetate succinate), cellulose acetate phthalate, hydroxypropyl methyl cellulose phthalate, polyvinyl acetate phthalate, sodium alginate, alginic acid, poly(methacrylic acid, methyl methacrylate)1:1 and (Eudragit L100), poly(methacrylic acid, ethyl acrylate)1:1 (Eudragit L30D-55). Each possibility represents a separate embodiment of the invention. A suitable enteric coating can be made from e.g. Eudragit™ polymers series (available from Rohm Pharma) which are polymeric lacquer substances based on acrylates and/or methacrylates. Suitable polymers which are slightly permeable to water, and exhibit a pH-dependent permeability include, but are not limited to, Eudragit™ S (poly(methacrylic acid, methyl methacrylate)1:2); Eudragit L100™ (poly(methacrylic acid, methyl methacrylate)1:1); Eudragit L30D™, (poly(methacrylic acid, ethyl acrylate)1:1); and (Eudragit L100-55) (poly(methacrylic acid, ethyl acrylate)1:1). Each possibility represents a separate embodiment of the invention. Eudragit™ L is an anionic polymer synthesized from methacrylic acid and methacrylic acid methyl ester. The permeability of Eudragit™ L is pH dependent. Above pH 5.0, the polymer becomes increasingly permeable. Mixtures of such polymers may also optionally be used.

Alternatively the dried loaded compositions of the present invention can be re-suspended in a solution to afford a suspension for subsequent use. The resuspended solution, unexpectedly, comprises micelles, assemblies or complexes thereof of substantially the same size in comparison to the composition prior to drying. Moreover, the resuspended solution, unexpectedly, comprises micelles, assemblies or complexes thereof of substantially the same size, shape, size distribution, or any combination thereof in comparison to the composition prior to drying. The resuspended solution also, unexpectedly, comprises micelles, assemblies or complexes thereof having substantially equal biological activity in comparison to the composition prior to drying.

In a preferred embodiment, the composition of the invention is freeze dried. In a preferred embodiment, the freeze dried composition is reconstitutible thus maintaing the same particle size range of the composition prior to freeze drying, upon reconstitution. In a preferred embodiment, the freeze dried composition is reconstitutible thus maintaing the same particle size distribution of the composition prior to freeze drying, upon reconstitution. In a preferred embodiment, the freeze dried composition is reconstitutible thus retaining the biological activity of the composition prior to freeze drying, upon reconstitution. In a preferred embodiment, the freeze dried composition is reconstitutible thus retaining the drug load capacity of the composition prior to freeze drying, upon reconstitution. In a preferred embodiment, reconstitution is re-suspending the dried composition in an aqueous solution. In a preferred embodiment, reconstitution is re-suspending the dried composition in a buffer or any other aqueous solution. In another embodiment, re-suspending the dried composition in an aqueous solution results in a suspension. In another embodiment, the suspension of the invention is a pharmaceutical composition comprising a pharmaceutically acceptable carrier. In a preferred embodiment, a suspension results from suspending/reconstituting the dried composition in an aqueous solution.

In one embodiment, the aqueous solution is a pharmaceutical composition. In another embodiment, an aqueous solution is a buffer. In another embodiment, the aqueous solution is an isotonic solution.

In a preferred embodiment, micelles, assemblies or complexes have a diameter of less than 100 nm prior to drying (within the first suspension). In a preferred embodiment, micelles, assemblies or complexes maintain a diameter of less than 100 nm after the dried composition is reconstituted (the second suspension). In a preferred embodiment, micelles, assemblies or complexes within the second suspension (the second suspension results from suspending/reconstituting the dried composition in an aqueous solution) maintain a diameter of less than 100 nm. In a preferred embodiment, micelles, assemblies or complexes have a diameter of less than 50 nm prior to drying (within the first suspension). In a preferred embodiment, micelles, assemblies or complexes maintain a diameter of less than 50 nm after the dried composition is reconstituted (the second suspension). In a preferred embodiment, micelles, assemblies or complexes within the second suspension (the second suspension results from suspending/reconstituting the dried composition in an aqueous solution) maintain a diameter of less than 50 nm.

In one embodiment, a dried composition of the invention comprises less than 15% of water (w/w). In another embodiment, the dried composition comprises from 5% to 15% water (w/w). In another embodiment, the dried composition comprises from 10% to 15% water (w/w). In another embodiment, the dried composition comprises from 12% to 14% water (w/w). In another embodiment, the dried composition comprises from 13% to 15% water (w/w).

The suspension typically comprises between about 0.05% and about 50%, between about 0.2% and about 25%, between about 0.2% and about 10%, between about 0.2% and about 5%, or between about 0.2% and about 2% β-casein of the total composition.

The suspension can be used for administration to a mucosal membrane, locally and/or systemicly to a subject in need thereof.

The suspensions, according to the principles of the present invention can be placed in enteric coated capsules which may optionally be constructed from any suitable enteric polymer, capsules alone or any type of controlled dissolution rate system. For example, the enteric coating optionally and typically comprises at least one enteric material selected from the group consisting of hydroxypropyl methylcellulose acetate succinate (hypromellose acetate succinate), cellulose acetate phthalate, hydroxypropyl methyl cellulose phthalate, polyvinyl acetate phthalate, sodium alginate, alginic acid, poly (methacrylic acid, methyl methacrylate)1:1 and (Eudragit L100), poly(methacrylic acid, ethyl acrylate)1:1 (Eudragit L30D-55). Each possibility represents a separate embodiment of the invention.

A suitable enteric coating can be made from e.g. Eudragit™ polymers series (available from Rohm Pharma) which are polymeric lacquer substances based on acrylates and/or methacrylates. Suitable polymers which are slightly permeable to water, and exhibit a pH-dependent permeability include, but are not limited to, Eudragit™ S (poly(methacrylic acid, methyl methacrylate)1:2); Eudragit L100™ (poly(methacrylic acid, methyl methacrylate)1:1); Eudragit L30D™, (poly(methacrylic acid, ethyl acrylate)1:1), and (Eudragit L100-55) (poly(methacrylic acid, ethyl acrylate)1:1). Each possibility represents a separate embodiment of the invention. Eudragit™ L is an anionic polymer synthesized from methacrylic acid and methacrylic acid methyl ester. The permeability of Eudragit™ L is pH dependent. Above pH 5.0, the polymer becomes increasingly permeable. Mixtures of such polymers may also optionally be used.

Without being bound by any theory or mechanism of action, the polymer coat will help to maintain the intra-capsule composition and pH and therefore the micro-environment of the capsule.

It is expected that when capsules will be dissolved and/or burst and/or disintegrate and/or degraded, the micelles will be adsorbed to the GI tract mucosa according to their electrical charge and the charge of the mucosa (inflamed or non-inflamed). For example in some diseases, surfaces of the GI mucosa are negatively charged and therefore will bind favorably particles having positive charged such as β-casein molecules under acidic pH. In other preferred embodiments, the β-casein molecules are favorably under natural pH conditions.

With regard to other types of tissues and routes of administration, under normal physiological conditions, the pH of plasma and tissues is maintained at values slightly above neutral pH, in a very narrow range of pH values from approximately 7.38 to 7.42. Some pathological conditions may lead to a systemic decrease in pH such as metabolic acidosis which can be caused by diabetic ketoacidosis, alcoholic ketoacidosis, ketoacidosis due to starvation, poisonings (e.g., methanol, ethylene glycol, salicylates, etc.), severe diarrhea, enzyme defect, and the like. All of these conditions can result in a decrease in systemic pH, although not below pH 7.0, even in severe cases. A similar decrease can be observed in respiratory acidosis that can be caused by decreased ventilation, whether acute or chronic.

In addition to disease conditions that result in a systemic decrease in pH, there are many diseases in humans that produce a localized decrease in pH. These conditions include a wide variety of infectious diseases, as well as many tumors which are related to hypermetabolic activity and/or hypoxic state, all of which are capable of inducing the phenomenon of a localized decrease in normal physiological pH. In localized infectious diseases, the pH can be as low as 4.5, whereas in tumor sites, the pH is 0.7 to 1.0 pH unit lower than normal physiological pH.

Without wishing to be limited in any way, it has been demonstrated herein that the β-casein assemblies described herein, when formed in acid aqueous solutions and maintained at a low pH (below the protein pI), have a unique disk-like shape, which has never been previously demonstrated for a self-assembling protein system. This new form of assembly provides the unloaded carrier improved properties over other systems. Among these improved properties and without wishing to be limited by a single hypothesis, the empty or loaded assemblies have been shown to exhibit one or more of the below characteristics: insensitivity of the shape, size or aggregation number to changes in the temperature; stability to changes in pH, within a wide range of acid pH conditions; increased stability to damage or degradation upon storage, namely, longer shelf-life of the unloaded vehicles compared to β-casein micelles at neutral pH. According to some embodiments, the compositions according to the present invention have one or more therapeutic applications, including as a carrier for any type of therapeutic agent as described herein (in some embodiments with the provisos and limitations also as described herein). In particular, the β-casein micelles are advantageously loaded with therapeutic agents having low solubility and/or low-bioavailability to afford compositions which provide improved bioavailability. The drug-loading capacity (i.e. the β-casein to drug mole ratio), according to the principles of the present invention is at least about mole ratios of drug to protein of 1.1 to at least about 1:20. Non limiting examples include at least about 1:2, at least about 1:4, at least about 1:6, at least about 1:8, at least about 1:10, at least about 1:12, at least about 1:14, at least about 1:16 and at least about 1:18. Each possibility represents a separate embodiment of the invention. A non-limiting example of a use of the compositions according to the present invention is for delivery of one or more therapeutic agents to the GI tract for treatment of either local (e.g., inflammatory conditions) or systemic conditions. The present invention may optionally be used, in some embodiments, to treat any GI tract disease. Gastrointestinal diseases and disorders include, without being limited thereto, inflammatory, infectious, gastrointestinal motility disorders, gastroesophageal reflux disease (GERD), chronic intestinal pseudo-obstruction (or colonic pseudo-obstruction, disorders and conditions associated with constipation as well as other conditions known to gastroenterologs. Each possibility represents a separate embodiment of the invention. More specifically, the gastrointestinal diseases and disorders include, without being limited thereto, inflammatory bowel disease (IBD) including ulcerative colitis, Crohn's disease, peptic ulcer disease including gastric ulceration and duodenal ulceration, ileitis, colitis, ileocolitis, ulcerative proctitis, irritable bowel syndrome, gastroenteritis, diverticulitis, diverticulosis, reflux, ulcer, gastritis, dyspepsia, nausea, abrasion to gastrointestinal tract, heart burn, hiatal hernia, gastrointestinal abscess, aralytic ileus and diarrhea, constipation associated with use of opiate pain killers, post-surgical constipation, and constipation associated with neuropathic disorders and combinations thereof. Each possibility represents a separate embodiment of the invention.

The inflammatory condition may optionally comprise any inflammation of the mucosa. Without being bound by any theory or mechanism of action, in case of inflammation, the inflamed areas are selectively positively charged and therefore can be targeted to by anionic particulates such as the β-casein assemblies at neutral pH. (Jubeh, T. T., et al., liposomes. *Pharm. Res.* 21:447-453 (2004); Jubeh, T. T. et al., *Mol. Pharm.* 2, 2-11(2005); Jubeh, T. T. et al., *J. Drug Target* 14, 155-163 (2006); Tirosh, B. et al., *Mol. Pharma.,* 6 (4), 1083-1091, (2009)). The GI mucosa is optionally selected from one or more of intestinal mucosa, small bowel mucosa, large bowel mucosa or the mucosa in the rectum. The term "mucosa" as used herein denotes the moist tissue lining body cavities (such as alimentary canal, nose, lungs, vagina), secretes mucous and covered with epithelium; however for this embodiment, specific reference is made to the intestinal mucosa. Histologically, the intestinal mucosa is divided into three layers: epithelial lining, lamina propria (support), muscularis mucosa (smooth muscle layer). It is supported by the submucosa (a loose collagenous tissue contains blood vessels, lymphatics, & nerves) and the muscularis propria (smooth muscle inner circular layer, outer longitudinal layer).

The inflammatory disease or disorder of the GI mucosa is optionally and typically associated with long term oxidative stress or short term oxidative stress. More typically, the disease or disorder is selected from ulcerative colitis, Crohn's disease, gastric ulceration, duodenal ulceration, ileitis, colitis, ileocolitis, ulcerative proctitis, gastroenteritis, diverticulitis, diverticulosis, reflux, ulcer, gastritis, dyspepsia, nausea, and abrasion to gastrointestinal tract. Each possibility represents a separate embodiment of the invention.

The micelles may optionally be a carrier for a therapeutic agent effective in inhibiting inflammatory responses. The therapeutic agent is more typically selected from steroids, salicylates, COX-2 inhibitors, anti-TNF-α drugs, antibiotics, immunosupressors, immunomodulators and antioxidants. Each possibility represents a separate embodiment of the invention. Most typically, the therapeutic agent is selected from celecoxib, Prednisone, Prednisolone, methylprednisolone, methylprednisolone succinate, Budesonide, derivatives of 5-aminosalicylic acid, Sulfsalazine, Mesalamine (5ASA), Olsalazine, Balsalazide, Metronidazole, Ciprofloxin, Probiotics, Cyclosporin A, Azathioprine, Methotrexate and 6-Mercaptopurine. Each possibility represents a separate embodiment of the invention.

The micelles may optionally, additionally or alternatively, comprise one or more anti-oxidants, including but not limited to tocopherol, free radicals scavengers, SOD and SOD mimics, catalase or therapeutic reducing agents. Each possibility represents a separate embodiment of the invention.

Currently preferred is the loading of the micelles, assemblies and complexes thereof with at least one therapeutic agent selected a peptide, a protein, a hormone and a vitamin. Each possibility represents a separate embodiment of the invention.

For these uses, optionally any of the compositions described herein may be applied, including without limitation compositions prepared at pH values below the pI of the β-casein protein and compositions prepared at neutral pH values. The solubility, stability and bioavailability of the drugs significantly increase upon mixing with the β-casein assemblies of the present invention.

According to some embodiments of the present invention, the loaded β-casein assemblies demonstrate increased solubility of poorly-soluble compounds and/or improved loading of therapeutic molecules into the β-casein micelles. Typically the protein to drug mole ratio will be in the range of about 1:2 to about 1:10 but ratios as high as 1:20 may be achieved.

One of skill in the art can easily calculate the amount of protein required to achieve the desired dosage using mole ratios of at least about 1:1 to at least about 1:20. Typically, the compositions of the present invention comprise ratios of at least 1:2 up to at least about 1:16 protein to drug.

By way of example, initial treatment with budesonide involves daily administration of 0.4- to 1.6 mg of budesonide followed by a maintenance treatment during which a daily dose of 0.2 to 0.4 mg of budesonide is recommended. Based on β-casein to drug mole ratio of about 1 to about 2, about 12 to about 50 mg of β-casein will be needed. A capsule containing 1 ml of 50 mg/ml of β-casein dispersion will suffice to deliver the recommended daily dose of budesonide. Another example is the treatment with celecoxib for which the recommended dose is 75-150 mg once or twice a day. In one embodiment, celecoxib in the micelles, assemblies or complexes is in an amorphous form. An amount of ~200 mg celecoxib in a total of 1 gram (200 mg drug+800 mg protein) provides a β-casein to drug mole ratio of about 1 to about 16. According to some embodiments, the compositions of the present invention comprise between about 70% and about 99% micelles comprising isolated β-casein and between about 1% and about 30% of at least one therapeutic agent.

In some embodiments, celecoxib within the composition of the invention is in an amorphous form. In another embodiment, the composition of the invention stabilizes celecoxib in an amorphous form. In another embodiment, a composition of the invention stabilizing celecoxib in an amorphous form, provides celecoxib with enhanced bioavailability compared to celecoxib in a crystalline form. In another embodiment, a composition of the invention stabilizing celecoxib in an amorphous form enables the utilization of lower dosages of celecoxib for reaching a desired medical effect compared to the crystalline form of celecoxib.

Furthermore, the loaded system may be at least as stable as the unloaded system, or even more stable, and may be stored for the same or longer time period compared to the empty vehicle at the low pH environment or neutral pH. Additionally, the loaded reconstituted system which may be reconstituted at any desirable pH is at least as stable as the unloaded system. The reconstituted systems afford compositions in which the drug dose can be determined according to need.

Some loaded systems according to the present invention remain nanometric in size, transparent or just slightly opalescent. Some guest molecules can further be stabilized in the form of larger complexes in the nano and/or micro range. This is reflected in increased turbidity. The suspensions of many guest molecules remain stable and do not precipitate over time, or as a function of temperature. Some guest molecules (e.g. MPS) may precipitate at low temperature in some formulations according to some embodiments of the present invention, but they are re-solubilized rapidly at room temperature, without loss of bioavailability or loss of activity of the active ingredient.

The β-casein micelles, assemblies or complexes thereof, according to some embodiments of the present invention, are further engineered to load bioactive therapeutic agents, and protect the loaded molecules and stabilize the loaded molecules. The interaction with the vehicle increases the solubility of some poorly-soluble drugs. In currently preferred embodiments, the β-casein micelles, assemblies or complexes thereof are loaded with therapeutic agents that have low solubility and/or low-bioavailability. The dried compositions of the present invention thus provide improved solubility and/or improved bioavailability of the therapeutic agent as compared to its solubility and/or bioavailability with no β-casein being present in the composition.

In some embodiments, the β-casein micelles, assemblies or complexes show an advantageous drug-loading capacity. In particular, the β-casein to drug mole ratio is at least about 1:1 to about 1:20. In some embodiments, the β-casein to drug mole ratio is at least about 1:1 to about 1:10. In additional embodiments, the β-casein to drug mole ratio is at least about 1:10 to about 1:20. Currently preferred is a β-casein to drug mole ratio at least about 1:2 to about 1:16. This unique feature enables the use of a drying method such as but not limited to the freeze dried drug loaded β-casein micelles in conventional drug dosage forms such as tablets and capsules.

The empty carrier and the loaded system are also stable over a wide temperature range, from at least about 1° C., up to over 40° C. The loaded delivery systems are often stable for longer periods than the unloaded systems, in neutral and even in acidic pH. The high stability of the carriers to temperature extremes provides an additional significant advantage, as for many drugs the carrier can be stored for a long time at low temperatures (e.g., 4° C.) then taken orally at ambient temperature. The high stability to such changes in temperature is superior to other existing systems at low pH, as well as to systems at neutral and physiological pH. With some therapeutic agents, precipitation occurs at low temperatures but the re-solubilization occurs within minutes of bringing the system to room temperature, without damage to the therapeutic agent or to bioavailability thereof.

The empty carrier and the loaded system are also stable in a wide ionic strength range from at least about 0.002M to about 0.5M. More typically, from at least about 0.002M to about 0.2M. Even more typically, from at least about 0.002M to about 0.1M.

According to some embodiments of the present invention, the percentage of the β-casein from the total casein content present in the composition is at least about 70%, typically at least about 80%, more typically at least about 90% and most typically at least about 95% of the total protein/casein composition. According to some preferred embodiments the β-casein assemblies of the present invention do not require calcium ions or even exclude calcium atoms. According to the principles of the present invention, calcium ions are not required for holding the micelle structure intact. Without wishing to be bound by any theory or mechanism of action, β-casein micellar compositions of the present invention are not held together by calcium-phosphate bridges.

In a typical embodiment, micelles, assemblies or complexes of the invention are formed in a calcium ions free environment. In a typical embodiment, micelles, assemblies or complexes of the invention are formed without the use of any calcium phosphate. In another embodiment, the formation of micelles, assemblies or complexes does not require nor dependent on calcium ions or calcium phosphate. In another embodiment, the micelles, assemblies or complexes are formed in the absence of calcium ions. In another embodiment, the micelles, assemblies or complexes are formed in the absence of calcium ions. In another embodiment, the micelles, assemblies or complexes are formed in the absence of calcium phosphate. In another embodiment, the dried composition of the invention is free of calcium ions. In another embodiment, the dried composition of the invention is free of calcium phosphate. In another embodiment, the suspension of the invention (comprising dried composition in an aqueous solution) of the invention is free of calcium ions. In another embodiment, the suspension of the invention (comprising dried composition in an aqueous solution) is free of calcium phosphate.

In another embodiment, the micelles, assemblies or complexes are formed in an environment that is essentially devoid of calcium ions and/or calcium phosphate. In another embodiment, the dried composition of the invention is essentialy devoid of calcium ions. In another embodiment, the dried composition of the invention is essentialy devoid of calcium phosphate. In another embodiment, the suspension of the invention (comprising dried composition in an aqueous solution) is essentialy devoid of calcium ions. In another embodiment, the suspension of the invention (comprising dried composition in an aqueous solution) is essentialy devoid of calcium phosphate. In one embodiment, essentially devoid of calcium ions or calcium phosphate means minute amount of calcium ions or calcium phosphate. In one embodiment, essentially devoid of calcium ions or calcium phosphate means less than 100 mM calcium ions or calcium phosphate within the composition or suspension of the invention. In one embodiment, essentially devoid of calcium ions or calcium phosphate means less than 1 mM calcium ions or calcium phosphate within the composition or suspension of the invention. In one embodiment, essentially devoid of calcium ions or calcium phosphate means less than 100 μM calcium ions or calcium phosphate within the composition or suspension of the invention. In one embodiment, essentially devoid of calcium ions or calcium phosphate means less than 1 μM calcium ions or calcium phosphate within the composition or suspension of the invention. In one embodiment, essentially devoid of calcium ions or calcium phosphate means less than 100 nM calcium ions or calcium phosphate within the composition or suspension of the invention. In one embodiment, essentially devoid of calcium ions or calcium phosphate means less than 1 nM calcium ions or calcium phosphate within the composition or suspension of the invention. In one embodiment, essentially devoid of calcium ions or calcium phosphate means less than 100 pM calcium ions or calcium phosphate within the composition or suspension of the invention.

Carrier assemblies as described herein according to some embodiments of the present invention are therefore surprisingly useful for a wide range of classes of drugs which suffer from poor oral or other mucosal membrane absorption, and hence bioavailability, which severely limits their applicability, usage and effectiveness. Such therapeutic agents (also referred to herein as active ingredients) may optionally comprise any type of bulky, large, hydrophobic, insoluble in an aqueous solution and/or at body pH values, and/or pH sensitive material, including without limitation plant alkaloids and the like, drugs with multi-cyclic ring structures (including those that lack polar groups), peptides and proteins, including antibodies and enzymes, or any type of biopolymer, including without limitation oligonucleotides and polynucleotides (including without limitation siRNA molecules and the like). Each possibility represents a separate embodiment of the invention. According to currently preferred embodiments, the agents do not comprise a chemotherapeutic drug, which is any drug having high systemic toxicity for treatment of cancer.

Non-limiting examples of such classes of drugs include non-steroidal anti-inflammatory drugs (N SAID) such as COX-2 inhibitors, ibuprofen, naproxen, diclofenac, indomethacin, piroxicam, etc., anti-resorptive agents such as bisphosphonates, steroids including corticosteroids, antivirals (acyclovir, IUdR, ganciclovir, vidarabine, AZT), steroidal anti-inflammatory drugs (dexamethasone, loteprednol, prednisolone derivatives, etc.), antibiotics (e.g., ampicillin and erythromycin), antifungals (e.g., miconazole), hormones, local anesthetics, analgesics, calcium channel blockers (e.g., Verapamil), prostaglandins and prostacyclins, cholinergics, adrenergic antagonists, anticonvulsants (e.g., phenyloin), antianxiety agents, major tranquilizers, antidepressants, anabolic steroids, estrogens, progesterones, immune suppressants such as cyclosporine, glycosaminoglycans (heparin, heparan, chondroitin sulfate, and low molecular weight derivatives thereof); any type of fluorescent dye, including but not limited to cyanines, indocyanines, or squaraines; antihelminthics, anti-arrhythmic agents, antibacterial agents, anti-viral agents, anti-coagulants, anti-diabetics, anti-gout agents, anti-hypertensive agents, anti-malarials, anti-migraine agents, anti-muscarinic agents, anti-neoplastic agents, erectile dysfunction improvement agents, immunosuppressants, anti-protozoal agents, anti-thyroid agents, anxiolytic agents, sedatives, hypnotics, neuroleptics, beta-blockers, cardiac inotropic agents, corticosteroids, diuretics, anti-Parkinsonian agents, gastro-intestinal agents, histamine receptor antagonists, keratolyptics, lipid regulating agents, anti-anginal agents, leukotriene inhibitors, macrolides, muscle relaxants, nutritional agents, opioid analgesics, protease inhibitors, sex hormones, stimulants, muscle relaxants, anti-osteoporosis agents, anti-obesity agents, cognition enhancers, anti-urinary incontinence agents, anti-benign prostate hypertrophy agents, essential fatty acids, non-essential fatty acids; and combinations thereof, or derivative or salt thereof. Each possibility represents a separate embodiment of the invention.

In addition to the above listed therapeutic agents, specific examples of therapeutic agents may optionally comprise one or more of acetretin, albendazole, albuterol, aminoglutethimide, amiodarone, amlodipine, amphetamine, amphotericin B, atorvastatin, atovaquone, azithromycin, baclofen, beclomethasone, benezepril, benzonatate, betamethasone, bicalutanide, budesonide, bupropion, busulfan, butenafine, calcifediol, calcipotriene, calcitriol, camptothecin, candesartan, capsaicin, carbamezepine, carotenes, celecoxib, cerivastatin, cetirizine, chlorpheniramine, cholecalciferol, cilostazol, cimetidine, cinnarizine, ciprofloxacin, cisapride, clarithromycin, clemastine, clomiphene, clomipramine, clopidogrel, codeine, coenzyme Q10, cyclobenzaprine, cyclosporin, danazol, dantrolene, dexchlorpheniramine, diclofenac, dicoumarol, digoxin, dehydroepiandrosterone, dihydroergotamine, dihydrotachysterol, dirithromycin, donezepil, efavirenz, eprosartan, ergocalciferol, ergotamine, etodolac, etoposide, famotidine, fenofibrate, fentanyl, fexofenadine, finasteride, fluconazole, flurbiprofen, fluvastatin, fosphenyloin, frovatriptan, furazolidoneu, gabapentin, gemfibrozil, glibenclamide, glipizide, glyburide, glimepiride, griseofulvin, halofantrine, ibuprofen, irbesartan, irinotecan, isosorbide dinitrate, isotretinoin, itraconazole, ivermectin, ketoconazole, ketorolac, lamotrigine, lansoprazole, leflunomide, lisinopril, loperamide, loratadine, lovastatin, L-thryroxine, lutein, lycopene, medroxyprogesterone, mifepristone, mefloquine, megestrol acetate, methadone, methoxsalen, metronidazole, miconazole, midazolam, miglitol, minoxidil, montelukast, nabumetone, nalbuphine, naratriptan, nelfmavir, nifedipine, nilsolidipine, nilutanide, nitrofurantoin, nizatidine, omeprazole, oprevelkin, oestradiol, oxaprozin, paclitaxel, paracalcitol, paroxetine, pentazocine, pioglitazone, pizofetin, pravastatin, prednisolone, probucol, progesterone, pseudoephedrine, pyridostigmine, rabeprazole, raloxifene, rofecoxib, repaglinide, rifabutine, rifapentine, rimexolone, ritanovir, rizatriptan, rosiglitazone, saquinavir, sertraline, sibutramine, sildenafil citrate, simvastatin, sirolimus, sodium clodronate, spironolactone, sumatriptan, tacrine, tacrolimus, tamsulosin, targretin, tazarotene, telmisartan, teniposide, terbinafine, terazosin, tetrahydrocannabinol, tiagabine, ticlopidine, tirofibran, tizanidine, topiramate, topotecan, toremitfene, tramadol, tretinoin, troglitazone, trovafloxacin, ubidecarenone, valsartan, venlafaxine, verteporfin, vigabatrin, zafirlukast, zileuton, zolmitriptan, zolpidem, zopiclone, pharmaceutically acceptable salts, isomers, and derivatives thereof, and combinations thereof. Each possibility represents a separate embodiment of the invention.

In some embodiments, therapeutic agents are peptides, proteins, hormones, or vitamins. In another embodiment, the therapeutic agent is a low molecular weight (<1000 Da) molecule. Each possibility represents a separate embodiment of the invention.

The above description notwithstanding, according to some embodiments of the present invention, the therapeutic agent does not comprise a chemotherapeutic drug as defined above.

However, according to some embodiments of the present invention, the therapeutic agent is a chemotherapeutic drug. A chemotherapeutic agent in some embodiments is an agent used to treat cancer. In some embodiments, an anti-cancer chemotherapeutic drug is associated with severe side effects and toxicity, most of which is dose dependent. Most anti-infectious agents also demonstrate dose-dependent adverse side effects and toxicity. Therefore, it would be advantageous to be able to reduce these adverse effects by the use of a drug carrier that imparts reduced toxicity to therapeutically active systems. Alternatively, it would also be advantageous to reduce the overall toxic effects of therapeutic agents on a patient's system through minimization of the delivery of the therapeutic, and therefore toxic, component of treatment agents to clinically irrelevant tissue sites.

Non-limiting examples of suitable chemotherapeutic drugs include a taxane (e.g., paclitaxel), vincristine and other vinca alkaloids (e.g., vinblastine), anthracyclines (e.g., doxorubicin, daunorubicin), epipodophyllotoxins (e.g., etoposide), actinomycin D, actinomycin D, dolastatin 10, colchicine, emetine, trimetrexate, metoprine, cyclosporine, teniposide, amphotericin, alkylating agents (e.g., chlorambucil), 5-fluorouracil, camptothecins (e.g. topotecan), cisplatin and carboplatin, metronidazole, Abarelix, aldesleukin, Aldesleukin, Alemtuzumab, Alitretinoin, Allopurinol, Altretamine, Amifostine, Anastrozole, Arsenic trioxide, Asparaginase, Azacitidine, BCG Live, Bevacuzimab, Avastin, Fluorouracil, Bexarotene, Bleomycin, Bortezomib, Busulfan, Calusterone, Capecitabine, Camptothecin, Carmustine, Celecoxib, Cetuximab, Chlorambucil, Cladribine, Clofarabine, Cyclophosphamide, Cytarabine, Dactinomycin, Darbepoetin α, Daunorubicin, Denileukin, Dexrazoxane, Docetaxel, Doxorubicin (neutral), Doxorubicin hydrochloride, Dromostanolone Propionate, Epirubicin, Epoetin α, Erlotinib, Estramustine, Etoposide Phosphate, Etoposide, Exemestane, Filgrastim, floxuridine fludarabine, Fulvestrant, Gefitinib, Gemcitabine, Gemtuzumab, Goserelin Acetate, Histrelin Acetate, Hydroxyurea, Ibritumomab, Idarubicin, Ifosfamide, Imatinib Mesylate, Interferon α-2a, Interferon α-2b, hrinotecan, Lenalidomide, Letrozole, Leucovorin, Leuproli de Acetate, Levami sole, Lomustine, Megestrol Acetate, Melphalan, Mercaptopurine, 6-MP, Mesna, Methotrexate, Methoxsalen, Mitomycin C, Mitotane, Mitoxantrone, Nandrolone, Nelarabine, Nofetumomab, Oprelvekin, Oxaliplatin, Paclitaxel, Palifermin, Pamidronate, Pegademase, Pegaspargase, Pegfilgrastim, Pemetrexed Disodium, Pentostatin, Pipobroman, Plicamycin, Porfimer Sodium, Procarbazine, Quinacrine, Rasburicase, Rituximab, Sargramostim, Sorafenib, Streptozocin, Sunitinib Maleate, Talc, Tamoxifen, Temozolomide, Teniposide, VM-26, Testolactone, Thioguanine, 6-TG, Thiotepa, Topotecan, Toremifene, Tositumomab, Trastuzumab, Tretinoin, ATRA, Uracil Mustard, Valrubicin, Vinblastine, Vincristine, Vinorelbine, Zoledronate, or Zoledronic acid, or combinations or derivative or salt thereof. Each possibility represents a separate embodiment of the invention.

However, it should be noted that according to some embodiments, chemotherapeutic drugs are specifically not encompassed within the formulations or compositions of the present invention, such that any of the embodiments described herein may optionally have the proviso that the therapeutic agent does not comprise a chemotherapeutic drug, and more specifically, that the therapeutic agent does not comprise methotrexate or mitoxantrone. Optionally and more typically, for those embodiments which encompass chemotherapeutic drugs, the micelles are limited to a size in a range below about 300 nm, even more typically below about 200 nm and most typically below about 100 nm in diameter. Typically, in other embodiments, the micelles are limited to a size in a range below about 75 nm, even more typically below about 50 nm and most typically below about 40 nm in diameter In terms of selecting the appropriate amount of therapeutic agent to be carried by the micelles (for example contained within, surrounded by and so forth), the amount is typically effective to treat or prevent any of the conditions, diseases or disorders described herein as appropriate. An amount being effective to provide the desired effect can be readily determined, in accordance with the invention, by administering to a plurality of tested subjects various amounts of the therapeutic loaded onto the micelles and then plotting the physiological response (for example an integrated "SS index" combining several of the therapeutically beneficial effects) as a function of the amount of loaded therapeutic agent. Alternatively, the effective amount may also be determined, at times, through experiments performed in appropriate animal models and then extrapolating to human beings using one of a plurality of conversion methods. As known, the effective amount may depend on a variety of factors such as mode of administration, the age, weight, body surface area, gender, health condition and genetic factors of the subject; other administered drugs; etc. In some exemplary embodiments, the dried compositions of the present invention comprise between about 70% and about 99% micelles comprising isolated β-casein and between about 1% and about 30% of at least one therapeutic agent.

The assemblies of the present invention can be prepared by adding the drug solubilized in a solvent or co-solvent, e.g., ethanol or DMSO, to the β-casein assemblies or micelles at acidic or neutral pH followed by stirring. Typically the amount of solvent present while preparing the composition is between about 0.05% and about 20% of the total composition. More typically, between about 0.1% and about 10% of the total composition. Even more typically, between about 0.1% and about 8% of the total composition. Yet even more typically, between about 0.1% and about 5% of the total composition. Alternatively, the assemblies of the present invention can be prepared by dry mixing the drug and β-casein, and then adding the dry mixture to a buffer whereas the buffer is an acidic buffer or a neutral buffer. This procedure avoids the addition of solvent.

It is to be explicitly understood that within the scope of the present invention, the compositions may comprise more than one therapeutic agent. For example, each of the therapeutic agents may be mixed with ethanol and then combined with the β-casein assemblies or micelles at acidic or neutral pH. In alternative embodiments, two or more different therapeutic agents may be combined within a single β-casein assembly or micelle. In alternative embodiments, two or more therapeutic agents may be individually combined with the β-casein assemblies or micelles and then combined together. In alternative embodiments two or more therapeutic agents may be dry mixed with β-casein powder and then added to an aqueous solution of acidic or neutral pH. The oral delivery system may optionally be taken in a liquid form, or the liquid system can be further encapsulated within suitable capsules or coated to allow simple oral use, using methods well known in the art of pharmaceutical science.

β-casein constitutes about 38% of the casein in bovine milk. Its primary structure is composed of 209 amino acids, and its molecular mass is 23,946 to 24,097 Da (depending on the genetic variant). It is the most hydrophobic casein because of its large hydrophobic C-terminal domain (based on its primary structure). However, its highly charged N-terminal domain, containing the phosphate center, makes it very amphipathic. The pronounced amphiphilic structure of β-casein imparts many properties resembling those of low molecular weight surfactants. Thus, the protein tends to self-assemble under appropriate conditions into well-defined micelles of about 15 to about 60 molecules with a critical micelle concentration (CMC) in the range of about 0.05-0.2%, depending on temperature, pH, solvent composition and ionic strength (Portnaya I. et al. 2006, *J. Agric. Food Chem.* 54; 5555-61).

The critical micelle concentration (CMC) is defined as the concentration of surfactant (in this case, the β-casein protein) above which micelles are spontaneously formed. Upon introduction of the protein into the system (such as for example the compositions described herein), the protein will initially partition into the interface, reducing the system free energy by a) lowering the energy of the interface (calculated as area× surface tension) and b) by removing the hydrophobic parts of the protein from contacts with water. Subsequently, when the surface coverage increases and the surface free energy (surface tension) has decreased, the amphiphilic protein starts aggregating into micelles, thus again decreasing the system free energy by decreasing the contact area of hydrophobic parts of the protein with water. Upon reaching CMC, any further addition of amphiphilic protein typically increases the number of micelles.

These characteristics give micelles composed of at least a majority of β-casein proteins an advantage over the prior art casein micelles which size distribution cannot be controlled to this extent (typical sizes are 50-500 nm in diameter, such that their heterogeneity is large, and encapsulation is likely restricted, while the current micelles have a diameter of less than 50 nm or even less than 40 nm.

According to at least some embodiments, the micelles of the present invention have a diameter of optionally below about 300 nm, typically below about 200 nm, more typically below about 100 nm, or most typically below about 50 nm.

According to some embodiment of the present invention, the composition comprises micelles comprising isolated β-casein, wherein the isolated β-casein of the micelles is at least about 70% wt/wt of the total casein, wherein the micelles have a diameter of optionally below about 300 nm, typically below about 200 nm, more typically below about 100 nm, or most typically below about 50 nm.

The present invention, in at least some embodiments, overcomes precipitation of β-casein by typically preparing the micelles at a pH value that is at least about one unit, and more typically at least about two units, still more typically more than two pH units below the pI of β-casein. According to some embodiments of the present invention, the process for preparation of the micelles involves directly introducing the dry β-casein into a pH at least one or at least two or more pH units below the pI rather than gradual reduction in pH thus avoiding precipitation at pH values close to the pI of the β-casein.

The present invention, in at least some embodiments, overcomes precipitation of β-casein by typically preparing the micelles at a neutral pH value. According to some embodiments of the present invention, the process for preparation of the micelles involves directly introducing the dry β-casein into neutral pH thus avoiding precipitation at pH values close to the pI of the β-casein The dried compositions of the present invention are dried or lyophilized using any of the methods known in the art. As contemplated herein, the process of lyophilization may be performed from a neutral or from an acidic pH. The dried assemblies may conveniently be used as pharmaceutical compositions per se or may be reconstituted in a suitable liquid medium prior to use. The reconstitution may be performed using a solution in any desired pH including acidic, neutral or basic pH. The re-constituted compositions, according to the principles of the present invention, are in the form of solutions or suspensions. Thus, according to additional embodiments, the present invention provides a suspension comprising the dried composition as disclosed herein above. In some embodiments, the suspension comprises between about 0.05% and about 50% β-casein of the total composition. More typically, the amount of β-casein present in the suspension is between about 0.2% and about 25% of the total composition. Even more typically, the amount of β-casein present in the suspension is between about 0.2% and about 10% of the total composition. Still more typically, the amount of β-casein present in the suspension is between about 0.2% and about 5% of the total composition. Yet still more typically, the amount of β-casein present in the suspension is between about 0.2% and about 2% of the total composition.

In yet other embodiments, the present invention provides the use of the dried composition of the present invention for the preparation of a suspension suitable for administration to a mucosal membrane. In another embodiment, the present invention provides the use of the dried composition of the present invention for treatment of local and/or systemic conditions, typically an inflammatory condition. In additional embodiments, the present invention provides a method of treating a local and/or systemic condition comprising administering to a subject in need thereof a suspension comprising the dried composition as disclosed herein.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

Materials and Methods
Cryo-TEM:

Specimens were prepared either in an automated vitrification device (Vitrobot, FEI, The Netherlands) or in the controlled environment vitrification system (CEVS) (Bellare et al. *Electron Microsc. Technique,* 1988, 10; 87-111) at 24° C. and 100% relative humidity to avoid loss of volatiles. Using the latter, the solutions were incubated in the CEVS at the desired temperature for 1 h. Then, a 7 µL drop of each solution was placed on a TEM copper grid covered with a perforated carbon film (Pelco International) and blotted with filter paper to form a thin liquid film of the sample (100-200 nm thick). The thinned sample was plunged into liquid ethane at its freezing temperature (−183° C.) to form a vitrified specimen and then transferred to liquid nitrogen (196° C.) for storage. Some of the vitrified specimens were examined in a Philips CM120 transmission electron microscope. (Philips, The Netherlands) operating at an accelerating voltage of 120 kV. An Oxford CT3500 (Oxford Instruments) cryo-specimen holder that maintained the specimens below −175° C. during sample transfer and observation Other specimens were examined in a Tecnai 12 G2 TEM (FEI) using a Gatan 626 cryo-holder. Specimens were studied in a low-dose imaging mode to minimize beam exposure and electron beam radiation damage.

Images were recorded digitally on a cooled Gatan Multi-Scan 791 CCD camera using DigitalMicrograph 3.1 software (Gatan) in the low-dose imaging mode to minimize beam exposure and electron-beam radiation damage. Alternatively, images were recorded in the Tecnai on a high-resolution 2 k×2 k Ultrascan 1000 cooled CCD (Gatan, UK), using the Digital Micrograph 3.6 software (Gatan, UK).

Turbidity:

Turbidity measurements were performed using an Amersham Biosciences Ultrospec 2100 pro spectrophotometer at a wavelength of 600 nm.

Size Distribution Analysis and Particle Electrostatics:

DLS and Zeta potential measurements performed on a combined DLS and zeta potential analyzer (Nicomp 380 ZLS zeta potential/particle sizer, USA), at 25° C. were performed for size distribution and electrostatics characterization. For DLS measurements the scattered light intensity was detected with an Avalanche Photo Diode (APD) detector, used at a fixed angle of 90°. Laser wavelength was 658 nm, operating at 90 mW. Mono- bi- or tri-modal distributions were calculated from the scattered light intensity fluctuations, by Nicomp™ cumulants analysis of the intensity autocorrelation function. Zeta potential measurements were performed in triplicate.

Light Microscopy:

An Olympus BX51 light microscope was operated at Nomarski differential interference contrast (DIC) optics. A 5 µL drop was placed on a glass slide, covered with a cover slide. Images were recorded digitally with an Olympus DP71 digital camera connected to the light microscope. Image processing was performed using Cell A (Olympus).

Wide-Angle X-Ray Diffraction (XRD):

XRD experiments with crystalline celecoxib or lyophilized drug and/or protein/drug samples were performed by a Philips PW 3020 powder diffractometer equipped with a graphite crystal monochromator (Philips). The operating conditions were CuKα radiation (0.154 nm), voltage 40 kV and current 40 mA, in 2θ recording range from 3° to 65°, at room temperature.

Isothermal Titration Calorimetry (ITC):

ITC measurements were performed with a VP-ITC calorimeter (MicroCal) at a temperature of 24° C. The reaction cell (V=1.43 mL) was filled with degassed solvent (lactic acid at pH 2.6, or phosphate buffer at pH 7.0). The injector-stirrer syringe (289 µL) was loaded with a β-casein micellar solution (20 mg/mL). The micellar solution was injected into the reaction cell in 28 steps of 10 µL aliquots each, and the heat flow was measured. During the titration, the stirring speed was 310 rpm. The duration of each injection was 20 s, and the equilibration time between consecutive injections was 3 min. Such an interval was sufficient to equilibrate the reaction cell after every injection. Each experiment was performed at least three times. Calorimetric data analysis was carried out using Origin 5.0 software (MicroCal).

Analytical Ultracentrifugation:

Sedimentation equilibrium experiments were performed at 24° C. using a Beckman Optima XL-A (Palo Alto, Calif.) analytical centrifuge at 6,000, 10,000, and 12,000 rpm for the low-pH solutions and at 4,000, 6,000, and 8,000 rpm for the pH 7.0 solutions. Data were collected at 280 nm. The β-casein solutions were studied at concentrations ranging from 0.2 to 10.0 mg/mL at pH 2.6 and from 0.2 to 2 mg/mL at pH 7.0 and an ionic strength of 0.1. Past studies showed that the protein self-assembly is not affected by pressure and, therefore, it is not speed-dependent. The average apparent molecular weight of the micelles at the various protein concentrations was calculated following methods well known in the art (The partial specific volume vj of the solute was taken to be 0.742 $cm^3/g^3$, and a solution density F of 1.0044 $g/cm^3$ was measured). At β-casein concentrations of 2 mg/mL and above under low pH conditions, the plot of the natural logarithm of the measured absorbance versus the square of the radius from the axis of rotation was not linear. To estimate Nagg, the limiting slope toward the outer edge of the sample cell was used to provide d ln(c)/dr$^2$. The molecular weight calculated using this slope was divided by the monomer molecular weight calculated from the β-casein amino acid sequence (24,000).

Small Angle X-Ray Scattering (SAXS):

The small angle X-ray scattering equipment consisted of a SAXSess camera (Anton-Paar, Graz, Austria) connected to an X-ray generator (Philips, PW 1730/10) operating at 40 kV and 50 mA with a sealed-tube Cu anode. A Gael mirror was used to convert the divergent polychromatic X-ray beam into a focused line-shaped beam of Cu Kα radiation (λ=0.154 nm). The 2D scattering pattern was recorded by a PI-SCX fused fiber optic taper CCD camera from Princeton Instruments, which is a division of Roper Scientific, Inc. (Trenton, N.J., USA). The used CCD detector features a 2084×2084 array with 24×24 µm pixel size (chip size: 50×50 mm). The CCD was operated at −30° C. with 10° C. water-assisted cooling to reduce the thermally generated charge. Cosmic ray correction and background subtraction were performed on the 2D image before further data processing. The 2D image was integrated into the one-dimensional scattering function within a band of 10 mm. The measurement time was 30 min for each scattering curve (6 images of 5 minutes were taken to assist the cosmic ray correction).

Density Measurements.

The specific gravity of the solvents and the protein solutions was measured by a density meter DMA 5000 from Anton-Paar at various temperatures. These measurements enabled an accuracy of six digits.

Determination of the β-Casein Assemblies Molecular Weights.

The molecular weight of the scattering aggregates were calculated according to Eq. 1:

$$M = \frac{d\Sigma(0)}{d\Omega}(N_A/c\Delta\rho_M^2) \quad (1)$$

where M is the molecular weight, $d\Sigma(0)/d\Omega$ (cm$^{-1}$) the forward scattering intensity at q=0, c (g/cm$^3$) the β-casein concentration, $N_A$ the Avogadro number, and $\Delta\rho_M$ (cm/g) the scattering length difference per mass, given by:

$$\Delta\rho_M = \Delta\rho\bar{v} \quad (2)$$

The scattering length difference $\Delta\rho$ (cm$^{-2}$) was calculated using the known chemical composition of the protein and the solvent, and $\bar{v}$ (cm$^3$/g), the specific volume of the protein in the solution that was calculated via density measurement of the solvent and the solution. The micelle aggregation number was then calculated by dividing the molecular weight of the micelles determined with Eq. 1, by the molecular weight of a single protein molecule.

PDDF Determination.

For a particle of arbitrary shape with a scattering density difference of $\Delta\rho(r)$, the pair distance distribution function p(r) (PDDF) is given by:

$$p(r) = r^2 \overline{\Delta\rho^2}(r) \quad (3)$$

where $\overline{\Delta\rho^2}(r)$ is the convolution square of $\Delta\rho(r)$ averaged for all directions in space. The PDDF is related to the scattered intensity I(q) by a Fourier transformation, and it enables the determination of the overall shape and size of the scattering objects.

$$I(q) = 4\pi \int_0^\infty p(r) \frac{\sin(qr)}{qr} dr \quad (4)$$

where q is the magnitude of the scattering vector q, defined as $$q = \frac{4\pi}{\lambda}\sin\left(\frac{\theta}{2}\right) \quad (5)$$

λ is the wavelength of the incident radiation and θ is the angle between the scattered and incident beam. The function $$f(r) = p(r)/r \quad (6)$$

is useful to identify flat plate-like particles, although it has no direct physical meaning. For lamellae, this function starts with a linearly increasing part and becomes almost flat when r is equal to the thickness of the lamella. For flat particles with a finite base area, the outer part decreases linearly because of boundary losses. The thickness of the lamella can then be read from the transition point. Hence, in practice, the shape of the function $f(r)$ allows the recognition of lamellar particles and determination of their thickness.

Statistical Analysis:

For each of the methods applied, a statistical analysis of the data was performed, based on at least three separate replicate experiments. The standard error of the ITC data was found to be no more than 5% for the CMC and MR values and no more than 3% for ΔHdemic. The standard error of the analytical ultracentrifugation data is 5%, and that of the Rg is 4%. The analysis supports the statistical significance and validity of the results.

EXAMPLE 1

Preparation of β-Casein Assemblies

Weighted amounts of lyophilized bovine β-casein are dissolved in low-pH solution (e.g. ~6% by weight of lactic acid solution or hydrochloride acid solution, ~pH 2.1), typically at concentrations ranging from 0.1 mg/mL up to at least 50 mg/ml, to the desired pH (2.3-2.8), below the pI. The pH can be adjusted to the desired values using appropriate buffers. Mixing is performed at room temperatures, and the solution is equilibrated at 4° C. for ~36 hr, allowing complete solubilization and formation of the protein assemblies. Thereafter, the solutions can be held at any temperature between 1 and 60° C.

Similarly, to prepare β-casein micelles at neutral pH, weighted amounts of lyophilized protein were added to a buffer at neutral pH (e.g., hepes buffer, or PBS, or histidine buffer), at concentration ranging from 0.1 mg/ml to ~50 mg/ml.

Complete solubilization of the protein is achieved within about 1 hr to about 36 hr, at temperatures ranging from 4° C. to about 40° C. A transparent solution is obtained, containing nano-sized β-casein assemblies. The protein solutions are filtered through a porous membrane of 0.45 micron pore size. The β-casein concentration was determined by measuring the absorbance at 280 nm by an Ultrospec 2000 UV/Visible spectrophotometer (Pharmacia Biotech, England), using an extinction coefficient of 4.6 (1%) mM$^{-1}$ cm$^{-1}$. Other methods to determine protein concentration such as Lowry can also be used. The stock solution is diluted with an acidic/neutral solution having the same pH, to the final concentration required, typically between 0.1 mg/ml and 20 mg/ml. The ionic strength and Osmolarity can be adjusted by mixing the vehicles-containing solution with a salt-containing electrolyte (or without salt) solution, both having the same pH. The solution can be stored at 4° C., for at least several weeks, more specifically for at least 3 weeks typically at least 1 month, depending on the storage medium pH, ionic strength, and osmolarity.

The low and neutral pH β-casein assemblies of the present invention have been characterized by various techniques including: isothermal titration calorimetry (ITC), small-angle x-ray scattering (SAXS), analytical ultracentrifugation, density measurements and cryogenic-transmission electron microscopy (cryo-TEM).

EXAMPLE 2

Density Measurements of β-Casein Solutions

Density measurements of the β-casein solutions at pH 2.6 as a function of temperature are summarized in Table 1 Density measurements were performed using a density meter DMA 5000 from Anton-Paar, reaching an accuracy of six digits.

TABLE 1

Density measurements of β-casein solutions, as a function of temperature, measured at pH 2.6.

| T [° C.] | Data of 20 mg/ml β-casein pH 2.6, lactic acid solution | | | |
|---|---|---|---|---|
|  | 4 | 16 | 25 | 40 |
| Solvent density [g/cm$^3$] | 1.005274 | 1.003948 | 1.001878 | 0.996814 |
| Solution density [g/cm$^3$] | 1.010410 | 1.008926 | 1.006764 | 1.001588 |

EXAMPLE 3

β-Casein Charge Distribution

The distribution of charges along the β-casein backbone and the β-casein protein total charge at acidic and neutral pHs were calculated. FIG. 1 shows the protein sequence and distribution of charges at the two pH regimes. At pH 6.7, most charges are concentrated at the N-terminus, while the long C-terminus is highly hydrophobic. A net charge of −13.28 was calculated at this pH, in good agreement with previous calculations at similar pH values. At a low pH of 2.6, the protein net charge is somewhat larger (+15.82 vs −13.28). The charge distribution, however, changes significantly. A cluster of negative charges is present in sequences 15-20. Sequences 25-50 contain a cluster of six positive charges and sequences 97-113 contain another cluster of six charges, while the domain in between does not have any charge. Additionally, a large number of positive charges are distributed along the hydrophobic C-terminus. Thus, overall, this picture indicates that in an acidic environment, the protein loses the distinct separation between hydrophilic and hydrophobic domains.

EXAMPLE 4

Characterization of the β-Casein Micelles by Cryo-TEM and SAXS

The structural characteristics of the micelles in the two pH environments were studied by cryo-TEM and SAXS (Small Angle X-ray Scattering). Cryo-TEM was used to determine the shape of the micelles and to estimate their dimensions between 4 and 40° C. This information was further used to accurately calculate the micelles' dimensions from the SAXS data, and to study how the size and shape are affected by temperature. SAXS measurements also provided the critical micelle concentration (CMC) and the micelle aggregation numbers as a function of temperature. Experiments were performed in the concentration range of 0.1-40 mg/mL protein, at low pH (between 2.1 and 2.6) in dilute lactic acid solution (6 wt %) or HCl and in aqueous solutions at pH 6.7-7.3 in absence of salts or the presence of up to 0.1M NaCl.

Figure 2:
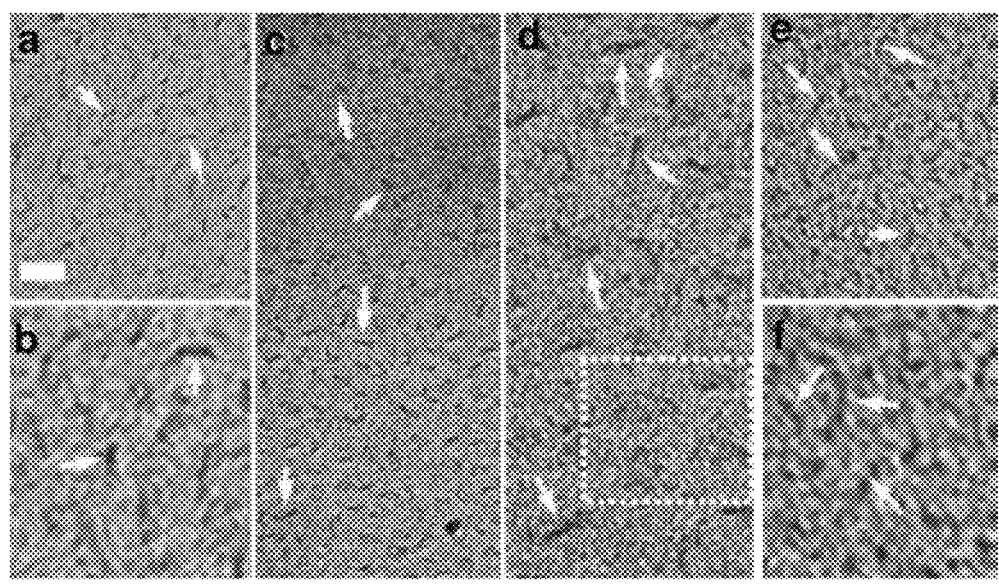
FIG. 2: Cryo-TEM images of 2 wt % β-casein micelles in lactic acid solution (pH 2.6): (panels a and b) 40° C., (panels c and d) 25° C., (panels e and f) 4° C. Panels a, c and e show low magnification regions populated with the protein micelles. Higher magnifications of these structures are given in panels b, d and f. All images show flat disc-like (plate-like) micelles. Due to the relatively low contrast of the thin micelles they are best seen when their flat surfaces are positioned parallel to the electron beam. In very thin specimens (e.g., image d) less structures and solvent (per unit volume) contribute to the 2-dimensional image, thus the micelles look more spaced, and additionally, micelles oriented with their flat surface perpendicular to the electron beam are also resolved (see, for example, the upper part of panel c, and the micelles enclosed in the dashed square in panel d). Arrows in the images point to few disc micelles, showing they have similar thickness and length under all the temperatures studied. Bar equals 50 nm (a, c and e) and 20 nm (b, d and f).

In the lactic acid solution (pH 2.6), flat disk-like micelles formed within the complete temperature range studied (4-40° C.), as shown in the cryo-TEM images presented in FIG. 2. From the 2-D projection of the micelles in the vitrified samples, the micelles are estimated to be 3-4 nm thick and to have elongated surfaces 20-25 nm in length. Micelles of similar shape and dimensions also form in HCl at the same pH at room temperature. This suggests that under the conditions studied, the nature of the solvent's counterion has little, if any, effect on the size, shape, and dimensions of the β-casein containing micelles. Overall, the cryo-TEM experiments show that at low pH, β-casein self-organizes into a homogeneous population of flat, disk-like micelles, whose shape and dimensions appear to be independent of the solvent counterion or the solution temperature.

The self-assembly behavior of the solution of 20 mg/mL β-casein at pH 6.7 and 0.05M NaCl was studied as a function of temperature. Flat micelles were observed at 4° C. and 10° C., but their contrast is relatively low, and consequently, their morphology is somewhat indistinct. At 16, 25, and 40° C., oblate micelles were detected. Relatively spheroidal micelles were found at the high temperature of 60° C.

EXAMPLE 5

Characterization of the β-Casein Micelles by SAXS

Figure 3A:
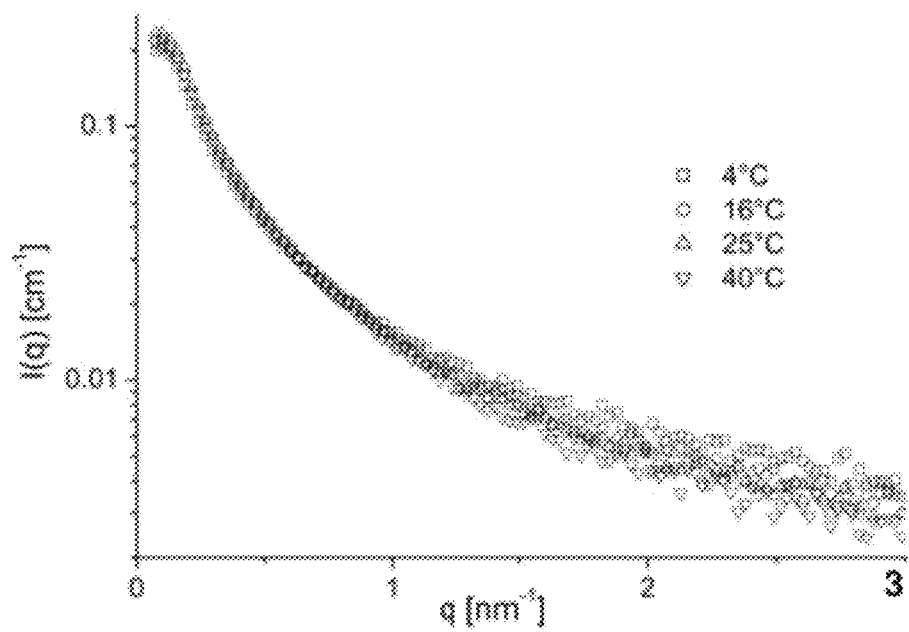
FIG. 3: (a) SAXS curves of 2 wt % β-casein solution at pH 2.6, at different temperatures. For better visibility, only each fifth experimental point of the scattering curves is shown. (b) Pair Distance Distribution Function (PDDF) obtained from the scattering curves by Indirect Fourier Transform (IFT). The area, which is proportional to the aggregation number, does not change significantly. The aggregation number was found to be similar at all temperatures. (c) Normalized PDDF deviates in shape from a homogenous sphere. $r_{max}$ is the value of r where the PDDF has its maximum. (panel d) The function $f(r)$ indicates a plate-like or disk-like particle shape with particle thickness of approximately 3.5 nm.
Figure 3B:
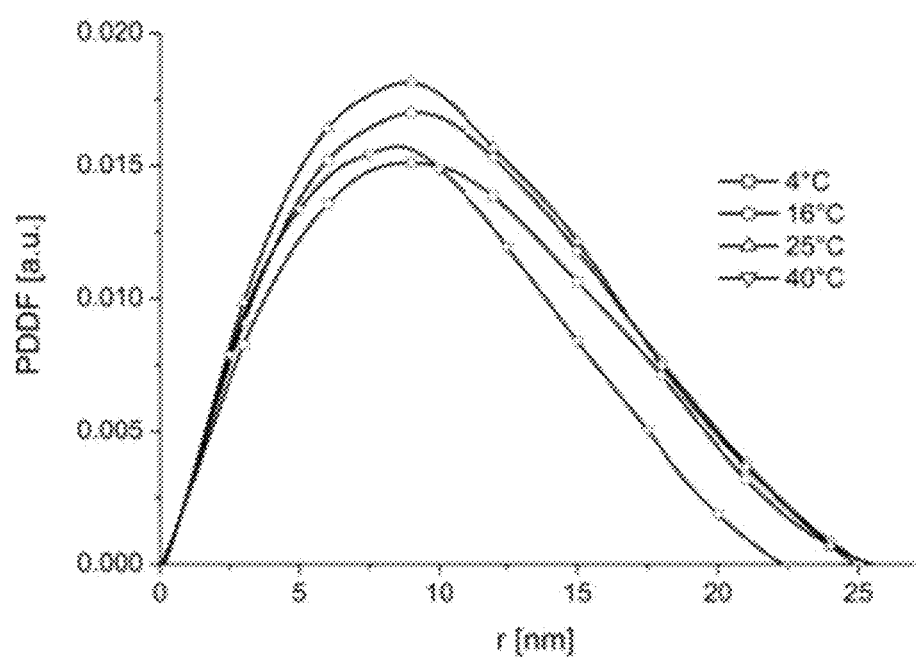
Figure 3C:
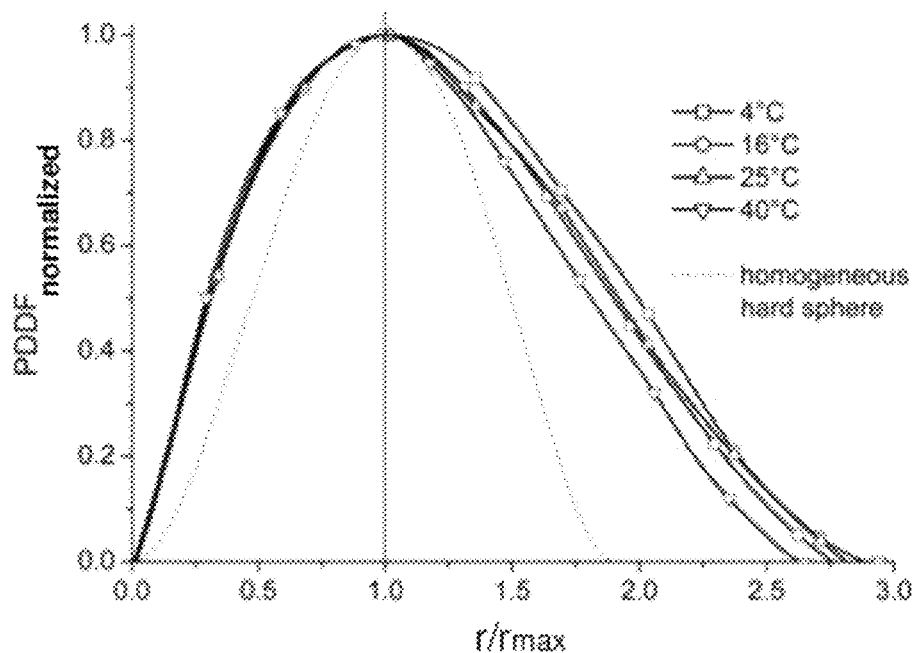
Figure 3D:
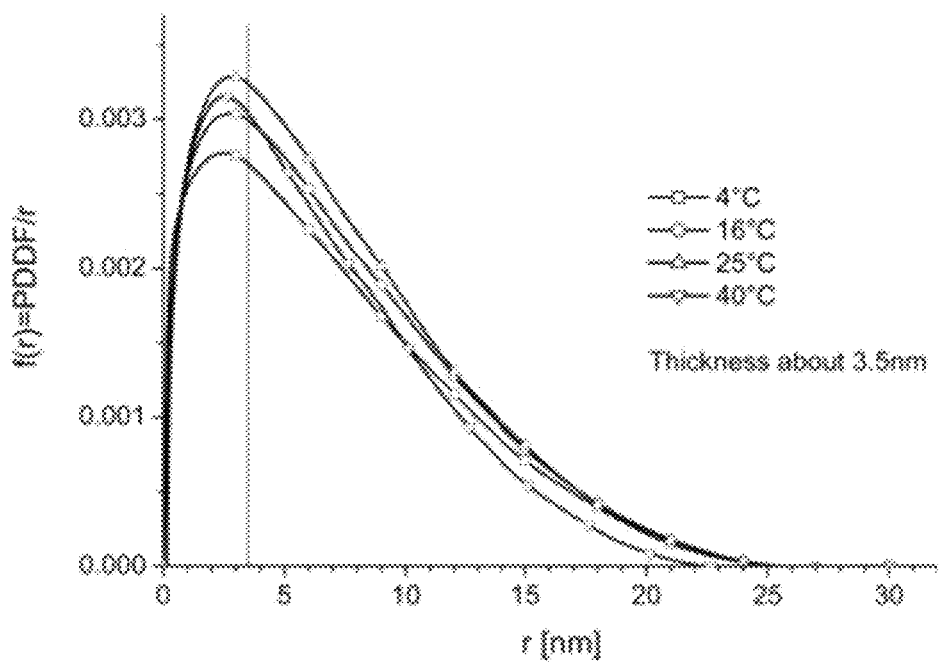

SAXS measurements were used to determine the shape and dimensions of the micelles at low pH more precisely, and to evaluate the micelle molecular weight (i.e., the aggregation number). The scattering curves of 20 mg/mL β-casein in lactic acid solution (pH 2.6, IS 0.0022) at different temperatures are shown in FIG. 3a. Interestingly, very little change in the scattering curves is observed in the complete range of temperatures studied (between 4 and 40° C.), as was also found by cryo-TEM (FIG. 2). Consequently, the calculated Pair Distance Distribution Functions (PDDF), are also similar (FIG. 3b). The maximum micelle dimension is approximately 35-40 nm at all temperatures. The area under the PDDF curve, which is proportional to the weight of one particle, is almost constant. To calculate the aggregation number, the density of the solvent and the solution was measured at various temperatures (Table 2). The aggregation number was found to vary only slightly (between 8 and 11) as the temperature was raised from 4 to 40° C. (Table 2). These differences are not significant, and they indicate that the micelle aggregation number remains practically constant within this wide range of temperatures, as was also indicated by the constant scattering profiles shown in FIG. 3a,b.

The shape of the PDDF gives information on the shape of the assemblies. The experimental PDDFs were compared with a theoretical PDDF of a homogeneous sphere, and all functions were normalized to a value of 1 at the x- and y-axes at the PDDF maximum (FIG. 3 panel c). It can be clearly seen that the micelles have a very similar shape at different temperatures. However, the particles' shape deviates strongly from the shape of a sphere. In fact, the curve shape is characteristic of scattering from flat, plate-like particles, as indeed was indicated by the cryo-TEM data (FIG. 2). As expected for flat particles, the function $f(r)$ (FIG. 3d) displays a peak after which it decreases almost linearly to the maximum dimension. From the transition point, which is marked with a line in FIG. 3d, the thickness of the particles was found to be close to 3.5 nm at all temperatures.

Figure 4A:
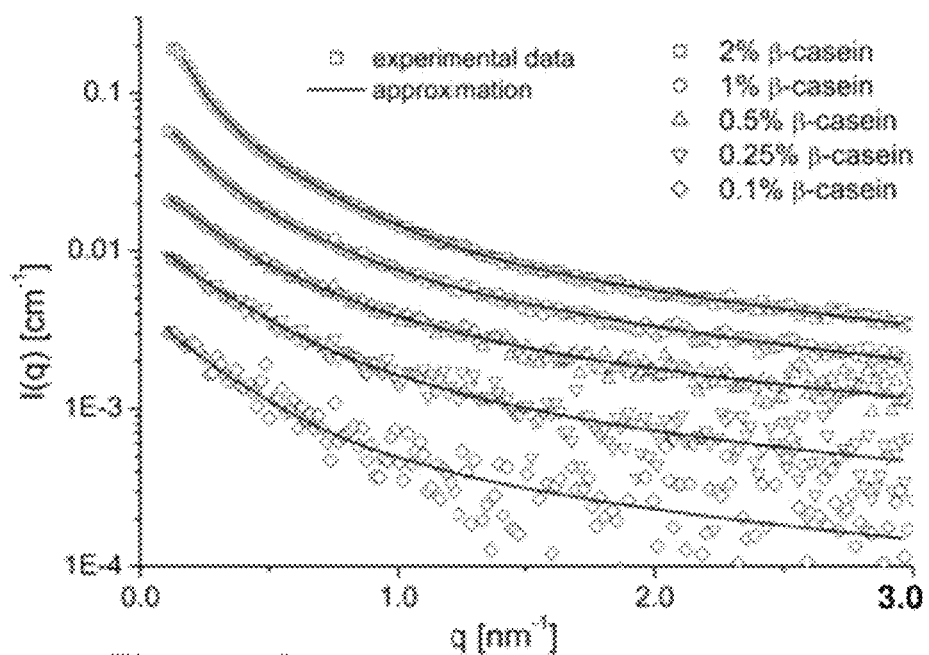
Figure 4B:
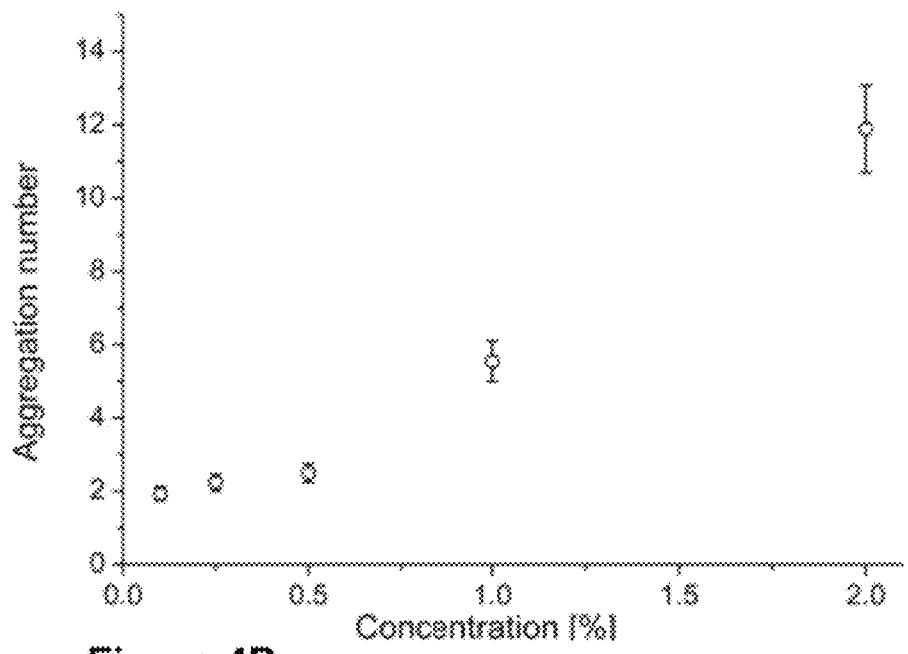

To determine the CMC and to investigate how the concentration affects the aggregation number, a series of dilutions, from 2.0 to 0.1 wt %, was prepared. The scattering curves were measured at 4° C. and were put on an absolute scale. The curves after subtraction of the solvent data are shown in FIG. 4a. As expected, the intensity of the scattering decreases when the concentration is decreased. But, in addition, there is also a change in the shape of the scattering curve. The upturn at low scattering angles is less pronounced at low concentrations, which indicates the presence of smaller particles. A detailed data evaluation described in the Experimental Procedures leads to the aggregation numbers shown in FIG. 4b. It is seen that above 0.5 wt %, Nagg strongly increases with the concentration, and at concentrations of 0.5 wt % and below, Nagg stays basically constant at a value of approximately 2. From this graph, the CMC of β-casein is estimated to be around 0.5 wt % at 4° C. An equivalent experiment was performed at 25° C. in which monomers were detected at the limit of dilution (0.1 wt %), dimers at 0.25 wt %, and a notable increase into higher oligomers at higher concentrations, suggesting that the CMC at 25° C. is in the range of 0.1-0.25 wt %. Without being bound by any theory or mechanism of action, the decrease in the CMC (from 0.5 to 0.1-0.25 wt %) upon raising the temperature from 4 to 25° C. may be explained by larger hydrophobic interactions at 25° C. than at 4° C., which drive the aggregation to occur at lower concentrations.

Figure 5A:
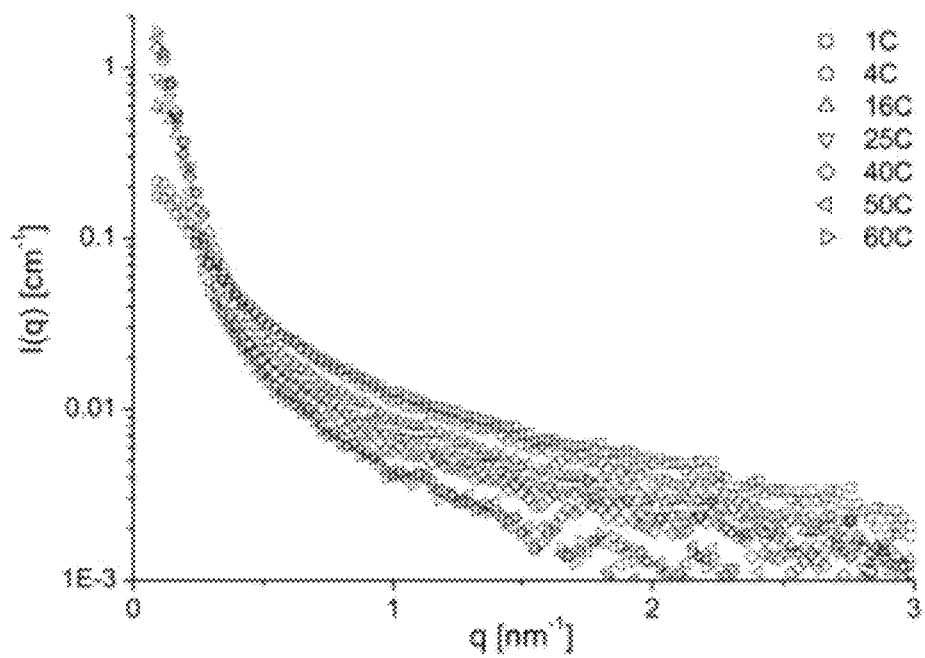
FIG. 5: (a) SAXS curves of a 2.0 wt % β-casein solution (pH 6.7) containing 0.05 M NaCl, at different temperatures. For better visibility, only each fifth experimental point of the scattering curves is shown. (b) The aggregation numbers determined from the scattering curves shown in panel a. The aggregation numbers increase with temperature. (c) PDDF obtained from the scattering curves by IFT. The area, which is proportional to the aggregation number, increases with temperature. (d) Normalized PDDF to show the deviation in shape from homogeneous monodispersed spheres.
Figure 5B:
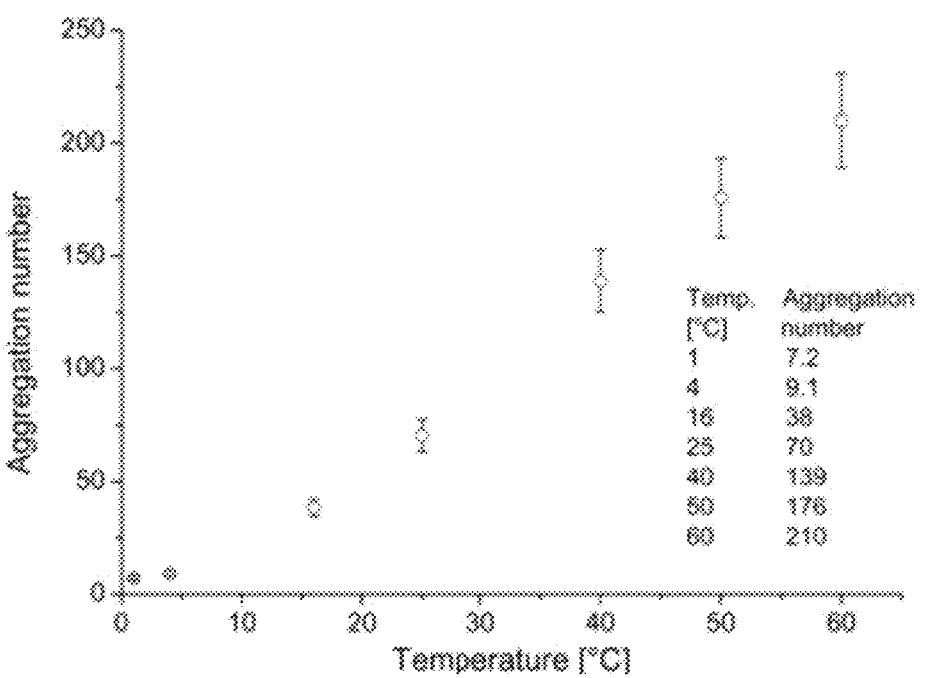
Figure 5C:
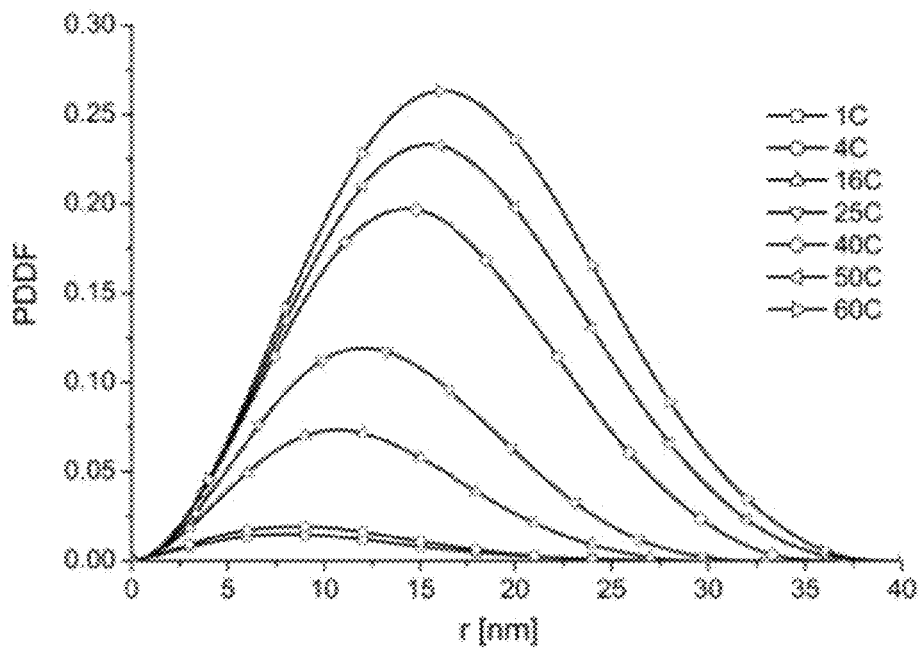
Figure 5D:
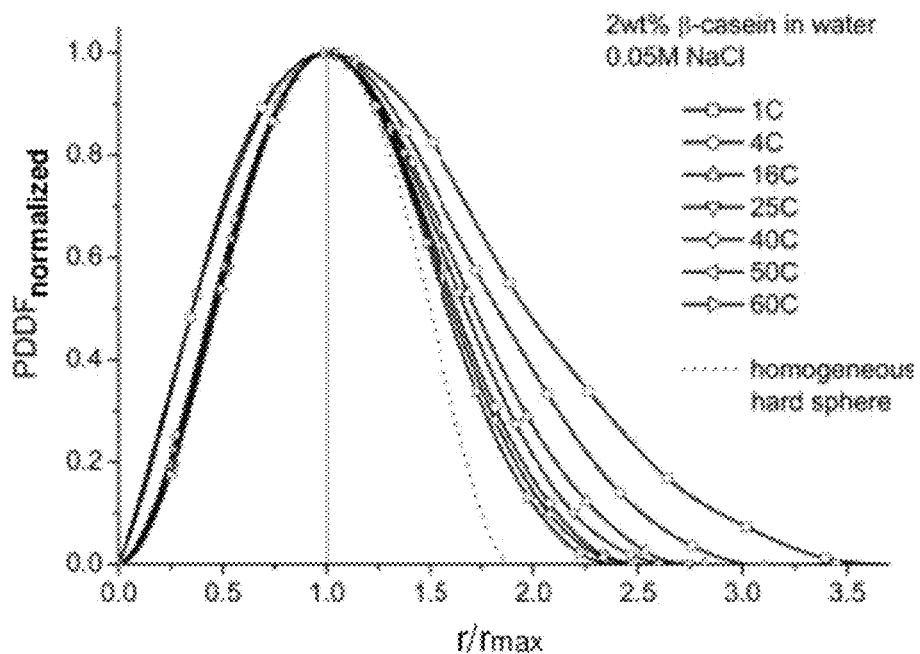

The β-casein micelles (20 mg/mL protein solutions) were further characterized at pH 6.7 in the presence of 0.05M NaCl at various temperatures between 1 and 60° C. (FIG. 5a). It is seen that the forward scattering intensity increases significantly in the low q regime but becomes smaller at high q values, as the temperature is increased. The aggregation numbers calculated from these data are shown in FIG. 5b. The aggregation number was found to increase from 7 to 210 as the temperature is raised from 1 to 60° C. As a result of the changes in the micelle dimensions, the area of the PDDF increases as well (FIG. 5c). The maximum dimension, which can be read from the point where PDDF reaches zero, grows from approximately from 25 to 40 nm. The shape of the micelles also changes upon heating. At low temperatures (4° C.), micelles exhibited a plate-like shape, similar to those existing at low pH. Interestingly, the deviation from the PDDF of a sphere is similar to that found at pH 2.6. However, the scattering data indicate that as the temperature is increased to 16° C. and above, the assemblies become more spheroidal in shape, which fits well with the formation of oblate and, at higher temperatures, more spherical micelles. As the temperature is raised further, the normalized PDDF curves show an almost perfect overlap with the theoretical curve of the sphere (FIG. 5d). No further growth was observed above 50° C.

TABLE 2

Characteristic properties of the micellar solutions and the micelles determined by SAXS as a function of temperature at acidic pH environment.

| pH | T, (° C.) | CMC (wt %) | $N_{agg}$ | Micelle Shape | Micelle Dimensions |
|---|---|---|---|---|---|
| 2.6 | 4 | 0.5 | 8 | disc | 25 nm in diameter and 3.5 nm thick |
|  | 16 | ND | 10 | disc |  |
|  | 25 | 0.1-0.2 0.19* | 11 6* | disc |  |
|  | 40 | ND | 9 | disc |  |

ND—not determined;
*the CMC was found by isothermal titration calorimetry (ITC).

EXAMPLE 6

Figure 6:
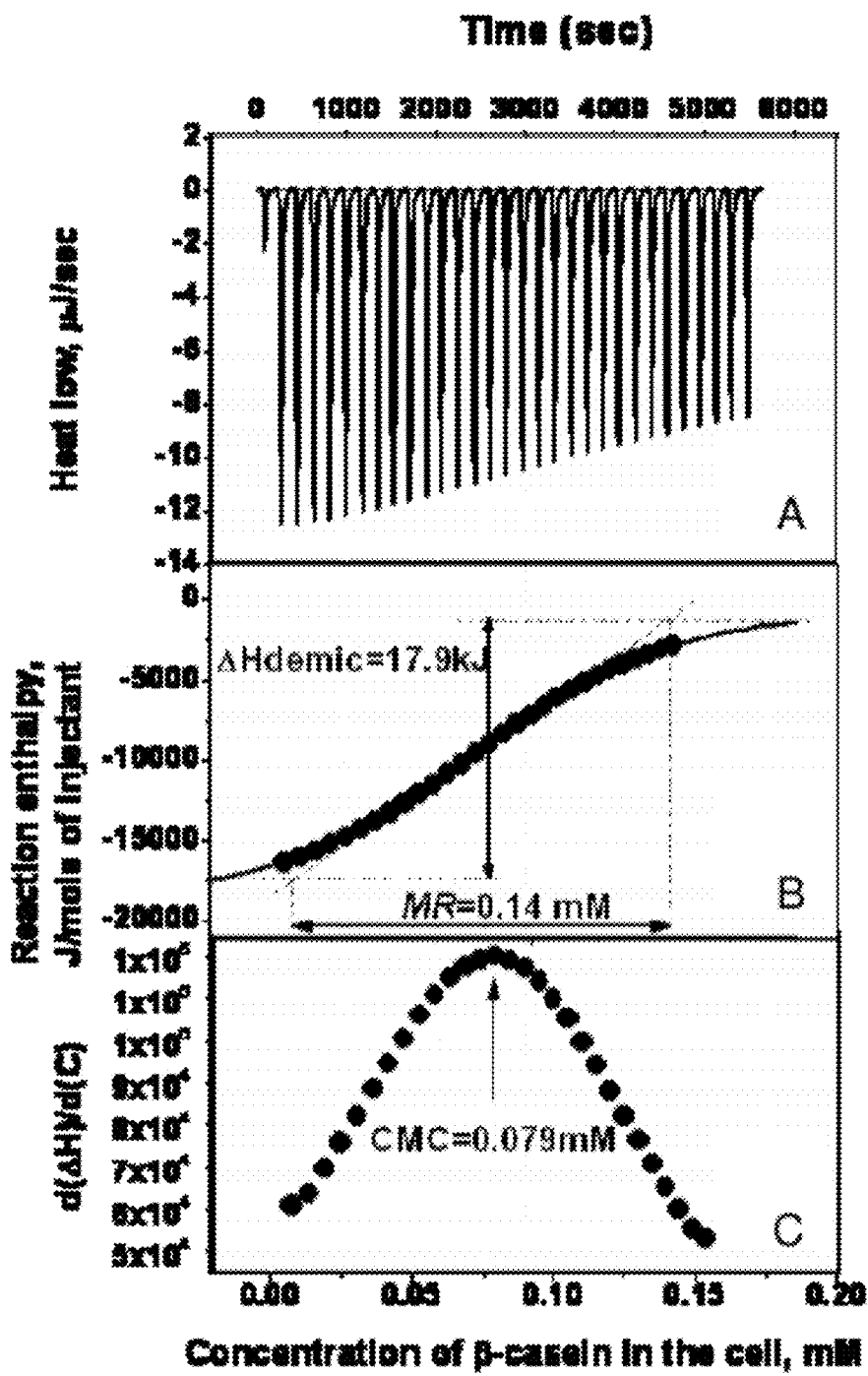
FIG. 6: Titration of micellar (20 mg/ml) β-casein solution in diluted lactic acid (pH 2.6) at very low ionic strength (0.002) into lactic acid solution, having the same pH and ionic strength, at 24° C.: (A) calorimetric traces, (B) reaction enthalpy vs. β-casein concentration in the cell, (C) first derivative of curve B calculated from the interpolated values.

Characterization of the β-Casein Micelles by ITC

β-casein micellar solution was titrated into lactic acid buffer (pH 2.6) placed in the ITC cell, and the heat flow was measured as a function of time (FIG. 6A). Three factors contribute to the exothermic enthalpy changes observed at the initial injections: micelle dilution, demicellization, and dilution of individual β-casein molecules. The enthalpy changes decrease in magnitude as more protein is added and the concentration in the ITC cell increases. Eventually, the concentration in the cell exceeds the CMC and only micelle dilution contributes to the heat flow. In FIG. 6B the heat of the reaction, obtained by integrating the peaks of the individual injections given in FIG. 6A, is plotted against the β-casein concentration in the cell. A slow increase in the reaction enthalpy was observed, resulting in micellixation relative cooperativity (MR) of 0.14 mM (FIG. 6b), which is more than twice than the value found at pH 7.0 and IS of 0.1. FIG. 6B also presents the heat of demicellization, ΔHdemic, which equals the enthalpy difference between the two asymptotes of the sigmoid fit of the experimental data (obtained by using the Origin software). It is shown that at 24° C. ΔHdemic is ≤17.9 kJ/mol, relatively small compared with the −40.53 kJ/mol found at pH 7.0 and IS of 0.1. The CMC, obtained from the β-casein concentration at which the first derivative of the reaction heat displays a maximum, was determined to be 1.89 mg/mL (FIG. 6C) at pH 2.6. This value is approximately twice the CMC found at pH 7 and ionic strength 0.1. The small ΔHdemic, the high CMC, and the large MR indicate that the driving forces for micellization under acidic conditions are reduced compared with those at physiological pH and high IS.

EXAMPLE 7

Characterization of the β-Casein Micelles by Sedimentation Equilibrium

Figure 7:
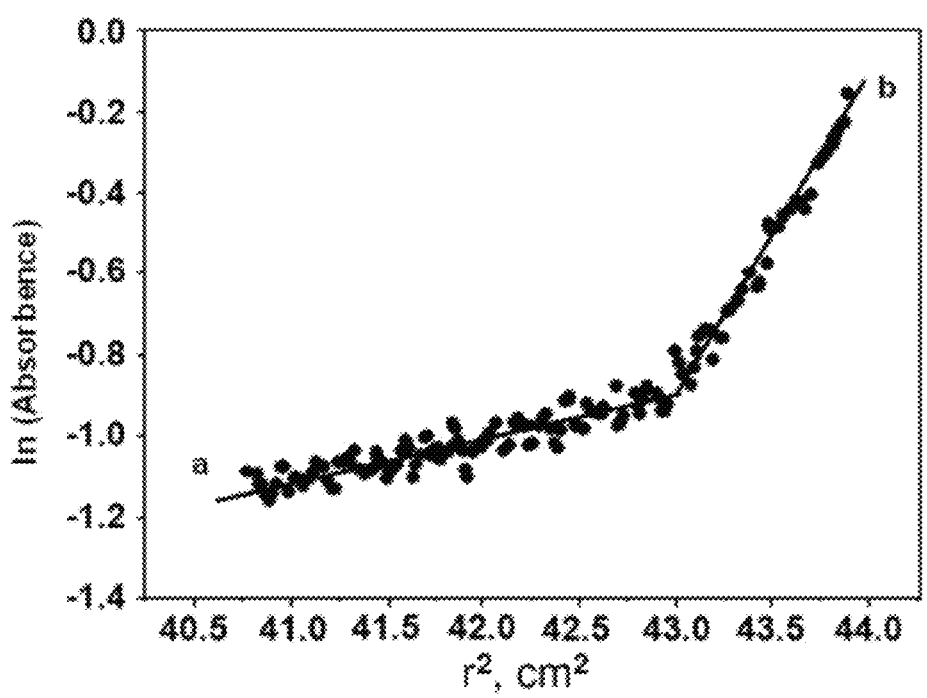
FIG. 7: Determination of β-casein aggregation number from the ultracentrifugation data at pH 2.6, protein concentration 5 mg/ml, ionic strength (IS) 0.002.

To determine the aggregation number of the micelles at pH 2.6, analytical ultracentrifugation experiments were conducted at various protein concentrations and at pH 7.0 and IS of 0.002. Sample data are plotted in FIG. 7, showing data with the protein concentration at 5 mg/ml, and ionic strength (IS) of 0.002. At concentrations lower than the CMC, determined by ITC to be 1.89 mg/mL (0.079 mM), a straight line was obtained. The aggregation numbers calculated from the slope of this line confirmed that the protein is monomeric at these concentrations. At concentrations higher than the CMC, two regions could be defined, indicating the presence of two protein populations: monomers at relatively short radii (i.e., in FIG. 7 at r<6.5 or r2<43) and assemblies at large radii. The micelles at pH 2.6 are characterized by a small aggregation number of 3 around the CMC and 6 at higher concentrations. In contrast, Nagg of 20 was measured at pH 7.0 and ionic strength 0.1. Thus, compared with assembly at neutral pH, assembly at low pH is characterized by two special features: the micelles are flat and disk-like in shape, and they have a low molecular weight.

EXAMPLE 8

Loading of Guest Low Molecular Weight Molecules of Different Physico Chemical Properties into the β-Casein Assemblies Calculated amounts of the guest molecules (usually a low molecular weight drug) are dissolved in ethanol or DMSO.

The dissolved guest molecule is then slowly titrated (2 microliter drops) into the vial containing the β-casein micelles. The solution is then strongly stirred, vortexed or sonicated for ~30 min depending on the type of encapsulated molecule, the overall concentration of the β-casein micelles and the molecule to be encapsulated, temperature, pH and ionic strength. Titration is continued until reaching the required drug-to-protein concentration. β-casein protein concentration after mixing ranges from 0.1% to 4%. Typical drug-to-β-casein protein concentrations at the final mixture ranges from 0.5:1 up to 16:1. The solvent (e.g., ethanol) content might be up to 10% but is typically not more than 5%. The mixing, either by strong stirring, vortexing or sonication is usually performed at room temperature for 30 minutes, or with solutions warmed to 40° C. Usually after an hour, the turbidity is measured for the first time. The solubility and stability of the drugs significantly increases upon mixing with the β-casein.

The guest molecules can be varied in their physicochemical properties to include molecules which are highly hydrophobic and immiscible in water (the steroidal drug budesonide and celecoxib), amphiphilic (the steroidal prodrug methylprednisolone hemisuccinate sodium salt (MPS)) and soluble in water in a pH dependent manner, or polar (ionic and nonionic) water soluble (e.g sodium clodronate). Physical properties of these molecules are summarized in Table 3.

symptoms, and to reduce numbers of colon and rectum polyps in patients with familial adenomatous polyposis.

Celecoxib is approved for use in osteoarthritis, rheumatoid arthritis, acute pain, painful menstruation and menstrual symptoms, and to reduce the number of colon and rectal polyps in patients with familial adenomatous polyposis. It was originally intended to relieve pain while minimizing the gastrointestinal adverse effects usually seen with conventional NSAIDs. In practice, its primary indication is in patients who need regular and long term pain relief: there is probably no advantage to using celecoxib for short term or acute pain relief over conventional NSAIDs. In addition, the pain relief offered by celecoxib is similar to that offered by paracetamol. Celecoxib is another non-limiting example of a non-chemotherapeutic agent according to the present invention.

Figure 8A:
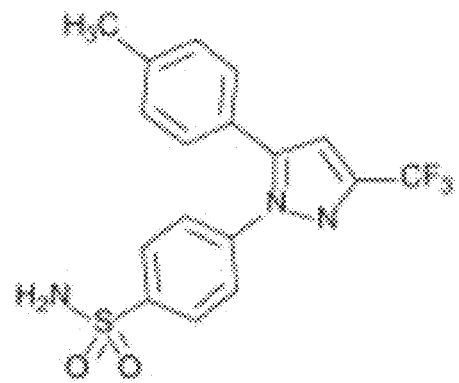
FIG. 8: (A) The chemical structure of celecoxib. (B) Photographs of celecoxib in lactic acid (a-c) and in 2% β-casein, at increasing drug content; 0.5:1 (a1), 1:1 (b1) and 2:1 (c1)
FIG. 8C shows a photograph of celecoxib in hepes buffer with 2% of β-casein with a drug: β-casein mole ratio of 4:1 (left vial) and a total concentration of celecoxib of 24 mg/ml (right vial—celecoxib only).
Figure 8B:
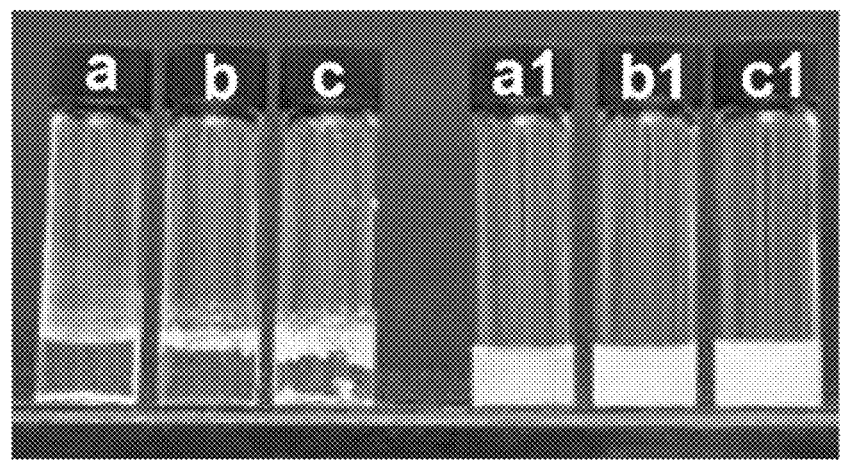
Figure 8C:

FIG. 8A shows the chemical structure of celecoxib, while FIG. 8B shows photographs of celecoxib in lactic acid (a-c) and in 2% β-casein, at increasing drug content. The suspension containing the loaded vehicles is stable over long times.

Figure 9:
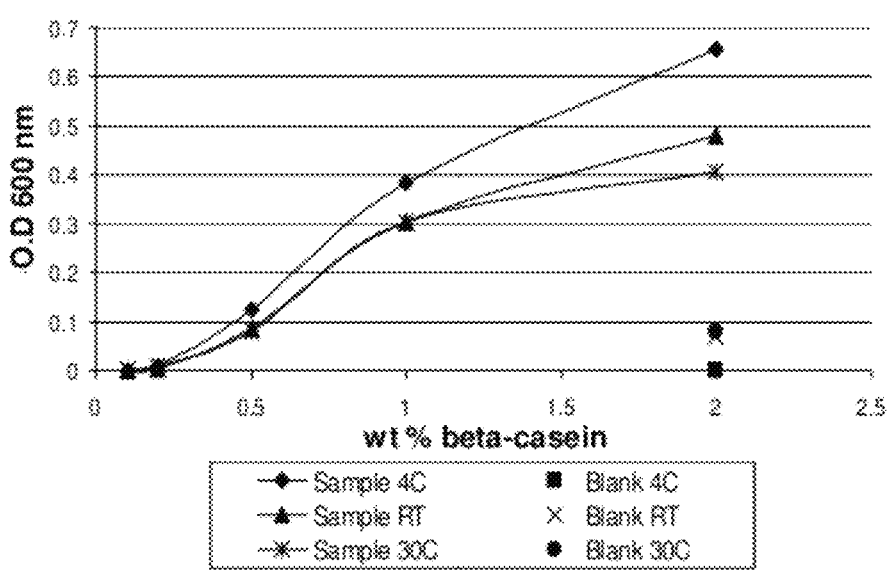
FIG. 9: Turbidity as a function of β-casein concentration and temperature for 1:1 β-casein to celecoxib ratio solution in lactic acid solution, pH 2.6.

FIG. 9 shows the variation of the turbidity of β-casein/celecoxib solutions (lactic acid solution, pH 2.6). At 4° C. the complexes reversibly precipitate, and at room temperature they are rapidly re-dispersed in solution. The blank solution is

TABLE 3

The physical properties of budesonide, celecoxib, MPS and sodium clodronate.

| Properties | Budesonide | Celecoxib | MPS | Sodium clodronate |
|---|---|---|---|---|
| Molecular Weight | 430.53 | 381.37 | 474.54 | 244.9 |
| $pK_a$ | 12.85 ± 0.10 | −6.12 ± 0.50 (most basic, 25° C.) 9.68 ± 0.10 (most acidic, 25° C.) | 4.29 ± 0.17 | 7.37, 8.07 |
| Polar surface area $A^2$ | 93.1 | 86.4 | 138.2 | 134.7 |
| Total area $A^2$ | 638.1 | 484.1 | 380.54 | 226.9 |
| Non-polar Area $A^2$ | 545 | 397.7 | 242.34 | 92.2 |
| Non-polar/polar | 5.85 | 4.60 | 1.75 | 0.68 |
| $ASA\_H^e$ | 441.2 | 370.5 | 404.40 | 62 |
| $ASA\_P^f$ | 94.9 | 240 | 190.50 | 258.9 |
| $ASA\_H/ASA\_P$ | 4.65 | 1.54 | 2.12 | 4.18 |
| Intrinsic Molar Solubility | 3.5E−5 mol/L | 1.3E−6 mol/L | 1.7E−5 mol/L | 30.5 mM |
| Molar Solubility [pH] | 3.5E−5 mol/L [1] to [10] | 1.3E−6 mol/L [1] to [8] | 1.7E−5 [1], [2] 1.8E−5 [3] 2.6E−5 [4] 1.1E−4 [5] 8.9E−4 [6] 8.1E−3 [7] | |
| logP | 3.142 | 4.213 | 2.688 | −0.85 |
| logD [pH] | 3.14 [1] to [10] | 4.21 [1] to [7] | 2.69 [1] [2] 2.67 [3] 2.51 [4] 1.9 [5] 0.98 [6] 0.02 [7] | −5.22 [4] −5.38 [5] −5.4 [6] −5.55 [7] −6.33 [8] −7.9 [9] |
| Charge [pH] | 0 [4-9] | 0 [4] 0 [5] 0 [6] 0 [7] −0.01 [8] −0.06 [9] | −0.69 [4] −0.96 [5] −1 [6] −1 [7] −1 [8] −1 [9] | −2 [4] −2 [5] −2.05 [6] −2.38 [7] −3.27 [8] −3.87 [9] |

EXAMPLE 9

Representative Results with Celecoxib in Acidic and Neutral pH

Celecoxib is a non-steroidal anti-inflammatory drug (NSAID) used in the treatment of osteoarthritis, rheumatoid arthritis, acute pain, painful menstruation and menstrual transparent due to the immiscibility of the drug in the buffer. The protein solution is also transparent because it includes only small assemblies of up to ~20 nm in diameter.

Figure 10:
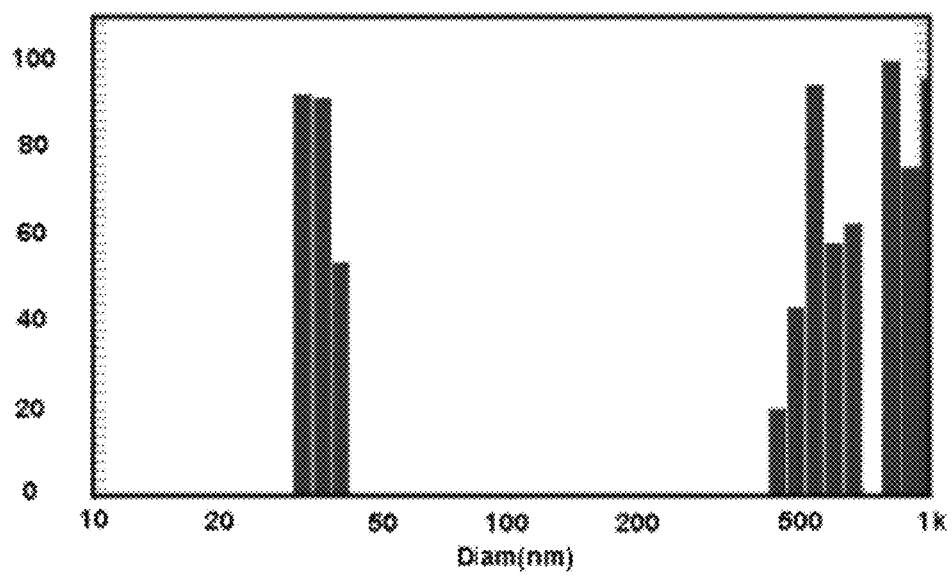
FIG. 10: Dynamic light scattering (DLS) data of celecoxib/protein complexes in lactic acid solution. 1 wt % β-casein, 1:1 drug-protein mole ratio.

FIG. 10 shows, in a dynamic light scattering experiment, two distinct populations were observed: swollen micelles with characteristic diameter of 30-40 nm, and large complexes of 0.5 micron and up. The population of small assemblies is directly observed by cryo-TEM (as detailed below);

the assemblies that are in the micrometer range are visible by light microscopy at Nomarski optics.

Figure 11:
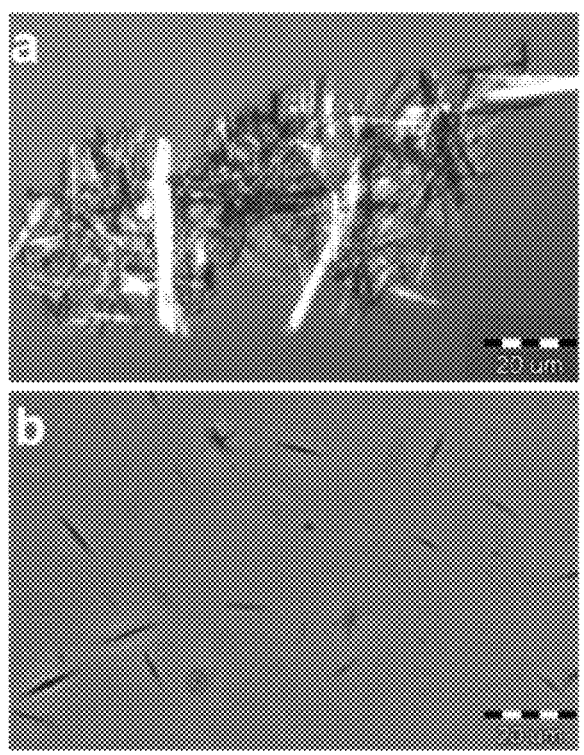
FIG. 11: Light microscopy images at pH 2.6 showing: (a) large crystals of celecoxib in lactic acid buffer. (b) celecoxib in the same solution and pH, in 1 wt % β-casein at protein:drug mole ratio of 1:0.5. The same amount of drug is present in a and b.
Figure 12:
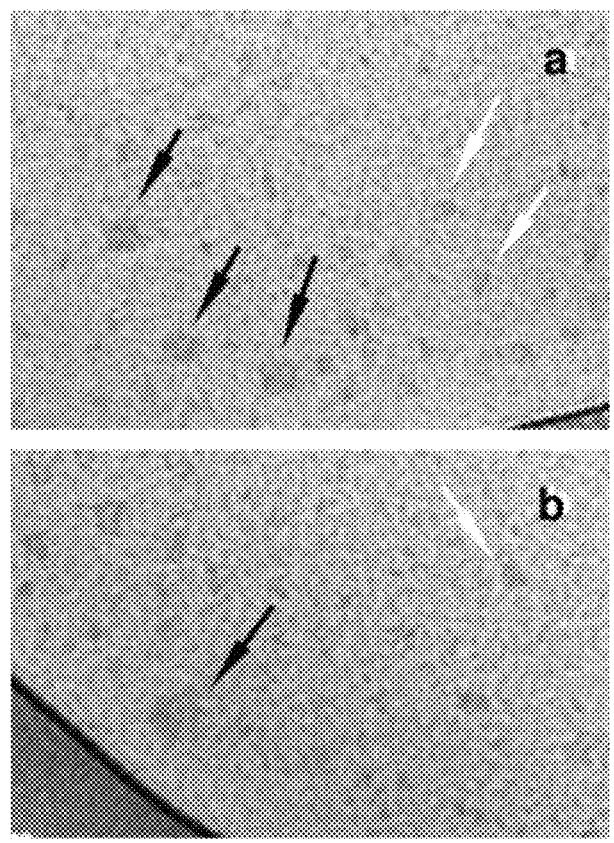
FIG. 12: Cryo-TEM images of celecoxib loaded into β-casein micelles, in hepes buffer (pH 6.8). White and black arrows point to mixed protein-drug micelles Bar=100 nm. Protein concentration is 0.5 wt %, protein-to-drug mole ratio is 1:1.

FIG. 11 features light microscopy images at pH 2.6 showing: (a) large crystals of celecoxib in lactic acid buffer. (b) Celecoxib in the same solution and pH, in 1 wt % β-casein at protein:drug mole ratio of 1:0.5. Note the significant decrease in the size upon the complexation with the protein. The same amount of drug is present in a and b. FIG. 12 features cryo-TEM images of celecoxib loaded into β-casein micelles, in hepes buffer (pH 7.1). White and black arrows point to mixed protein-drug micelles. Bar=100 nm. The cryo-TEM samples were prepared by preparing a thin liquid sample and plunging it into liquid ethane at its freezing temperature, forming a vitrified sample. The vitrified sample was transferred to liquid nitrogen and examined at cryogenic temperatures revealing the structures at their native state. The tested protein concentration was 0.5 wt %, and the protein-to-drug ratio was 1:1.

EXAMPLE 10

Representative Results with Budesonide in Acidic and Neutral pH

Budesonide is a glucocorticoid steroid for the treatment of asthma, non-infectious rhinitis (including hay fever and other allergies), and for treatment and prevention of nasal polyposis. Additionally, it is used for inflammatory bowel disease. With regard to the present invention, it is an example of a non-chemotherapeutic agent.

Figure 13A:
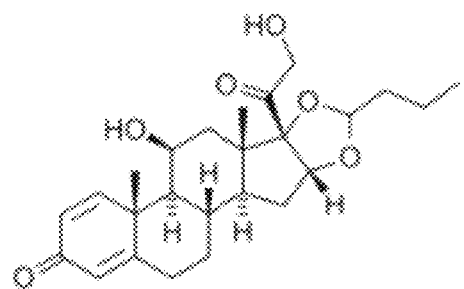
FIG. 13: (A) The chemical structure of budesonide. (B) Photographs of budesonide in lactic acid (a) and in 2% β-casein (b) protein-to-drug ratio is 1:1.
Figure 13B:
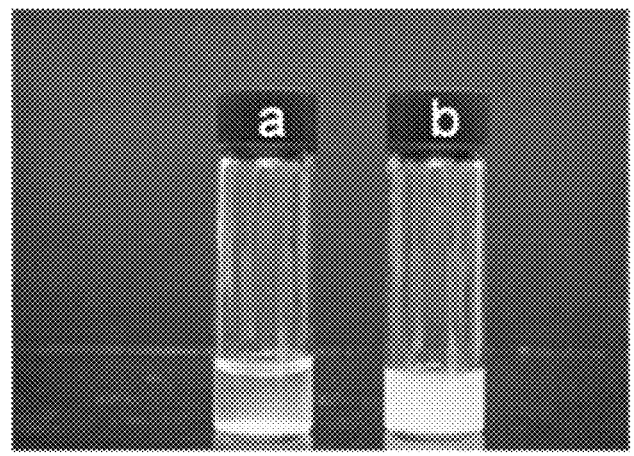

FIG. 13A shows the chemical structure of budesonide, and 13B shows photographs of budesonide in lactic acid (a) and in 2% β-casein (b); in both cases the protein-to-drug ratio is 1:1. The suspension containing the loaded vehicles is stable over long times.

Figure 14:
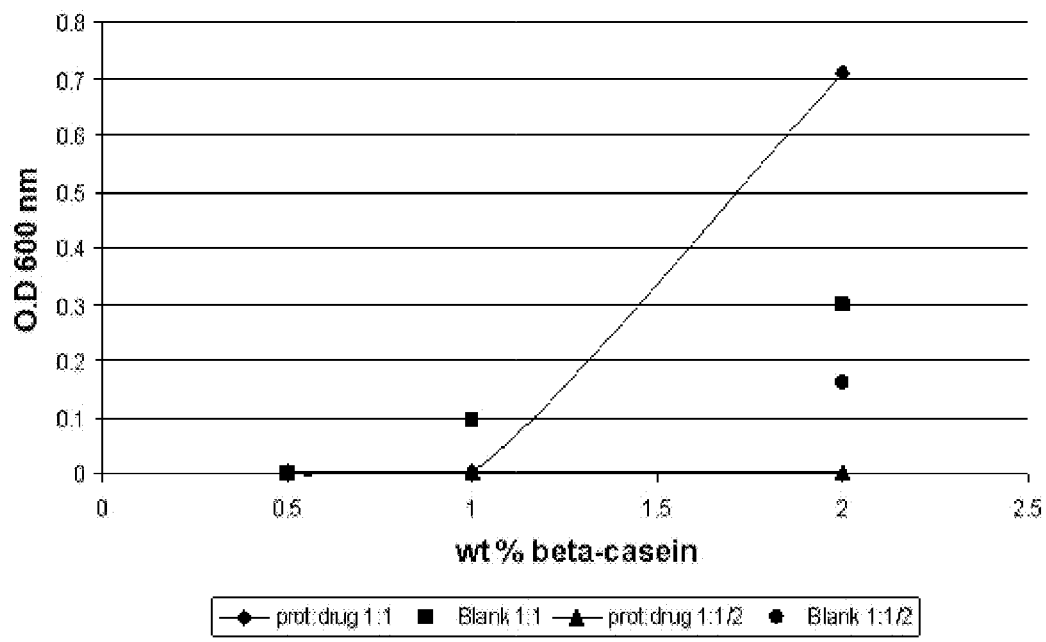
FIG. 14: Variation of the turbidity of β-casein/budesonide dispersions (lactic acid solution, pH 2.6). Protein concentration is between 0.5 wt % and 2 wt %. Protein-to-drug mole ratio was 1:0.5 and 1:1.

FIG. 14 shows the variation of the turbidity of β-casein/budesonide dispersions (lactic acid solution, pH 2.6). The drug solution is more transparent because the drug being immiscible is precipitating out of the solution. Upon entrapment in the β-casein complexes a stable suspension is formed. The protein concentration was varied between 0.5 wt % and 2 wt %. Protein-to-drug mole ratio was 1:05 and 1:1.

Figure 15:
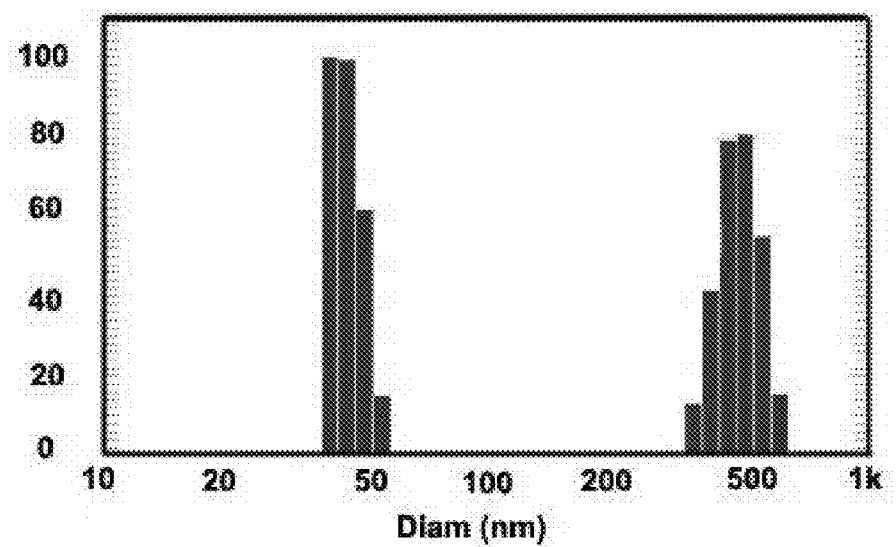
FIG. 15: DLS data of budesonide in lactic acid solution containing 1 wt % β-casein, 1:2 protein-to-drug mole ratio.

FIG. 15 shows the DLS data of budesonide in lactic acid solution containing 1 wt % β-casein, 1:2 protein-to-drug ratio. Two distinct populations may be seen: swollen micelles with characteristic diameter of 40-60 nm, and large complexes of 0.3-0.5 micron in size. Larger assemblies that can be seen by light microscopy were excluded from this analysis. The small assemblies are swollen mixed micelles. Note they are bigger than those found with celecoxib. The second population relates to drug crystals coated by the assembled protein, as seen by TEM methods (cryo-TEM and freeze-fracture TEM).

Figure 16:
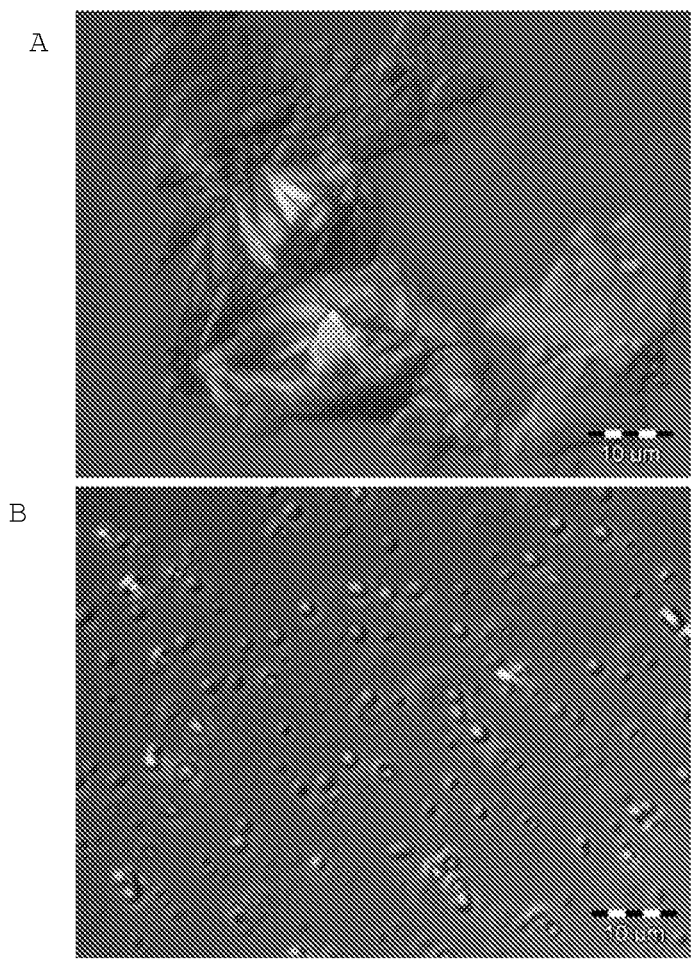
FIG. 16: Light microscopy images at pH 2.6 showing (a) budesonide structures in lactic acid buffer, and (b) budesonide-protein structures at the same solution and pH. β-casein is 2 wt %, protein:drug mole ratio of 1:4 (mole ratio).

FIG. 16 shows light microscopy images at pH 2.6 showing (a) budesonide structures in lactic acid buffer, and (b) budesonide-protein structures at the same solution and pH. β-casein is 2 wt %, protein:drug mole ratio of 1:4. Note the significant decrease in the size of the complexes upon interaction with the protein. The size of the complexes is below 1 micron, as confirmed by DLS and light microscopy. Optics effects cause the complexes to appear bigger in size and hollow.

Figure 17:
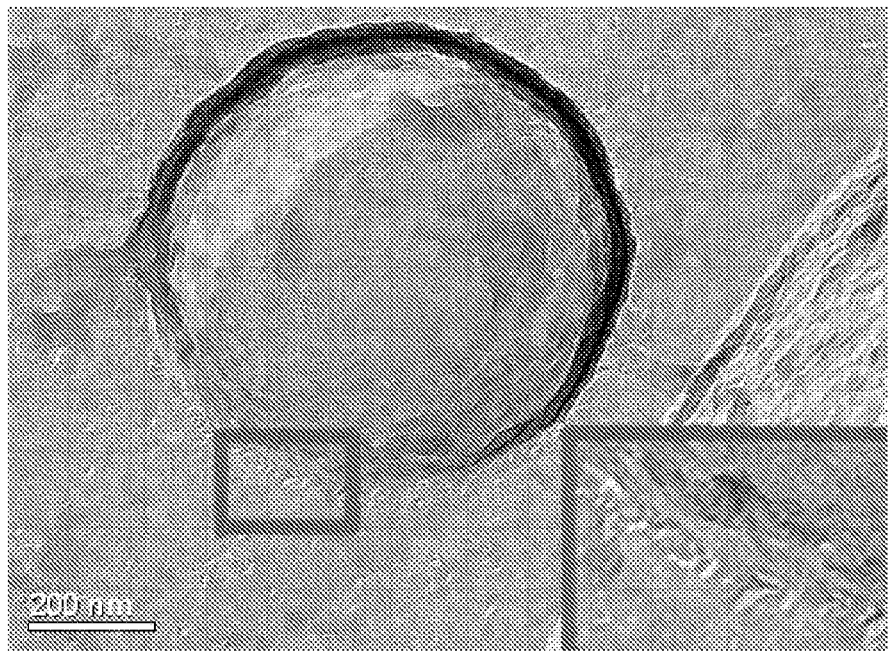
FIG. 17: Freeze-fracture TEM image showing β-casein/budesonide complex in lactic acid solution at pH 2.6. 2 wt % protein, 1:2 protein-to-drug mole ratio.

FIG. 17 shows a freeze-fracture TEM image showing β-casein/budesonide complex, with additional β-casein micelles and molecules at the surface. (Lactic acid, pH 2.6). The complex size is ~0.5 micron, in agreement with the DLS data. The micelles feature 2 wt % protein, 1:2 protein-to-drug ratio.

Figure 18:
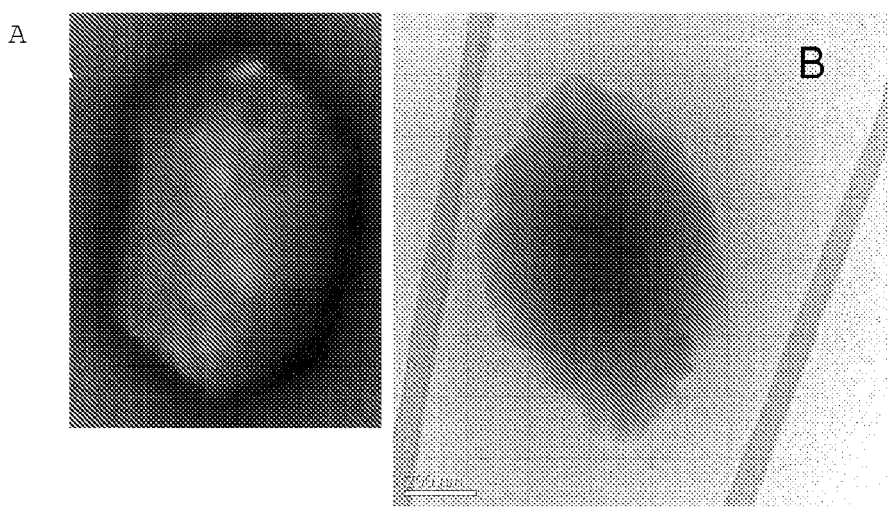
FIG. 18: Negative-stain (A) and cryo-TEM (B) images showing the β-casein/budesonide complexes in lactic acid solution at pH 2.6. 2 wt % protein, 1:2 protein-to-drug ratio.

FIG. 18 shows a negative-stain (left) and cryo-TEM (right) images showing the β-casein/budesonide complexes. Again the micelles feature 2 wt % protein, 1:2 protein-to-drug ratio.

Figure 19:
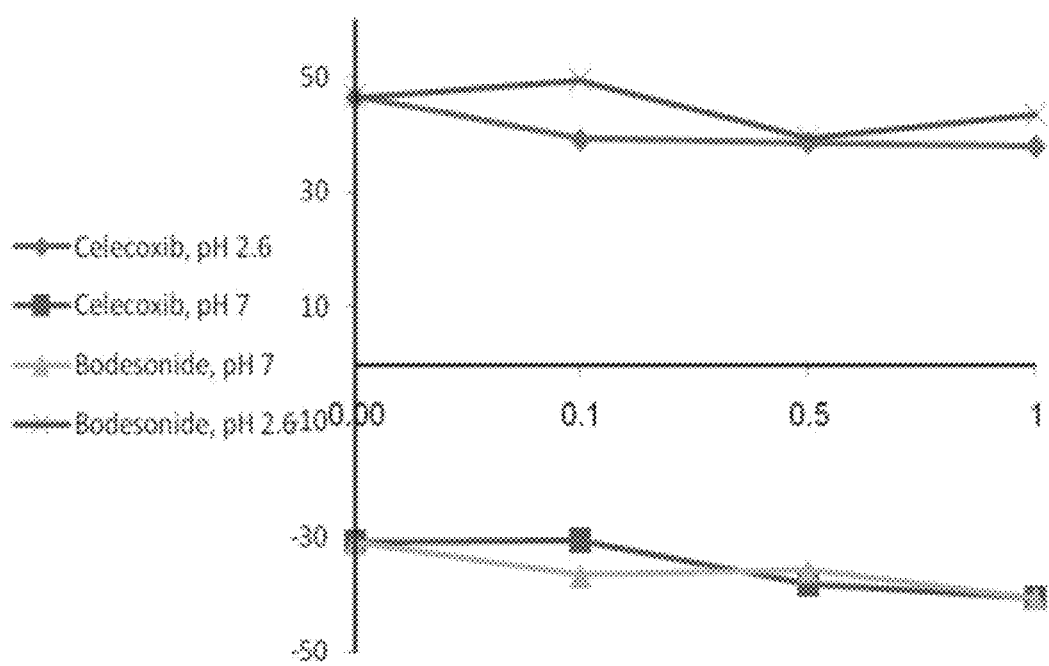
FIG. 19: Plot of the zeta-potential of Celecoxib and budesonide in β-casein, at acidic and neutral pH environments. Protein concentration is 0.1 wt %, protein-to-drug ratio is 1:1.

FIG. 19 shows the plot of the zeta-potential of celecoxib and budesonide in β-casein, at the two pH environments studied. The figure shows that the protein electrostatic characteristics are dominant and are not drug dependent. The micelles feature a protein concentration of 0.1 wt %; the protein-to-drug ratio is 1:1. The term "zeta potential" refers to electrokinetic potential in colloidal systems, which is the difference in potential between the dispersion medium and the stationary layer of fluid attached to the dispersed particle (all particles feature such a stationary layer of fluid at the interface with the surrounding medium). The fact that the protein electrostatic characteristics are dominant further strengthens the utility of the present invention as being suitable for a wide variety of therapeutic agents.

EXAMPLE 11

Representative Results with MPS

Methylprednisolone sodium succinate (MPS) is a synthetic corticosteroid used in severe conditions to reduce inflammation. It is therefore used to treat inflammatory disorders including but not limited to asthma; arthritis; severe allergic reactions; Crohn's disease; and systemic lupus erythematosus. It can be used to decrease fluid retention and swelling in the brain (cerebral edema) due to a brain tumor. It is also used to suppress the immune system in organ transplantation. MPS is widely used in the management of renal transplantation. To use MPS without severe adverse reactions, lower administration rates and dosages are very important, and may optionally be achieved with the micelles of the present invention. With regard to the present invention, it is an example of a non-chemotherapeutic agent.

Figure 20A:
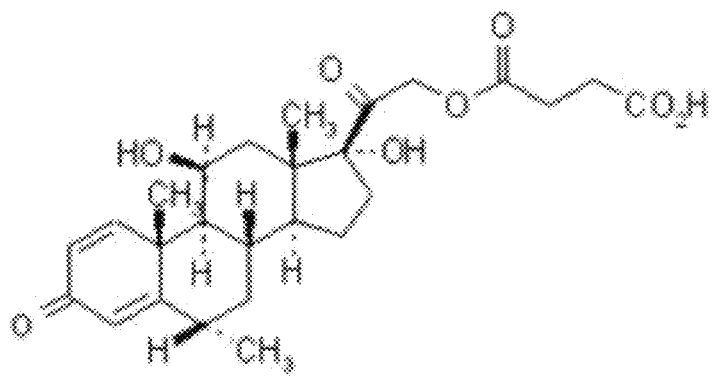
FIG. 20: (A) The chemical structure of MPS. (B) DLS data of MPS in lactic acid solution containing 1 wt % β-casein, protein-to-drug mole ratio is 1:2.
Figure 20B:
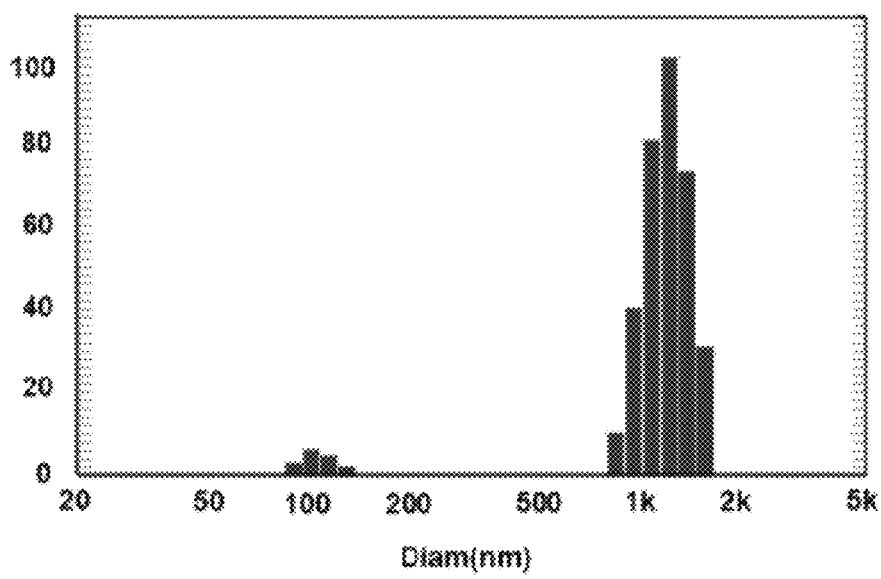

FIG. 20A shows the chemical structure of MPS. FIG. 20B shows DLS data of MPS in lactic acid solution containing 1 wt % β-casein, protein-to-drug ratio is 1:2 Note coexistence of two populations: mixed protein-drug complexes that are about 90-120 nm, and larger complexes of ~0.5-1.5 micron.

Figure 21:
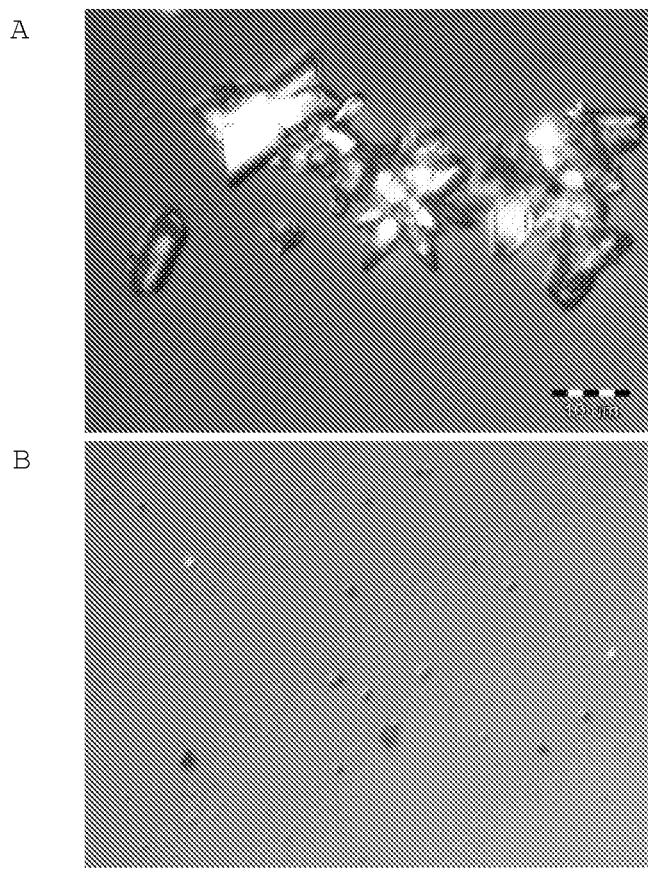
FIG. 21: Light micrsocpy images of MPS aggregates in the absence (A) and the presence of in 2% β-casein (B) in lactic acid solution (pH 2.6). protein-to-drug mole ratio is 1:2.

FIG. 21 shows light microscopy images of MPS aggregates in the absence (A) and the presence of in 2% β-casein (B); lactic acid solution (pH 2.6). The mixed assemblies are much smaller in size, indicating clearly the interaction between the protein and the drug. The protein-to-drug ratio is 1:2.

EXAMPLE 12

Representative Results with Sodium Clodronate

Sodium clodronate reduces bone destruction that could result in bone pain and fractures. It is also used to bring down high calcium ions blood levels to normal as well as maintain normal calcium blood levels. In some cases, it is used as an adjunct to cancer treatment, to prevent bone weakening and fractures. With regard to the present invention, it is an example of a non-chemotherapeutic agent.

Figure 22:
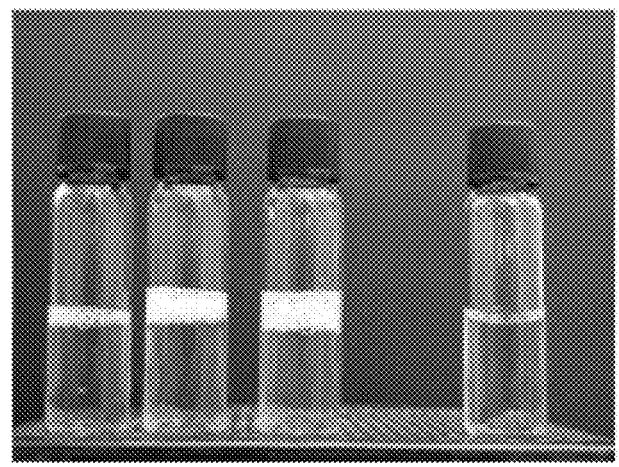
FIG. 22: Photographs of sodium clodronate in lactic acid (right) and in β-casein (a). Left to right: increasing protein concentration equal to 0.5%, 1% and 2%, at constant 1:2 protein:drug ratio.

FIG. 22 features photographs of sodium clodronate in lactic acid (D) and in β-casein (A-C). Left to right: increasing protein concentration equal to 0.5% (A), 1% (B) and 2% (C), at constant 1:2 protein:drug ratio. All suspensions were transparent.

Figure 23:
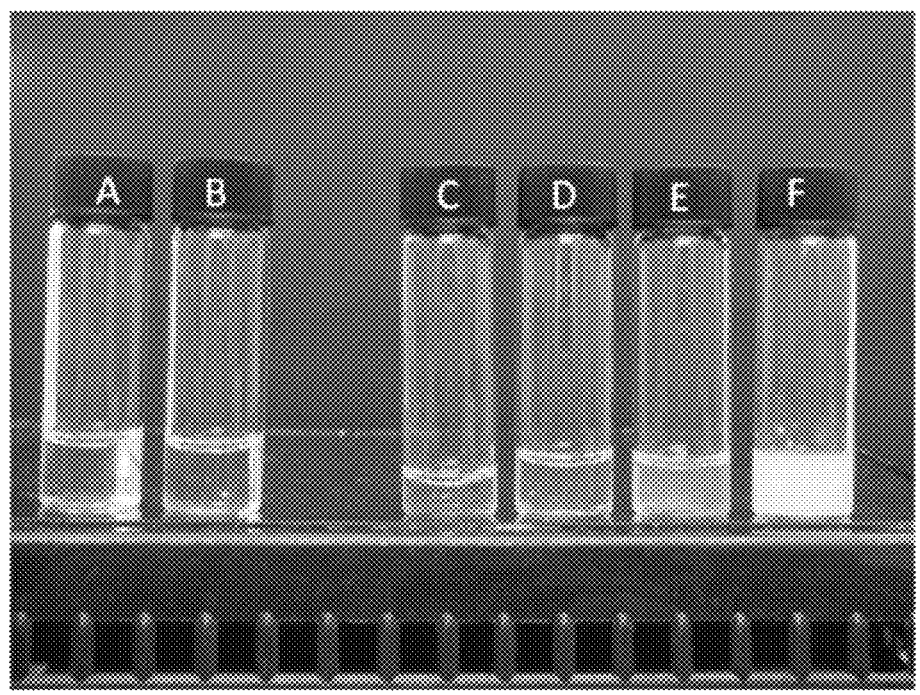
FIG. 23: Photographs of sodium clodronate and β-casein solutions with increasing ratios of sodium clodronate to β-casein in lactic acid (pH 2.6). A: Sodium clodronate only; B: β-casein only; C: 1:1; D: 2:1; E: 4:1; F: 10:1; β-casein concentration was equal to 2% by weight.

FIG. 23 features photographs of sodium clodronate and β-casein solutions with increasing ratios of sodium clodronate to β-casein in lactic acid (pH 2.6). A: sodium clodronate only; B: β-casein only; C: 1:1; D: 2:1; E: 4:1; F: 10:1; β-casein concentration equal to 2% by weight.

Figure 24:
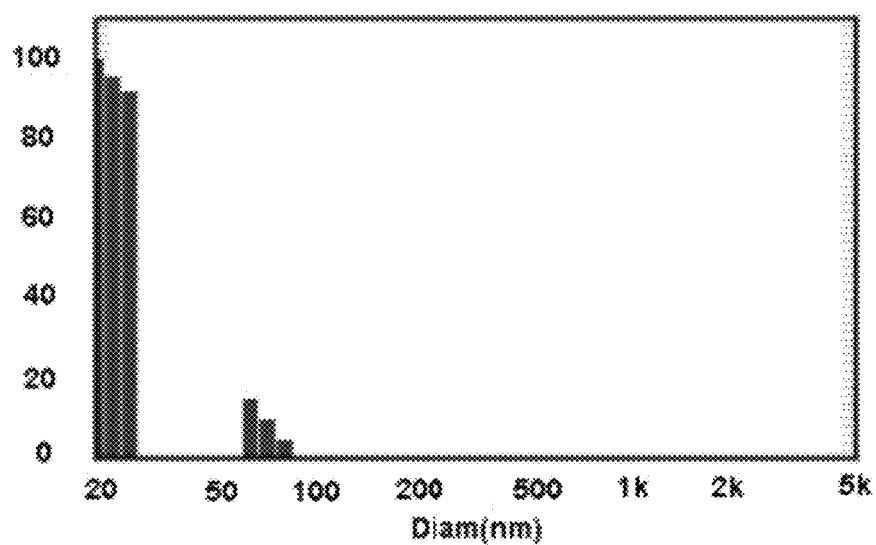
FIG. 24: DLS data of sodium clodronate in lactic acid solution at pH 2.6 containing 2 wt % β-casein; the protein-to-drug ratio is 1:2.

FIG. 24 features DLS data showing two small populations of micelles. The smaller population is probably of empty micelles. The aggregates at the 69-90 nm in size are likely micelles loaded with sodium clodronate. The protein concentration is 2%, and the protein-to-drug ratio is 1:2.

EXAMPLE 13

β-Casein-Celecoxib Assemblies in Different pH Values

Bovine β-casein (>90%; Sigma-Aldrich) was dissolved in pH 7.0 hepes buffer containing 200 mM hepes (MP Biomedicals), 10 mM $MgCl_2$ (Sigma-Aldrich), 20 mM EGTA (Sigma-Aldrich) and 10 mM NaCl (Loba Chemie), and was placed over-night at 4° C. under stirring. The protein solutions were prepared at concentrations ranging from 0.5 to 2 wt % (0.21 to 0.83 mM respectively), and were filtered through a porous membrane of 0.45 µm to avoid large protein aggregates. Celecoxib was dissolved in 100% ethanol (Bio Lab) and a known amount of that solution was titrated to the protein micellar solution under stirring, up to a maximum of 5% ethanol in the final solution. Stirring continued for 30 minutes in room temperature. The obtained suspensions were transparent, and contained β-casein and celecoxib, in protein:drug mole ratios ranging from 1:0.5 to 1:15. The specimens remained stable i.e., no precipitation was observed, for at least 3 weeks at 4° C. As a control, a solution of celecoxib in 100% ethanol was titrated under stirring to the same hepes buffer, and the stirring continued for 30 minutes in room temperature. All control solutions were cloudy, indicating the poor solubility of celecoxib in aqueous solution without β-casein.

Protein and protein-drug solutions were lyophilized by freezing in liquid nitrogen followed by drying in a Christ Alpha 1-4 lyophilizer for 24 hours. The specimens were stored in 4° C. until re-suspension in hepes buffer, back to the original concentration (0.5 wt % or 2 wt %), or to a higher concentration of 5 wt %. Re-suspension was performed by weighing the powder, adding a measured amount of buffer and stirring for 30 minutes in room temperature. The suspensions obtained were transparent and stable.

Figure 25:
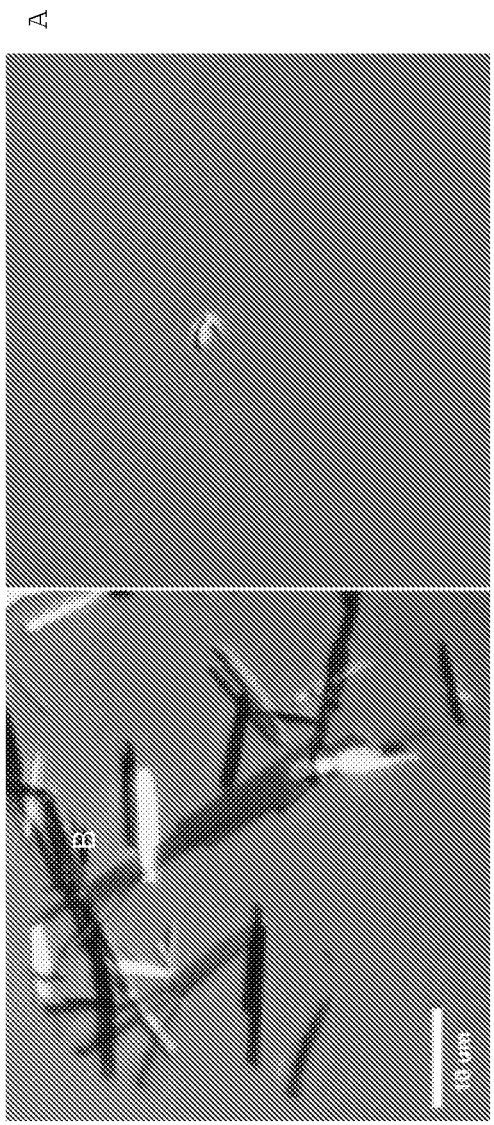
FIG. 25: DIC images showing (A) celecoxib in buffer, and (B) β-casein and celecoxib in buffer. Protein:drug ratio is 1:4. In the presence of protein the solution is transparent and no drug crystals or other micron-scale structures are visible by light microscopy. pH in all images ~7.

The structures formed by the celecoxib and the β-casein were viewed using light microscopy in Nomarski optics, as shown in FIG. 25. In the absence of protein, celecoxib formed large crystals at pH 6.8 (FIG. 25A). In the presence of β-casein, drug solubility was very high, the solution was completely transparent, and hardly any excess of drug crystals were observed by light microscopy (FIG. 25B). Thus, it is contemplated that the β-casein/celecoxib complexes, similar to the β-casein micelles, are of nanometric size.

Figure 26:
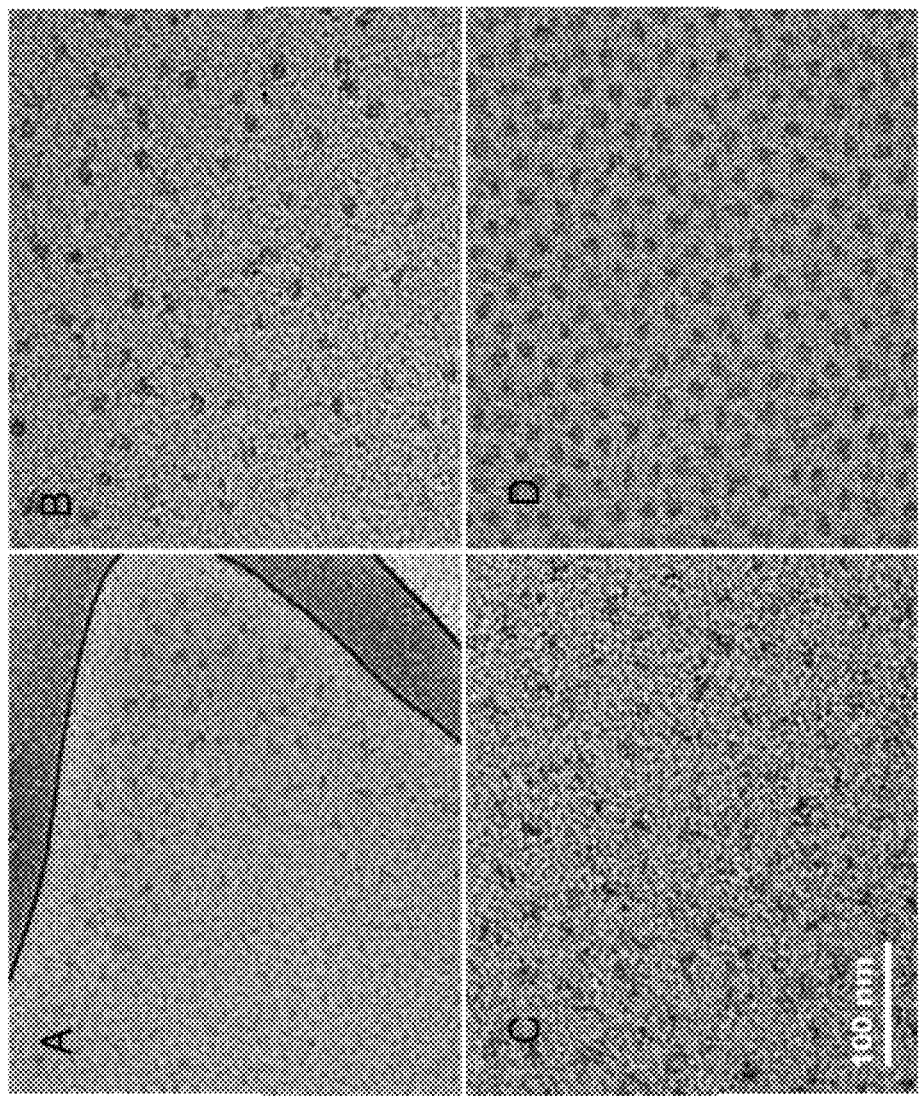
FIG. 26: Cryo-TEM images show an increase in micellar diameter upon increasing drug loading. (A) 0.5 wt % β-casein, 1:1 protein:drug ratio, (B) 0.5 wt % β-casein, 1:8 ratio, (C) 2% β-casein, and (D) 2 wt % β-casein, 1:15 mole ratio. pH ~7.

To probe the native structure of the drug-loaded assemblies at the nanometric scale, cryo-TEM was used. For all the compositions studied, images show the existence of a homogeneous population of small mixed protein-drug micelles. The diameter of the mixed micelles increased slightly upon increasing the drug-to-protein mole ratio. In low concentrations and low loading ratios (0.5 wt %, 1:1 mole ratio, FIG. 26A) the micelles are small and have an oblate shape, similar to empty β-casein micelles in room temperature. The micelles are positioned in different orientations; therefore some of them appear to be round and others appear very narrow. Different dark and light areas along the micelles are caused by density or thickness differences of the vitrified sample film (denser or thicker regions are darker). This appearance indicates non-uniform packing of the β-casein/celecoxib micelles. Micelles with higher loading of 1:8 ratio (FIG. 26B) are larger and more spherical than at 1:1 loading. In higher concentrations, and very high loading ratios (here showing 2 wt % empty micelles (C) and 2 wt % at 1:15 mole ratio in FIG. 26D) the micelles are even more spherical, and they are clearly swollen. The packing is more uniform, as implied by the increased homogeny.

Empty β-casein micelles were degraded within a few days when stored at 4° C. The lifetime of the drug-loaded complexes increased to at least 3 weeks at the same temperature. Stability of the assemblies remains when they were transferred to room temperatures. To further examine the stability, and to increase the shelf-life, the β-casein/celecoxib solution was freeze-dried (lyophilized). This process provided increased stability of the loaded micelles in a dry powder form, for at least 6 months.

Figure 27:
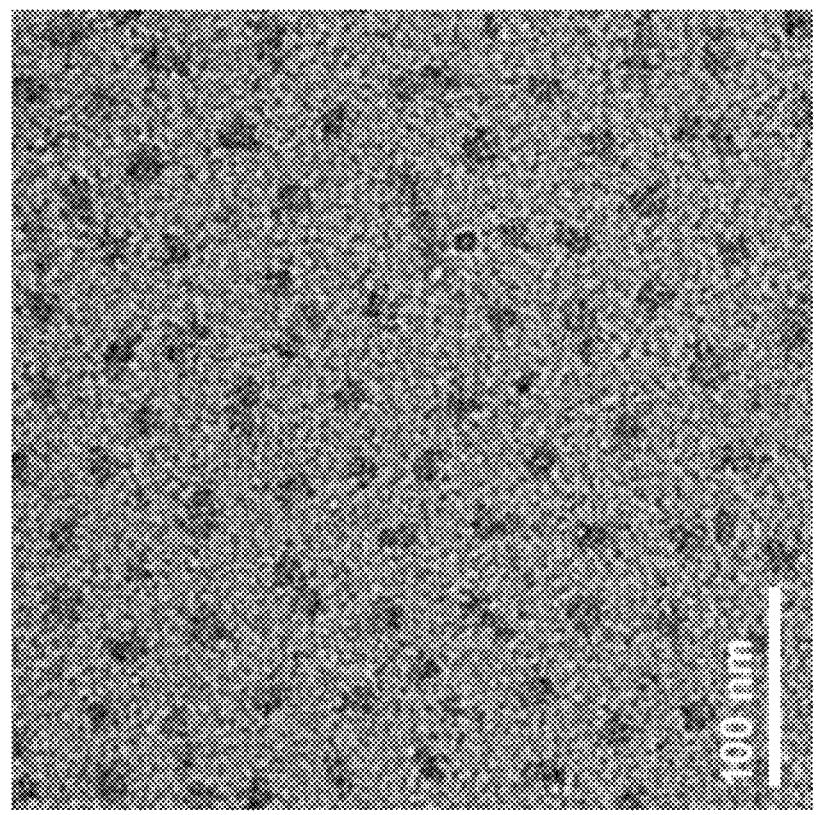
FIG. 27: Cryo-TEM image showing β-casein/celecoxib micelles after lyophilization and re-suspension to 5 wt %. Protein:drug mole ratio is 1:15. pH ~7.

Lyophilized β-casein micelles and β-casein/celecoxib micelles were re-suspended in buffer, back to their original concentration. The solutions were transparent, similar to the original solutions. Furthermore, the lyophilized specimens were re-suspended to a higher concentration to yield a transparent solution with a concentration of β-casein which exceeded the β-casein solubility limit. The micelles dimensions and morphology did not considerably change throughout the procedure. The micelles remained small (<50 nm), and round (FIG. 27).

Figure 28:
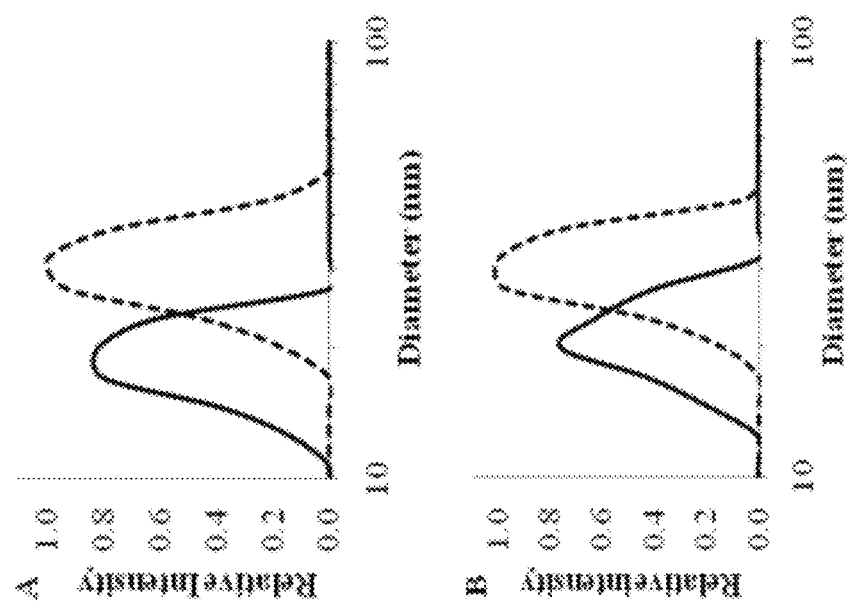
FIG. 28: DLS measurements showing slight increase in micelle diameter upon loading with drug, and no influence of drying on the distribution or the mean diameter. Specimens before (A) and after (B) drying. Solid line: 0.5% β-casein, dashed line: 0.5% β-casein with 1:8 mole ratio celecoxib. pH ~7.

DLS measurements were then performed on 0.5% β-casein micelles loaded with 1:8 mole ratio of celecoxib, in comparison with empty micelles (FIG. 28A), and on the same specimens after lyophilization and re-suspension (FIG. 28B). Empty micelles diameter as measured in DLS is 19 nm±3 nm. Similar results were found in cryo-TEM, were the maximum dimension was about 22 nm. After loading the micelles in 1:8 ratio protein:drug the diameter as measured in DLS increased to 31 nm 5 nm. Some increase in size was also seen in cryo-TEM. Although the two methods gave somewhat different dimensions, increase in size was observed by both. Without being bound by any theory or mechanism of action, the difference can be attributed to the measurement of the distribution of diffusion coefficients using DLS which is transformed to a distribution of hydrodynamic diameters. If the particles are spheres (e.g. the β-casein/celecoxib micelles), the hydrodynamic diameter calculated will be identical or bigger than the actual diameter (Bootz A. et al., Eur J Pharm Biopharm, 2004. 57(2): 369-375). This is considered to be less accurate. Size measurement in cryo-TEM may also be less accurate due to focus and film thickness. Areas of different thickness in the vitrified liquid film may contain different particles. Thick areas contain large particles, and thinner areas contain smaller ones.

The diameter of β-casein after lyophilization and re-suspension was measured to be 21 nm±4 nm. The difference between micellar size before and after drying is within the measurement error. Loaded micelles that were lyophilized and re-suspended did not exhibit any detectable change in diameter after the procedure (diameter after drying was 30 nm±5 nm). Thus DLS results show, in agreement with the cryo-TEM results, that the micelles diameter is slightly increased upon loading with drug, and that the micelles essentially maintain their shape and small nanometric size after drying.

Figure 29:
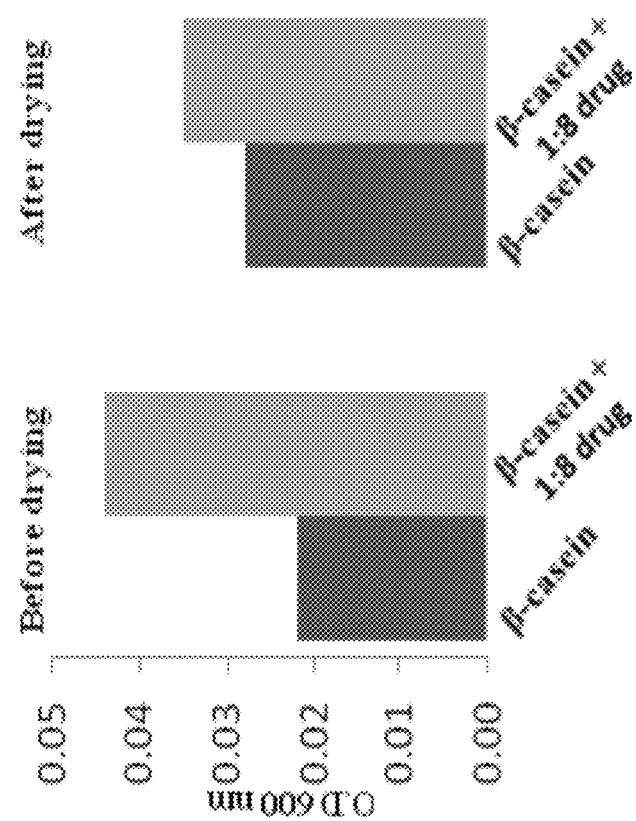
FIG. 29: Turbidity measurements of 1 wt % empty β-casein micelles, micelles loaded with 1:8 celecoxib, and specimens after drying and re-suspending. pH ~7.

Turbidity measurements were performed on 1 wt % β-casein with 1:8 mole ratio celecoxib compared to a 1 wt % β-casein micellar solution. Additional measurements were performed on lyophilized and re-suspended samples of these specimens. As shown in FIG. 29, there is a slight increase in turbidity when celecoxib is loaded to the carrier. All the samples are transparent. This complies with the increase in the micelles size and no formation of bigger aggregates, as indicated by light microscopy, cryo-TEM, and DLS.

Figure 30:
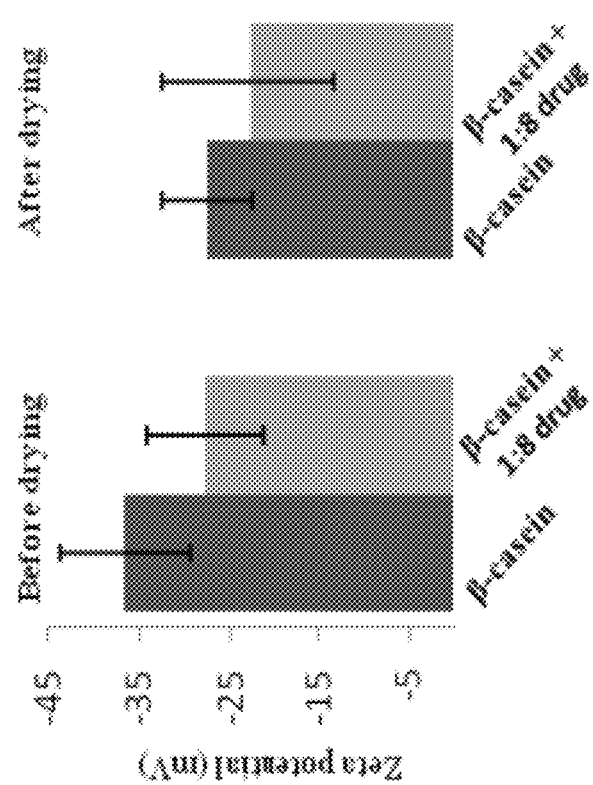
FIG. 30: Zeta potential measurements of 1 wt % empty β-casein micelles, micelles loaded with 1:8 celecoxib, and specimens after drying and re-suspending. pH 7.

Zeta potential measurements were performed on the same dispersions of the turbidity experiment. The results show no significant change in the micelles' surface charge in empty β-casein micelles versus loaded ones (FIG. 30). The zeta potential similarity of empty and loaded micelles supports encapsulation of the drug in the hydrophobic micellar core. The slight decrease in the lyophilized specimens in comparison to the intact ones originates in the higher salt concentration in the lyophilized specimens. Without being bound by any theory or mechanism of action, this is attributed to the highly charged β-casein micelles (~−650 on one micelle) which is masked when the salt concentration is raised. Similar results were obtained with other protein to drug ratios.

Figure 31:
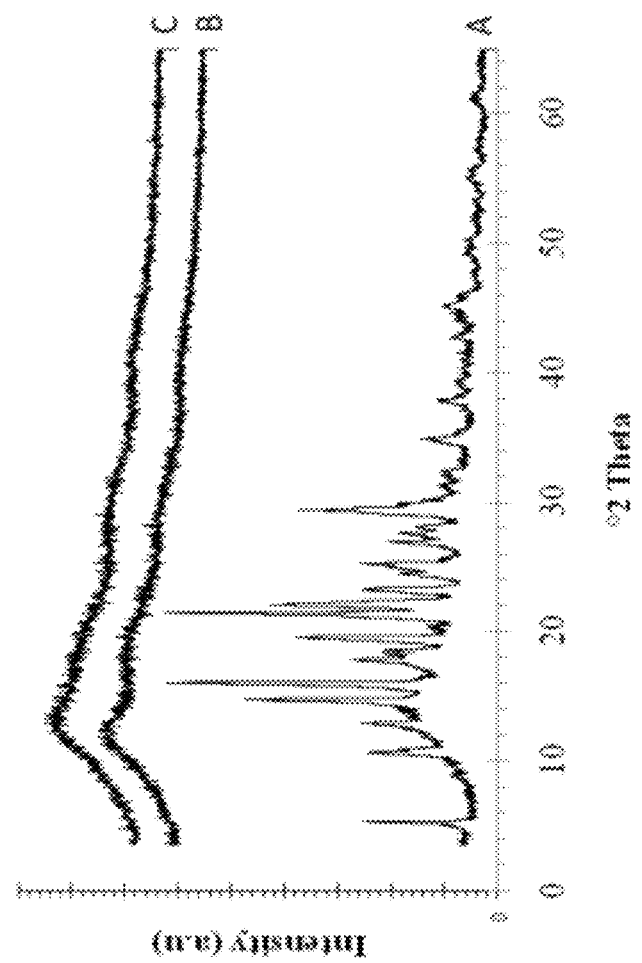
FIG. 31: Wide-angle X-ray diffraction measurements showing the loss of crystallinity of celecoxib in β-casein-celecoxib assemblies. Diffraction patterns are shown for celecoxib powder (A), dried β-casein/celecoxib micelles in 1:8 ratio (B), and dried β-casein micelles (C).

X-ray diffraction measurements were performed on a lyophilized specimen of β-casein and celecoxib in a 1:8 mole ratio, as well as on lyophilized β-casein sample and celecoxib powder. FIG. 31 shows the β-casein/celecoxib micelle diffraction pattern (B), in comparison to the crystalline form of celecoxib powder (A), and the amorphous pattern of dried β-casein micelles (C). No peaks of crystalline celecoxib are observed in the presence of protein, indicating that in the β-casein/celecoxib mixed micelle the celecoxib is present in an amorphous form.

Figure 32:
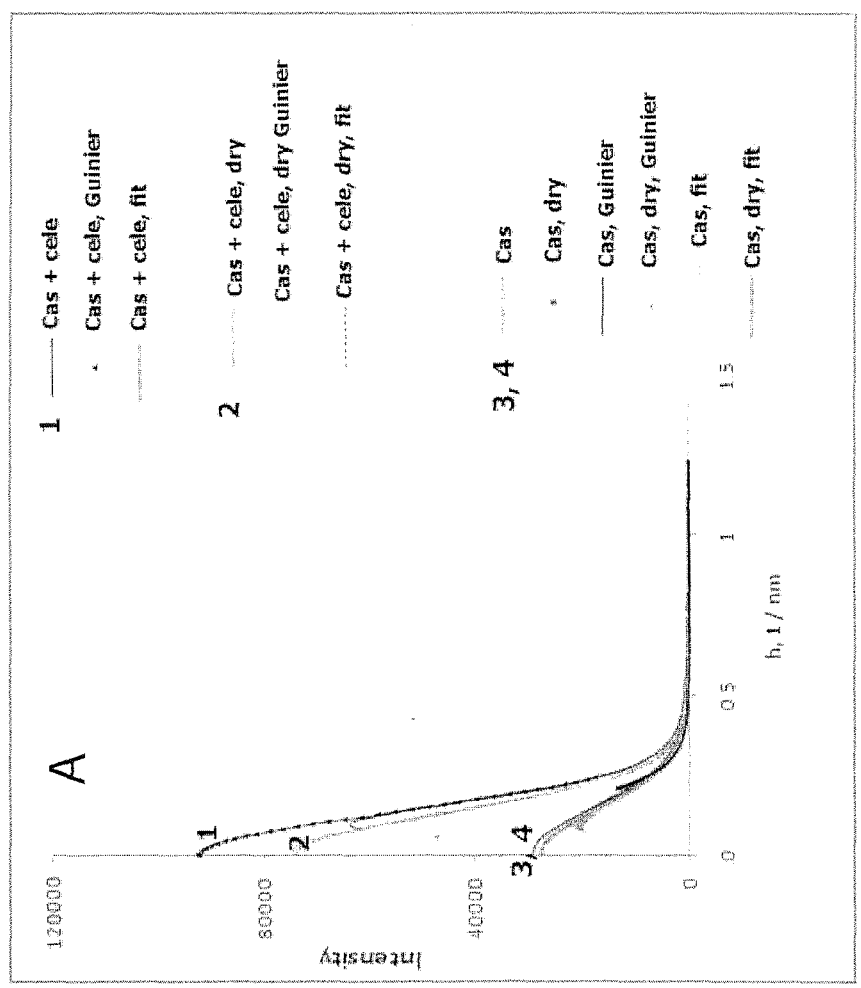
FIG. 32: SAXS measurements of empty β-casein micelles or celecoxib-loaded β-casein micelles, as prepared, and also after lyophilization and re-suspension at pH ~7. Specimens are of 1 wt % β-casein, empty or loaded with 1:8 protein:celecoxib mole ratio.
Figure 33:
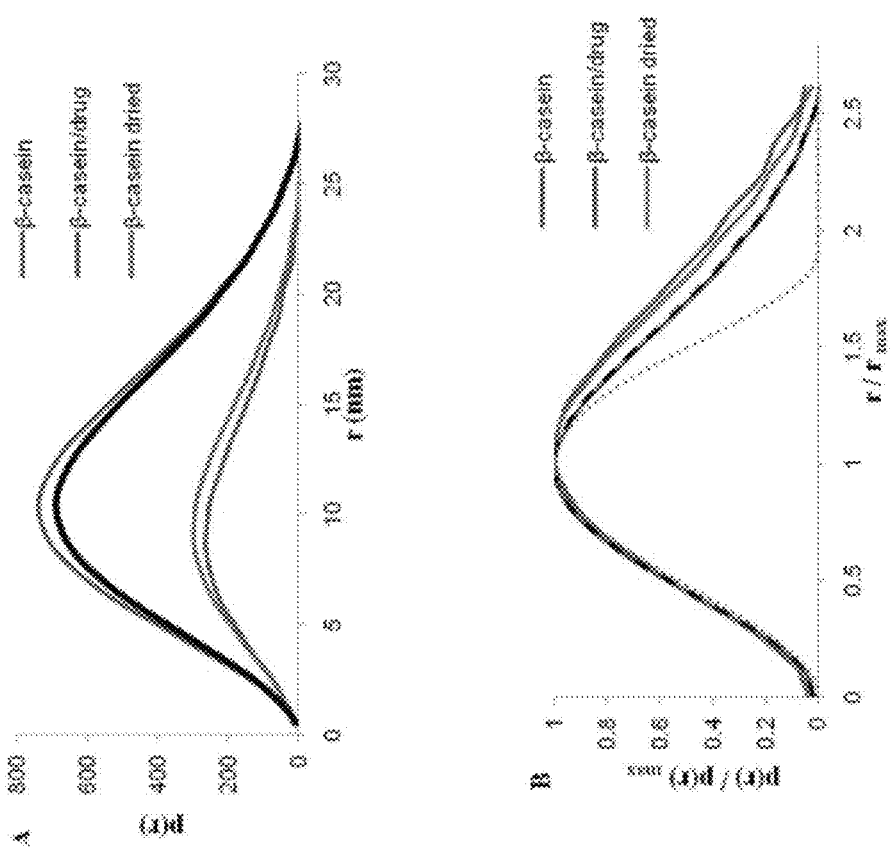
FIG. 33: (A) p(r) obtained from the SAXS curves for β-casein-celecoxib. Specimens are of 1 wt % β-casein, empty or loaded with 1:8 mole ratio celecoxib. (B) Normalized p(r) compared with a homogeneous sphere. $R_{max}$ is the value of r where the $p(r)=p(r)_{max}$ has its maximum. Patterns show micelles encapsulating the drug are larger and more round in shape compared with empty beta-casein micelles.
Figure 34:
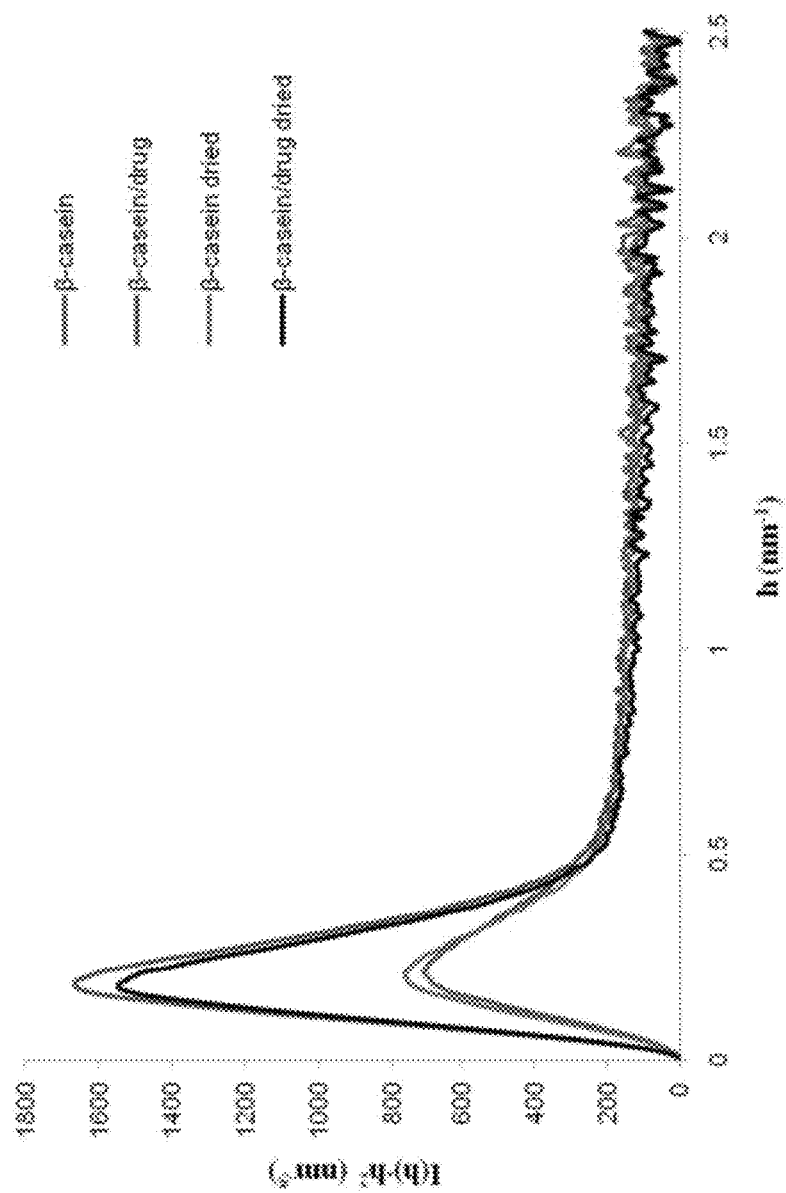
FIG. 34: Kratky plots of empty and celecoxib-loaded β-casein micelles, fresh and after lyophilization and resuspension. Specimens are of 1 wt % β-casein, empty or loaded with 1:8 mole ratio celecoxib. Plots show a clear increase upon loading, but no change in shape or size following lyophilization and re-suspension.

SAXS measurements were performed on empty and celecoxib-loaded β-casein micelles as prepared, and when resuspended after lyophilization. The experimental data and the analysis after fitting to oblate and spherical shape are shown in FIG. 32. Interestingly, lyophilization did not have a significant effect on the SAXS profiles. The pair distance distribution function (PDDF), p(r) is presented in FIG. 33A. The large axis of the micelles can be easily obtained from the curve of p(r) vs. r, where p(r) drops to zero at the maximum dimension. It is clear that the large axis of the micelles slightly increases when drug is loaded to the β-casein micelles. The Kratky plots are shown in FIG. 34. The peaks in the smaller h values in these plots refer to the scattering from the empty and drug-loaded micelles.

Figure 35:
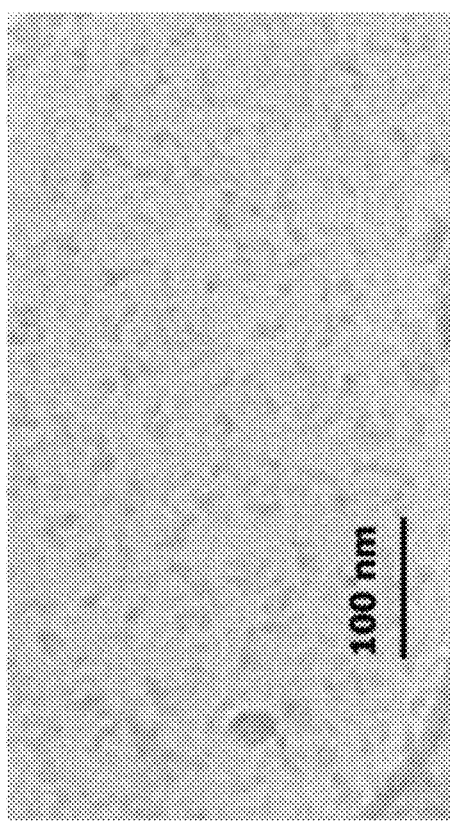
FIG. 35: 2% β-casein, 1:4 protein:celecoxib micelles in lactic acid after lyophilization.

The lyophilization process can be performed at acidic pH as well. FIG. 35 shows 2% beta-casein 1:4 mole ratio protein: celecoxib in lactic acid after lyophilization.

Table 4 shows some parameters calculated from the SAXS analysis. Clearly, the micelles radius of gyration and volume increase when loaded with the drug. The micelles parameters do not seem to be affected by the drying and resuspension processes.

TABLE 4

Table 4: Radius of gyration, micelles volume and density calculated for of the empty and loaded micelles before and after lyophilization.

| Parameter | β-casein | β-casein/ drug | β-casein dried | β-casein/ drug dried |
|---|---|---|---|---|
| Rg (from Guinier apr.) (nm) | 7.8 | 9.0 | 8.1 | 9.0 |
| V, from a, b (nm³) | 2410 | 4336 | 2841 | 4419 |
| Density (g/cm³) | 1.23 | 1.27 | 1.23 | 1.27 |

EXAMPLE 14

Representative Results with Budesonide in Neutral pH

Figure 36:
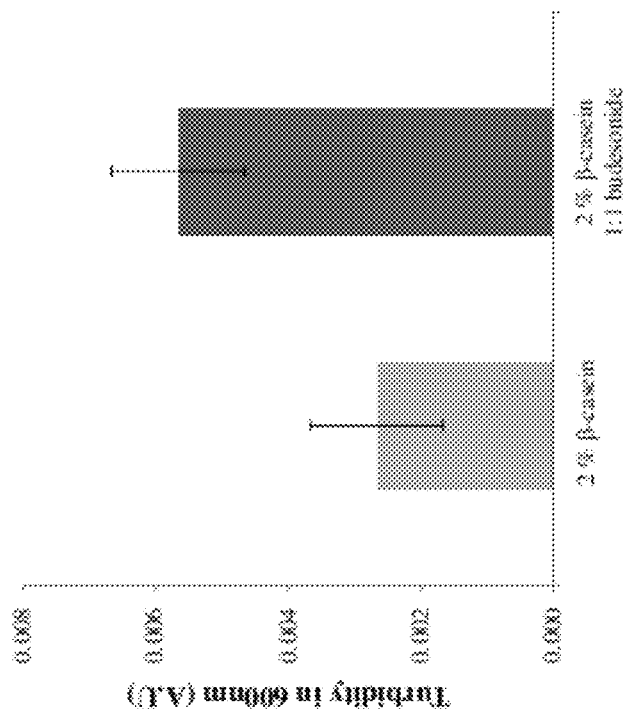
FIG. 36: Turbidity of 2 wt % empty β-casein micelles and micelles loaded with 1:1 mole ratio budesonide. pH ~7.

Samples of β-casein and budesonide were prepared in hepes buffer with pH 7.0. Turbidity measurements were performed on 2 wt % empty β-casein micelles versus micelles loaded with 1:1 budesonide. The turbidity was slightly increased when budesonide was added to the micelles, although the solution is transparent, which can suggest that the size of the micelles is slightly increased (FIG. 36).

Figure 37:
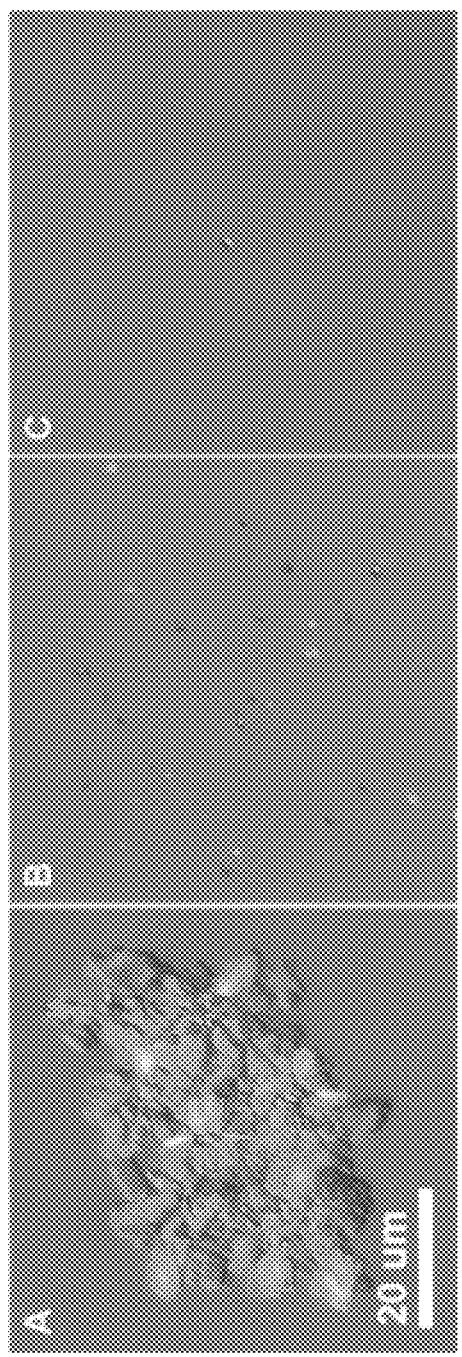
FIG. 37: DIC images of budesonide in hepes buffer (A), 2 wt % β-casein with 1:2 mole ratio protein-budesonide, initially dissolved in EtOH (B), 2 wt % β-casein with 1:2 mole ratio budesonide, initially dissolved in DMSO (C).

Budesonide was dissolved in either DMSO or ethanol. Light microscopy in Nomarski optics reveals that the control specimens of budesonide in buffer contain large crystals (FIG. 37A). When the same amount of drug is dissolved in ethanol (up to 5 wt % final ethanol concentration) and titrated to a protein solution, the solubility is increased and smaller structures are observed by light microscopy (FIG. 37B). The solubility is increased even further when the drug is initially dissolved in DMSO. Under these conditions hardly any excess drug was observed by light microscopy (FIG. 37C).

Figure 38:
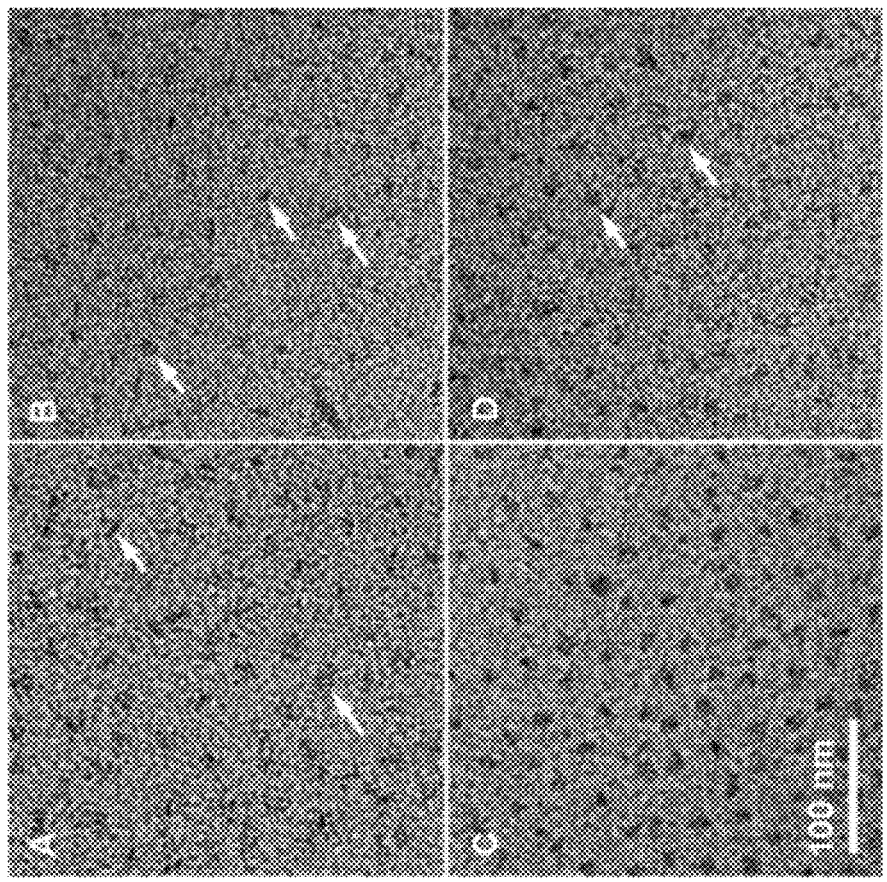
FIG. 38: Cryo-TEM images of (A) 2 wt % β-casein, (B) 2 wt % β-casein with 1:1 mole ratio protein-budesonide, (C) 2 wt % β-casein with 1:4 mole ratio protein-to-budesonide, and (D) 2 wt % β-casein with 1:2 mole ratio protein-budesonide, Drug was initially dissolved in DMSO.

Cryo-TEM images show that micelles of β-casein loaded with 1:1 mole ratio protein:drug (FIG. 38B) slightly more round than empty β-casein micelles (FIG. 38A), as seen by cryo-TEM. Images of the specimen with 1:4 protein:drug (FIG. 38C) show that the micelles are more swollen and are packed more densely than the 1:1 protein:drug micelles and the empty micelles. In these two experiments the drug was dissolved in ethanol. When dissolving budesonide in DMSO cryo-TEM shows (FIG. 38D) again densely packed and swollen micelles compared with empty β-casein micelles.

Figure 39:
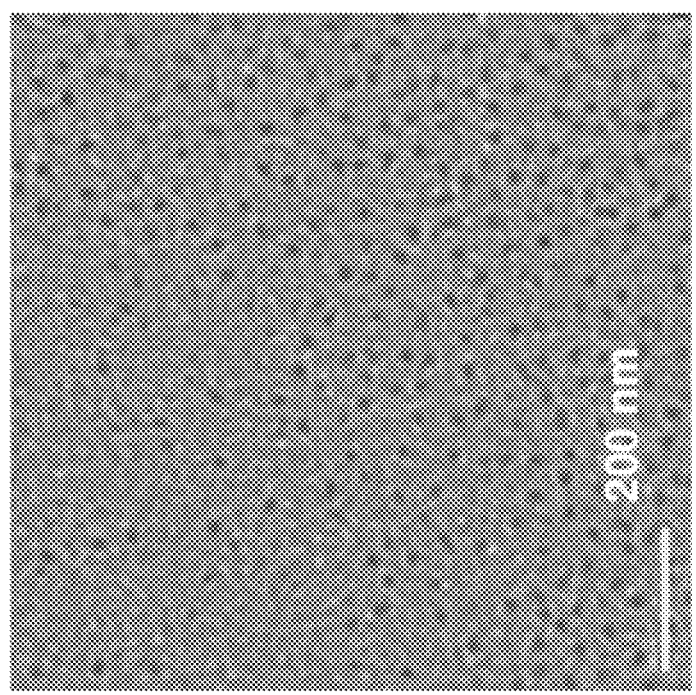
FIG. 39: Cryo-TEM data of budesonide-loaded micelles (pH ~7), after drying and re-suspension to 5 wt % in hepes buffer at pH ~7. Drug to protein mole ratio is 4:1.

The 2 wt % β-casein with 1:4 protein:drug mole ratio specimen prepared in neutral pH was lyophilized, and resuspended in water to a higher concentration of 5 wt % protein. Cryo-TEM reveals again (FIG. 39) round micelles similar to those found before lyophilization. As with celecoxib, lyophilization does not seem to affect the micelles size or shape.

Figure 40:
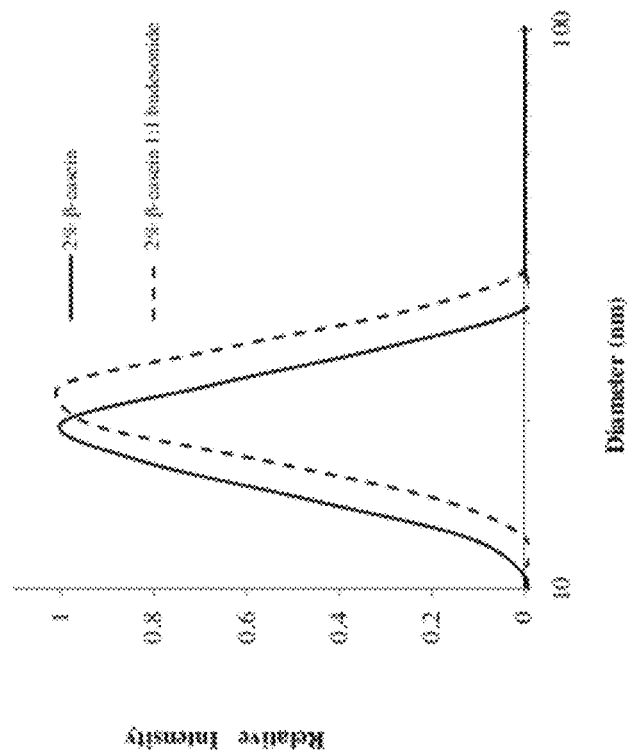
FIG. 40: DLS measurements showing a slight increase in micelle diameter upon loading with budesonide.

DLS measurements were performed on 2 wt % empty β-casein micelles versus micelles loaded with 1:1 budesonide. The micelles diameter slightly increased after loading the drug, from 19.6±3.4 nm to 22.5±3.9 nm (FIG. 40).

EXAMPLE 15

Representative Results with Cholesterol in Neutral pH

β-Casein micelles were prepared in protein concentration of 2 wt % in hepes buffer. Cholesterol was added in β-casein: cholesterol mole ratios ranging from 1:0.5 to 1:3.

Figure 41:
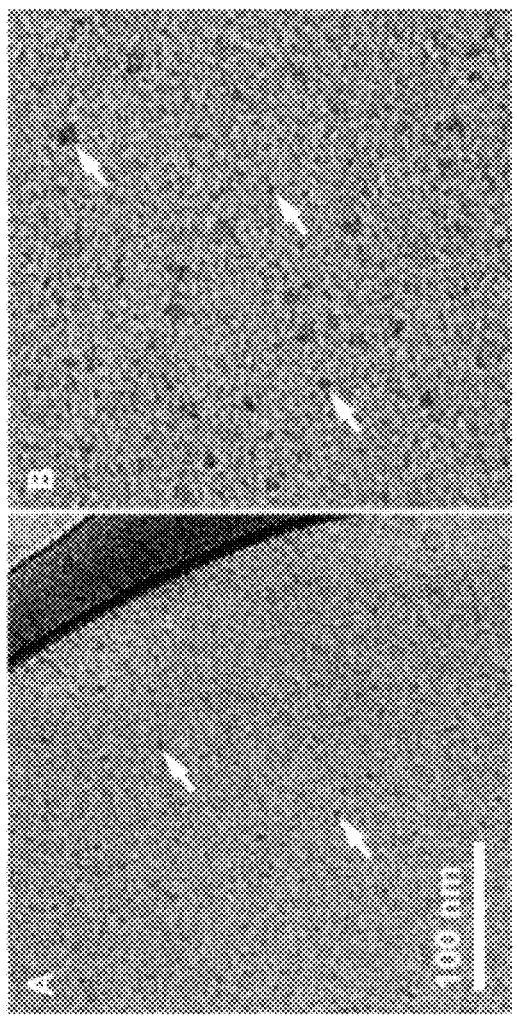
FIG. 41: Cryo-TEM images of (A) insulin in hepes buffer, and (B) 1 wt % casein with 1:1 mole ratio β-casein-to-insulin.
Figure 42:
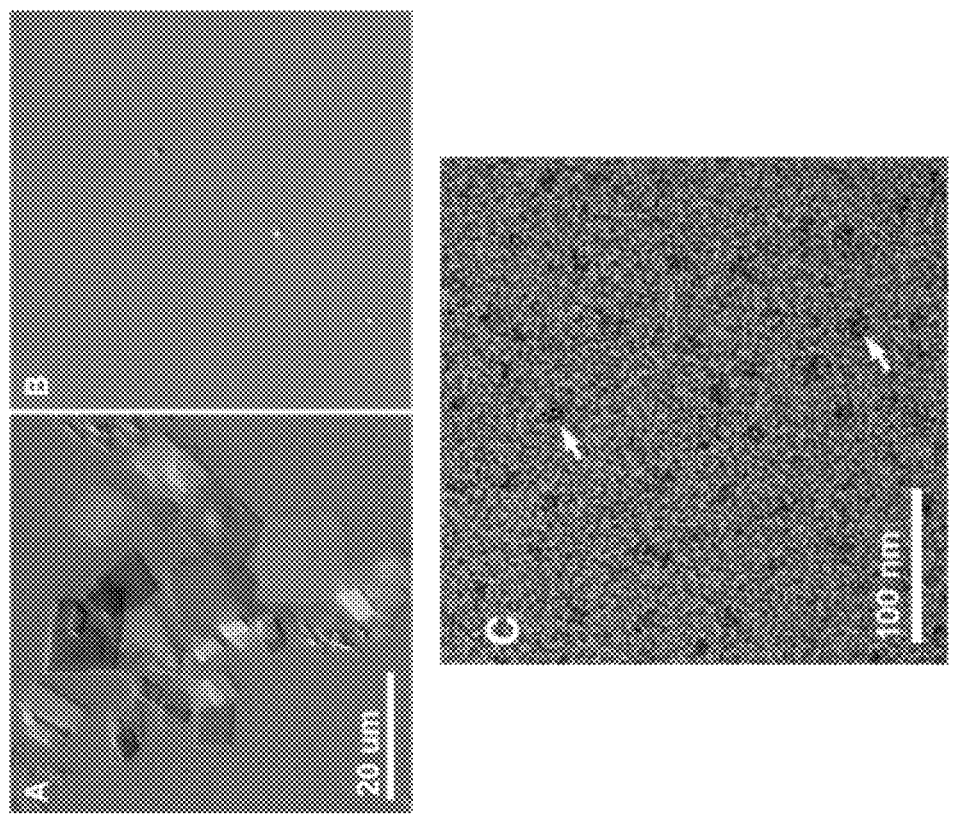
FIG. 42: DIC images of (A) cholesterol in hepes buffer and (B) 2 wt % β-casein with 1:0.5 mole ratio cholesterol. (C) Cryo-TEM image of 2 wt % β-casein with 1:1 mole ratio cholesterol.

Cholesterol does not dissolve in buffer at all, and light microscopy shows characteristic large rectangular crystals (FIG. 41A). The specimen of 2 wt % β-casein with 1:0.5 β-casein: cholesterol was bluish and did not precipitate, and by light microscopy only few small structures were observed (FIG. 41B). Cryo-TEM shows that when cholesterol is added to β-casein the micelles become more spherical and swollen, and clearly contain cholesterol (FIG. 41C).

EXAMPLE 16

Water Content within the Dried Composition Assemblies

In this experiment the water content of celocoxib (CXB), beta-casein (β-CN) 1% nanocarriers, Sigma beta-casein (β-CN, Sigma material), and CXB-loaded β-CN 1% nanocarriers was measured by Metrohm 831 Karl Fischer Coulometer.

The water content of dried CXB samples is shown in table 5.

TABLE 5

Water content of CXB samples

| Sample # | Sample weight (mg) | Water weight (mg) | % water |
|---|---|---|---|
| 1 | 10.1 | 0.6442 | 6.4 |
| 2 | 10.5 | 0.1433 | 1.4 |
| 3 | 10.1 | 0.3220 | 3.2 |
| 4 | 9.1 | 0.6119 | 6.7 |
| 5 | 10.3 | 0.4777 | 4.6 |
| AVR | | | 4.5 |

The water content of dried β-CN 1% nanocarriers is shown in table 6.

TABLE 6

Water content of β-CN 1% nanocarriers

| | Empty β-CN 1% nanocarriers | | | CXB-loaded β-CN 1% nanocarriers | | |
|---|---|---|---|---|---|---|
| Sample # | Sample weight (mg) | Water weight (mg) | % water | Sample weight (mg) | Water weight (mg) | % water |
| 1 | 13.3 | 2.0458 | 15.4 | 12.8 | 1.4480 | 11.3 |
| 2 | 13.8 | 2.3598 | 17.1 | 13.6 | 1.6469 | 12.1 |
| 3 | 12.4 | 1.9545 | 15.8 | 13.4 | 1.4529 | 10.8 |
| AVR | | | 16.1 | | | 11.4 |

Tables 5 and 6 demonstrate that the average water content of the lyophilized (dried) powders of empty and CXB-loaded β-CN 1% nanocarriers is more than 10% w/w.

The water content of dried β-CN (Sigma material) is shown in table 7.

TABLE 7

Water content of β-CN samples

| Sample # | Sample weight (mg) | Water weight (mg) | % water |
|---|---|---|---|
| 1 | 13.6 | 2.0433 | 15.0 |
| 2 | 13.2 | 1.2447 | 9.4 |
| 3 | 11.6 | 1.7028 | 14.7 |
| AVR | | | 13.0 |

Table 7 similarly to tables 5 and 6 demonstrates that the average water content of the lyophilized (dried) powders of the β-CN (Sigma material) is also more than 10% w/w.

In an attempt to reduce the water content, an additional lypholization cycle was performed for the empty and CXB-loaded β-CN 1% nanocarriers. After this second lyophilization cycle water content was measured by Metrohm 831 Karl Fischer Coulometer.

Specifically, the first cycle lasted for 24 hours (data is presented in tables 5-7) then all samples were subjected to an additional cycle of lyophilization that lasted for 48 hours (total of 72 hours). Tables 8 and 9 present the results of samples that were subjected to 24, 68, and 72 hours of lyophilization.

TABLE 8

Water content (% of dry powders) of empty and CXB-loaded β-CN 1% nanocarriers after different lyophilization times

| | Empty β-CN 1% nanocarriers | | | CXB-loaded β-CN 1% nanocarriers | | |
|---|---|---|---|---|---|---|
| Sample | Sample weight (mg) | Water weight (mg) | % water | Sample weight (mg) | Water weight (mg) | % water |
| 72 hours lyophilization | 12.3 | 2.0683 | 16.8 | 10.1 | 1.2395 | 12.3 |
| | 11.1 | 1.3393 | 12.1 | 11.7 | 1.0970 | 9.4 |
| | 15.2 | 1.6274 | 10.7 | ND* | ND* | ND* |
| | AVR | | 13.2 | AVR | | 10.9 |
| 68 hours lyophilization | 13.6 | 2.1984 | 16.2 | 10.4 | 0.9856 | 9.5 |
| | 13.2 | 1.5911 | 12.1 | 10.6 | 0.8357 | 7.9 |
| | 11.5 | 1.3587 | 11.8 | 12.4 | 1.1940 | 9.6 |
| | AVR | | 13.4 | AVR | | 9.0 |

*not done as no sufficient quantity of powder remained

TABLE 9

Water content (% of dry powders) of β-CN and β-CN micelles (empty and CXB-loaded β-CN 1% nanocarriers) after different lyophilization times

| | % water content (% of dry powder)* Lyophilization time | | | |
|---|---|---|---|---|
| Sample | none | 24 h | 68 h | 72 h |
| β-CN (material from Sigma) | 13.0 | NA | NA | NA |
| Empty β-CN 1% nanocarriers | NA | 16.1 | 13.4 | 13.2 |
| CXB-loaded β-CN 1% nanocarriers | NA | 11.4 | 9.0 | 10.9 |

*Average of 2-3 measurements

In conclusion, the water content of the lyophilized powders of empty and CXB-loaded β-CN 1% nanocarriers were still relatively high (about 11-13%) after further lyophilization. Two additional days of additional lyophilization following the initial 24 hours lyophilization cycle reduced a small amount of water from the empty β-CN 1% nanocarriers. The CXB-loaded β-CN 1% nanocarriers remained with substantially the same amount of water.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

While certain features of the present invention have been illustrated and described herein, many modifications, substitutions, changes, and equivalents may occur to those of ordinary skill in the art. It is, therefore, to be understood that the appended claims are intended to cover all such modifications and changes as fall within the true spirit of the present invention.

The invention claimed is:

1. A composition comprising β-casein micelles, assemblies or complexes thereof, wherein the micelles, assemblies or complexes thereof comprise: (1) β-casein; and (2) at least one therapeutic agent incorporated within said micelles, assemblies or complexes, wherein:
the composition is a dried composition;
said β-casein comprises at least about 70% of the total casein content; and
said micelles, assemblies or complexes are not held together by calcium phosphate bridges.

2. The composition of claim 1, wherein said dried composition is freeze-dried.

3. The composition of claim 1, wherein said composition is free of calcium ions.

4. The composition of claim 1, wherein said dried composition comprises less than 15% of water.

5. The composition of claim 1, wherein said micelles, assemblies or complexes have a diameter of less than 100 nm.

6. The composition of claim 1, wherein said β-casein is at least about 80% of the total casein content.

7. The composition of claim 1, formulated as a tablet or capsule.

8. The composition of claim 1, wherein said therapeutic agent comprises an agent having at least one characteristic selected from the group consisting of: hydrophobicity, poor bioavailability, instability, or any combination thereof.

9. The composition of claim 1, wherein said therapeutic agent is celecoxib.

10. The composition of claim 9, comprising about 175 to about 225 mg celecoxib in 1 g of the composition.

11. The composition of claim 9, wherein said celecoxib is in an amorphous form.

12. The composition of claim 1, wherein said therapeutic agent is budesonide or methylprednisolone hemisuccinate sodium salt (MPS).

13. The composition of claim 12, comprising about 75 to about 125 mg budesonide in 1 g of the composition.

14. The composition of claim 1, wherein said therapeutic agent is sodium clodronate.

15. The composition of claim 1, wherein said therapeutic agent is selected from the group consisting of: a peptide, a protein, a hormone or a vitamin.

16. The composition of claim 1, comprising between about 70% (w/w) and about 99% (w/w) β-casein and between about 1% (w/w) and about 30% (w/w) of the at least one therapeutic agent.

17. The composition of claim 1, wherein the mole ratio between the β-casein and the therapeutic agent is at least about 1:1 to about 1:20.

18. The composition of claim 1, wherein the mole ratio between the β-casein and the therapeutic agent is at least about 1:10 to about 1:20.

19. The composition of claim 1, wherein the composition is stable for at least one month.

20. A suspension comprising the composition of claim 1 in an aqueous solution.

21. The suspension of claim 20, wherein the micelles, assemblies or complexes have a diameter of less than 100 nm.

22. The suspension of claim 20, wherein the micelles, assemblies or complexes have a diameter of less than 50 nm.

23. The suspension of claim 20, wherein said suspension is stable for at least two weeks.

24. The suspension of claim 20, wherein said suspension is free of calcium ions.

25. A method for preparing a suspension comprising micelles, assemblies or complexes thereof and at least one therapeutic agent, comprising the step of suspending the composition of claim 1 in an aqueous solution, thereby preparing a suspension comprising micelles, assemblies or complexes thereof and at least one therapeutic agent.

26. The composition of claim 1, wherein said micelles, assemblies or complexes are formed in the absence of calcium.

* * * * *